United States Patent [19]

Baldwin et al.

[11] Patent Number: 4,853,383

[45] Date of Patent: Aug. 1, 1989

[54] β-BLOCKING SUBSTITUTED IMIDAZOLES

[75] Inventors: John J. Baldwin, Gwynedd Valley; Gerald S. Ponticello, Lansdale, both of Pa.

[73] Assignee: Merck & Co., Inc., Rahway, N.J.

[21] Appl. No.: 905,088

[22] Filed: Sep. 8, 1986

Related U.S. Application Data

[60] Continuation-in-part of Ser. No. 607,909, May 7, 1984, Pat. No. 4,642,311, Continuation-in-part of Ser. No. 503,923, Jun. 13, 1983, Pat. No. 4,567,276, Division of Ser. No. 255,202, Apr. 20, 1981, Pat. No. 4,440,774, Continuation-in-part of Ser. No. 184,501, Sep. 5, 1980, abandoned, Continuation of Ser. No. 801,120, May 27, 1977, abandoned, Continuation of Ser. No. 641,420, Dec. 17, 1975, Pat. No. 4,137,983, Continuation-in-part of Ser. No. 554,372, Mar. 3, 1975, abandoned.

[51] Int. Cl.$^4$ .................. A61K 31/535; C07D 413/06
[52] U.S. Cl. .................. 514/235.8; 514/341; 514/398; 514/400; 544/58.4; 544/82; 544/139; 544/357; 544/370; 546/187; 546/210; 546/278; 548/337; 548/342; 548/343; 548/346
[58] Field of Search .............. 548/337, 342, 343, 346; 514/398, 400, 235.8, 341; 546/187, 210, 278; 544/58.4, 82, 139, 357, 370

[56] References Cited

U.S. PATENT DOCUMENTS

| | | | |
|---|---|---|---|
| 3,946,009 | 3/1976 | Wasson et al. | 544/120 |
| 4,027,027 | 5/1977 | Jaeggi et al. | 514/349 |
| 4,042,586 | 8/1977 | Wasson et al. | 544/60 |
| 4,115,575 | 9/1978 | Frei et al. | 514/255 |
| 4,125,530 | 11/1978 | Baldwin et al. | 546/167 |
| 4,131,685 | 12/1978 | Smith | 514/595 |

OTHER PUBLICATIONS

Chemical Abstracts, 74:22855m (1971) [Ger. offen. 2,018,522, Stuart, et al., 11/12/70].
Chemical Abstracts, 80:3520g(1974) [Japan. 73 32, 113, Kuroki, et al., 10/4/73].
Lombardino, J., J. Het. Chem., 10, 697(1973).
Wolff, Burger's Medicinal Chemistry, 4th ed., part III, pp. 310 and 331.

Primary Examiner—Richard A. Schwartz
Attorney, Agent, or Firm—Edward W. Murray; Michael C. Sudol

[57] ABSTRACT

Novel substituted imidazoles and methods for their preparation are disclosed. These imidazoles, and their salts, exhibit pharmacological activity which includes antihypertensive activity and β-adrenergic blocking activity.

9 Claims, No Drawings

β-BLOCKING SUBSTITUTED IMIDAZOLES

BACKGROUND OF THE INVENTION

This is a continuation-in-part of copending application Ser. No. 607,909 filed May 7, 1984 which is a continuation-in-part of copending application Ser. No. 503,923 filed June 13, 1983 no U.S. Pat. No. 4,567,276 issued Jan. 28, 1986, which is a division of Ser. No. 255,202 filed Apr. 20, 1981, U.S. Pat. No. 4,440,774 issued Apr. 3, 1984, which is a continuation-in-part of Ser. No. 184,501 filed Sept. 5, 1980, now abandoned, which is a continuation of application Ser. No. 801,120, filed on May 27, 1977, now abandoned, which, in turn, is a continuation of application Ser. No. 641,420 filed Dec. 17, 1975 now U.S. Pat. No. 4,134,983 issued Jan. 16, 1979 which, in turn, is a continuation-in-part of application Ser. No. 554,372 filed Mar. 3, 1975, now abandoned.

The present invention involves novel imidazoles which have antihypertensive and β-adrenergic blocking activity.

Various chemical agents are available for treating hypertension in man and animals. Certain trifluoromethyl imidazoles are known to have substantial antihypertensive activity. These imidazoles are disclosed in U.S. Pat. No. 3,786,061.

Another class of agents known as β-adrenergic blocking agents, are also available. These β-blocking agents affect cardiac, vascular, ocular and pulmonary functions and can be mild antihypertensives. Specifically, these agents have the capability of reducing heart rate, counteracting vasodepression, suppressing bronchodilation, reducing intraocular pressure, and decreasing systemic blood pressure. β-adrenergic blocking agents, their chemical structure and activity, are disclosed in "Clinical Pharmacology and Therapeutics" 10, 292–306 (1969). Various β-adrenergic blocking agents are also described in the following patents: U.S. Pat. Nos. 3,048,387; 3,337,628; 3,655,663; 3,794,650; 3,832,470; 3,836,666; 3,850,945; 3,850,946; 3,850,947; 3,852,291 and British No. 1,194,548.

Where an antihypertensive agent acts principally via vasodilation, it may cause undesirable side effects such as substantially increased heart rate (tachycardia).

Novel imidazoles characterized by having amino-substituted propoxyaryl substitution have been discovered. These imidazoles have unexpected antihypertensive activity and β-adrenergic blocking activity.

SUMMARY OF THE INVENTION

This invention is directed toward novel imidazoles having amino substituted propoxy aryl substitution and salts thereof; their preparation; pharmaceutical composition containing said imidazoles; and method of treatment of animals e.g. those having hypertension or angina pectoris, using said imidazoles.

DESCRIPTION OF THE PREFERRED EMBODIMENTS

An embodiment of the present invention is compounds having the formula

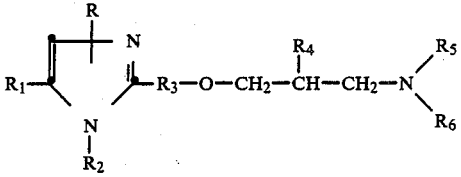

wherein

R and $R_1$ are independently selected from hydrogen, $C_1$–$C_{10}$ alkyl, substituted $C_1$–$C_{10}$ alkyl having 1–3 substituents, cycloalkyl, aryl, substituted aryl having 1–5 substituents, heterocyclic group having 5–6 ring atoms, halogen, cyano, carboxy and carboxy derivatives;

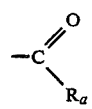

wherein $R_a$ is H or $C_1$–$C_6$ alkyl;

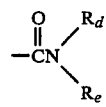

wherein $R_d$ and $R_e$ are independently hydrogen, $C_1$–$C_8$ linear or branched alkyl, $C_6$ or $C_{10}$ unsubstituted or substituted aryl having 1–2 substituents selected from $C_1$–$C_4$ alkyl, halo, alkoxy or hydroxy, or $R_d$ and $R_e$, together with the N atom, can be joined to form a 6-membered heterocyclic ring containing an additional O, S, NH or N-lower $C_1$–$C_8$ alkyl heteroatom;

$R_2$ is selected from hydrogen, $C_1$–$C_{10}$ alkyl, hydroxy-$C_1$–$C_{10}$-alkyl and $C_3$–$C_6$ alkenyl, $R_3$ is selected from aryl having 6 ring atoms of which 0–2 are non-carbon, substituted aryl having 1–4 substituents, fused ring aryl having 9–10 ring atoms of which 0–2 are non-carbon, and substituted fused ring aryl having 1–4 substituents, $R_4$ is selected from hydroxy and

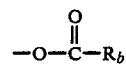

wherein $R_b$ is $C_1$–$C_6$ alkyl, and $R_5$ and $R_6$ when separate, are independently selected from hydrogen, $C_1$–$C_6$ alkyl and substituted $C_1$–$C_6$ alkyl having 1–3 substituents and, when joined, form a 5–6 membered N-alicyclic ring;

and, pharmacologically acceptable acid addition and quaternary ammonium salts thereof.

The compounds have an asymmetric center and the present invention includes enantiomers, racemates and mixtures of isomers. When the compound is named without specific designation, it is intended to embrace all isomers, racemates and mixtures of isomers.

Compounds of particular interest have the formula:

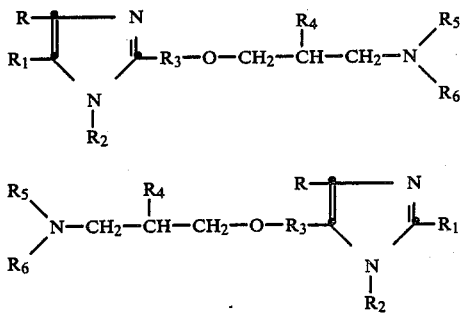

Useful R and $R_1$ alkyl groups include unsubstituted as well as substituted alkyl, cycloalkyl as well as branched and linear alkyl groups. These alkyl groups may contain up to 10 alkyl carbons, preferably up to 8 alkyl carbon atoms and more preferably from 1 to 6 alkyl carbons. Examples of suitable R and $R_1$ unsubstituted alkyl groups are methyl, isopropyl, cyclopropyl, cyclopentyl, 2-methyl-n-butyl, decyl, 2-ethyl-n-hexyl; suitable R and $R_1$ substituted alkyl groups have 1-3 substituents such as halo (Cl, Br, I, F), hydroxy, phenyl-$C_1$-$C_4$ alkoxy, —exemplified by —$CCl_3$, bromohexyl, $CH_3$—O—$CH_2$—$CH_2$—, hydroxypropyl, diiodoethyl, trifluoromethyl, benzyl, chlorodecyl, and the like.

Useful R and $R_1$ aryl groups include aryl groups having up to 10 ring carbon atoms. These aryl groups include single ring as well as fused ring aryls, unsubstituted aryls as well as substituted aryls having from 1-5 substituents. These substituents include alkyl, preferably $C_1$-$C_6$ alkyl, alkoxy preferably $C_1$-$C_6$ alkoxy, cyano, halo (Cl, I, Br and F), nitro, amino, carboxy, hydroxy, carbonyl, -SH, sulfamoyl, thioalkyl, phenyl, and the like. Examples of suitable aryl R and $R_1$ groups are phenyl, chlorophenyl, dibromophenyl, fluorophenyl, tolyl, xylyl, hexylphenyl, dodecylphenyl, tertbutylphenyl, methoxyphenyl, $C_6H_{13}$—O—phenyl, HO—$C_6$-$H_4$—, carboxyphenyl,

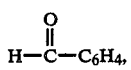

sulfamoylphenyl, N,N-dimethylsulfamoylphenyl, naphthyl, indanyl, chloronaphthyl, trichlorophenyl, HO—$CH_2$—$C_6H_4$—, pentafluorophenyl, the tetralin group, cyanophenyl, chlorohydroxyphenyl, $C_1$—$C_6$—alkyl—S—$C_6H_4$—,

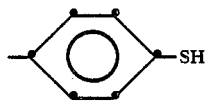

and the like.

Useful R and $R_1$ heterocyclic groups have 5-6 ring atoms of which 1-3 and preferably 1-2 are hetero atoms and the quinolyl group. Substituted as well as unsubstituted heterocyclic groups are included. The hetero atoms are O, S and N. Examples of suitable R and $R_1$ heterocyclic groups are pyridyl, pyrazinyl, pyrimidinyl, pyridazinyl substituted pyridyl such as dimethylpyridyl, methylpyridyl, chloropyridyl, dichloropyridyl, diethylpyridyl, trimethylpyridyl, methylethylpyridyl, ethylpyridyl, bromopyridyl, and analogous substituted pyrazinyl, pyrimidinyl, and pyridazinyl groups; pyridyl-N-oxide, methylpyridyl-N-oxide, furyl, thienyl, and the like.

It is preferred that at least one of R and $R_1$ is hydrogen.

Other useful R and $R_1$ groups are cyano, carboxy, carboxy derivatives such as

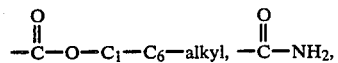

N-mono-$C_1$-$C_6$-alkyl-and N,N-di-$C_1$-$C_6$-alkylcarbamoyl; halogen preferably Br, Cl and F; and

wherein $R_a$ is hydrogen or $C_1$-$C_6$ alkyl, and the like.

Useful $R_2$ alkyl groups have up to 10 carbons, are unsubstituted or monohydroxysubstituted and include cycloalkyl as well as branched and straight chain alkyl. $R_2$ alkyl groups having 1-6 carbons are preferred, with 1-4 carbon atoms more preferred. Examples of suitable $R_2$ alkyl groups are methyl, ethyl, decyl, tert-butyl, isopropyl, 3-hydroxypropyl, 2-hyrdroxybutyl and the like. Useful $R_2$ alkenyl groups have 3-6 carbon atoms and are exemplified by allyl, —$CH_2$—$CH_2$—CH—CH=$CH_2$, and the like.

Preferred compounds are those where $R_2$ is H.

$R_3$ is an aryl group. The aryl group includes single ring (6-ring atoms) and fused ring (9-10 ring atoms) groups having 0-2 nitrogen ring atoms, both substituted as well as unsubstituted moieties.

The $R_3$ heterocyclic groups contain 1 or 2 nitrogen atoms. Examples of such useful heterocyclic groups are pyridyl, halopyridyl, $C_1$-$C_3$ alkylpyridyls, pyridyl-N-oxides, cyanopyridyl, pyrazinyl, pyridazinyl, pyrimidinyl, quinolyl, and the like. Preferred $R_3$ heterocyclic groups are substituted or unsubstituted groups having the formula

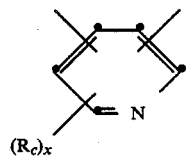

wherein x is 0-4 and $R_c$ is hydrogen, halo, $C_1$-$C_4$ alkyl, $C_1$-$C_4$ alkoxy and hydroxy. $R_c$ may also be other groups as defined hereinafter in connection with $R_3$ carbocyclic aryl groups. Examples of $R_3$ heterocyclic groups are pyridyl, substituted pyridyl; e.g., chloropyridyl, methylethylpyridyl, methylpyridyl, 2-chloro-4-methylpyridyl, bromopyridyl, 2,4,6-trimethylpyridyl, dimethylpyridyl, and the N-oxides; e.g., pyridyl-N-oxide, methylpyridyl-N-oxide, and the like.

Useful $R_3$ carbocyclic aryl groups include phenyl groups and fused ring groups such as naphthyl, tetrahydronaphthyl, indanyl, and the like.

Preferred $R_3$ carbocyclic aryl groups are those having the formula:

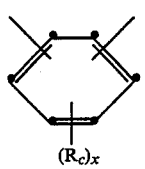
II where x is 0, 1, 2, 3, or 4 and $R_c$ includes alkyl groups, both linear and branched, preferably $C_1-C_4$ alkyl groups, $C_3-C_6$ cycloalkyl groups, halogen such as Cl, I, Br or F, alkoxy preferably $C_1-C_4$ alkoxy, hydroxy, nitro, cyano, carbamoyl, $N-C_1-C_6$-alkyl- and $N,N$-di-$C_1$-C-hd 6-alkylcarbamoyl, and the like. Examples of suitable preferred carbocyclic aryl groups of Formula II are phenyl, tetrahydronaphthyl, fluorophenyl, dibromophenyl, trichlorophenyl, iodophenyl, hydroxyphenyl, tolyl, cresyl, nitrophenyl, carboxyphenyl, methoxyphenyl, cyclohexylphenyl, aminophenyl, dimethylchlorophenyl, butoxyphenyl, dichlorophenyl, cyanophenyl, nitrophenyl, tetramethylphenyl, dimethylphenyl, carbamoylphenyl, N,N-dimethylcarbamoylphenyl and the like.

An especially preferred $R_3$ group is the carbocyclic group having the formula

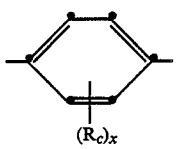
IIA

A more preferred $R_3$ carbocyclic group is Formula IIA where x is 0, 1 or 2. A most preferred carbocyclic group is.

$R_4$ includes the hydroxy group and the ester group

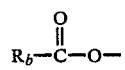

where $R_b$ is $C_1-C_6$ alkyl such as methyl, isopropyl, butyl, hexyl, ethyl, and the like. Compounds where $R_4$ is OH are preferred.

The $R_5$ and $R_6$ groups are hydrogen or alkyl groups. The alkyl groups preferably have from 1-6 alkyl carbon atoms and may be branched, linear, or cyclic; substituted or unsubstituted. Examples of suitable alkyl groups are methyl, n-hexyl, isopropyl, 2,2,4-trimethyl-N-butyl, cyclopropyl, cyclohexyl, chlorobutyl, tert-butyl,

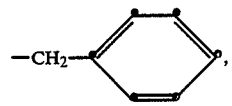

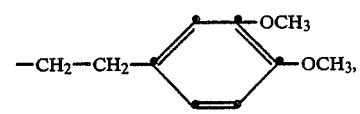

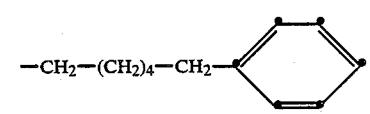

and the like. The $R_5$ and $R_6$ groups may also be joined to form a 5-6 membered N-alicyclic ring such as

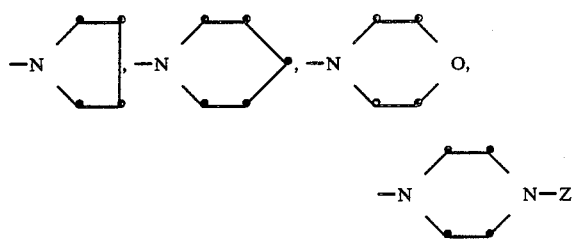

where Z is H or $C_1-C_{10}$ alkyl, and the like.

It is preferred that one of $R_5$ and $R_6$ is hydrogen while the other is $C_{1-6}$ alkyl, and preferably $C_3-C_4$ branched hydrocarbon alkyl.

Compounds of formula I which are preferred are those in which R is hydrogen, represented by the formula

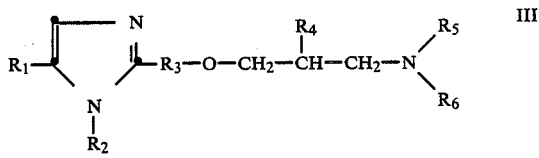
III

Another series of preferred compounds are those wherein R and $R_2$ is each hydrogen. These compounds have the formula

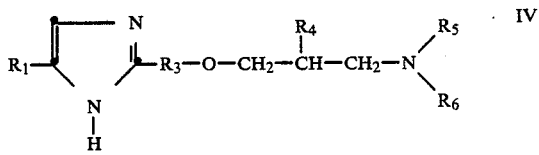
IV

When $R_2$ is hydrogen, the 4 and 5 positions in the imidazole are substantially equivalent.

A more preferred series of compounds is that of formula IV where $R_1$ is selected from hydrogen, trihaloalkyl, preferably $-CF_3$, cyano, $-CH_3$, phenyl, substituted phenyl having 1-5 substituents preferably selected from halogen (Cl, Br, F), and heterocyclic group such as thienyl, furyl, methylpyridyl, pyridyl, pyridyl-N-oxide and the like.

Another more preferred series of compounds is that having the formula

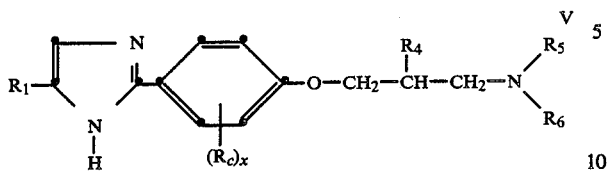

where $R_1$ is selected from —$CH_3$, H, phenyl, pentafluorophenyl, p-chlorophenyl, p-fluorophenyl, p-methoxyphenyl, 2-thienyl, —$CF_3$— and pyridyl; x is 0, 1, 2, or 3 and Rc is halo preferably chloro, $C_1$–$C_3$ alkyl preferably —$CH_3$, and cyano.

Another series of preferred compounds are those having the formula V where $R_4$ is —OH.

In a particularly preferred series of compounds having formula V, $R_4$ is OH and only one of $R_5$ and $R_6$ is $C_1$–$C_6$alkyl, preferably cyclic or branched $C_3$–$C_4$ alkyl such as tert-butyl, cyclopropyl, 1-methyl-3-phenylpropyl, 1-methyl-2-phenylethyl and the like.

An especially preferred series of compounds is one having formula V where $R_1$ is —$CF_3$, $R_4$ is OH and one of $R_5$ and $R_6$ is hydrogen while the other is $C_1$–$C_6$ alkyl, preferably $C_3$–$C_4$ cyclic or branched hydrocarbon alkyl, especially tert-butyl.

Another preferred series of compounds of the invention are those having the formula:

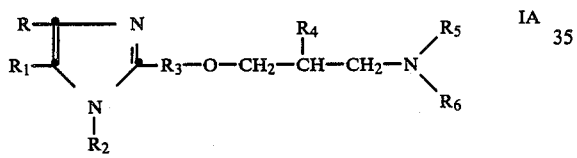

wherein:
R and $R_1$ are independently
(a) hydrogen;
(b) $C_1$–$C_{10}$ linear or branched alkyl;
(c) substituted $C_1$–$C_{10}$ linear or branched alkyl having 1–3 substituents selected from the group consisting of halo (F, Br, Cl), hydroxy, $C_1$–$C_4$alkoxy, morpholino, N-lower$C_{1-4}$ alkyl, piperazino, piperidino, di(lower$C_{1-4}$ akyl)amino;
(d) heteroaryl group having 5–6 ring atoms one of which is an O, N, or S heteroatom provided that one of R or $R_1$ is hydrogen;
(e) unsubstituted or substituted aryl of $C_6$ or $C_{10}$ and the substituents are 1–2 halo or $C_1$–$C_6$ alkoxy groups;
(f) pentafluorophenyl;
(g) $C_{3-10}$ cycloalkyl;
(h) halo;
(i) cyano;
(j) $C_1$–$C_6$ alkanoylamino;
(k) carboxy and carboxy derivatives;
(l)

wherein Ra is hydrogen or $C_1$–$C_6$ alkyl;

(m)

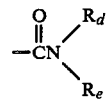

wherein $R_d$ and $R_e$ are independently hydrogen, $C_1$–$C_8$ linear or branched alkyl, $C_6$ or $C_{10}$ unsubstituted or substituted aryl having 1–2 substituents selected from $C_1$–$C_4$ alkyl, halo, $C_1$–$C_4$ alkoxy or hydroxy, or $R_d$ and $R_e$, together with the N atom, can be joined to form a 6-membered heterocyclic ring which can optionally contain an additional O, S, NH, or N-lower $C_1$–$C_8$ alkyl heteroatom;
$R_2$ is
(a) hydrogen;
(b) $C_1$–$C_{10}$ linear or branched alkyl;
(c) $C_3$–$C_6$ alkenyl;
(d) hydroxy -$C_1$–$C_{10}$ linear or branched alkyl;
$R_3$ is
(a) naphthyl;
(b) tetrahydronaphthyl;
(c) indanyl;
(d)

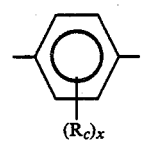

wherein
$R_c$ is hydrogen; halo; $C_1$–$C_4$– linear or branched alkyl; $C_1$–$C_4$ alkoxy; hydroxy; cyano; phenyl;
X is 0–4;
$R_4$ is
(a) hydroxy;
(b)

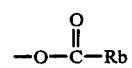

wherein Rb is $C_1$–$C_6$ linear or branched alkyl;
$R_5$ and $R_6$, when separate, are independently
(a) hydrogen,
(b) $C_1$–$C_6$ linear or branched alkyl;
(c) substituted linear or branched $C_1$–$C_6$ alkyl and the substituent is hydroxy or $C_1$–$C_8$ alkoxy;
(d) monosubstituted $C_1$–$C_6$ linear or branched alkyl and the substituent is pyridyl, substituted or unsubstituted phenyl wherein the substituent is 1–2 methoxy groups, $C_1$–$C_4$ alkylthio, $C_1$–$C_4$ alkylsulfoxide, $C_1$–$C_4$ alkylsulfone provided that one of $R_5$ or $R_6$ is hydrogen;
(e) alkylureido alkyl of $C_2$–$C_8$ wherein the ureido has the formula:

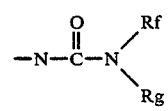

wherein;

Rf and Rg can independently be hydrogen; $C_1-C_8$ alkyl optionally substituted with hydroxy or $C_1-C_8$ alkoxy; unsubstituted or substituted aryl of $C_6$ or $C_{10}$ having 1-2 substituents selected from halo, $C_1-C_4$ alkoxy, or $C_1-C_4$ alkyl; unsubstituted or substituted aralkyl wherein the alkyl is $C_1-C_8$ linear or branched and the aryl is $C_6$ having 1-2 substituents selected from $C_1-C_8$ alkoxy, hydroxy, halo, or $C_1-C_8$ alkyl; or Rf and Rg together with the N atom can be joined to form a 6-membered heterocyclic ring which can optionally contain an additional O, S, NH or N-lower $C_1-C_8$ alkyl heteroatom;

(f) unsubstituted or substituted aryl of $C_6-C_{10}$ wherein the substituents are 1-2 $C_1-C_4$ alkyl groups;

(g) $C_3-C_6$ cycloalkyl;

(h)

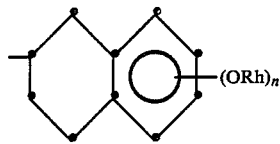

wherein Rh is $C_1-C_4$ alkyl and n is 0, 1, or 2;

$R_5$ and $R_6$ when joined together with the N atom form:

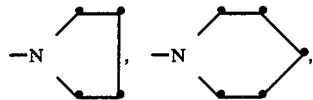

(a)    (b)

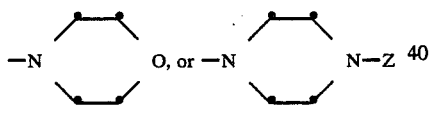

(c)    (d)

wherein Z is hydrogen or $C_1-C_{10}$ linear or branched alkyl.

Within this group of preferred compounds are those wherein $R_2$, $R_3$, $R_4$ and $R_5$ and $R_6$ when joined are as defined above and R and $R_1$ are independently
(a) hydrogen;
(b) chlorine;
(c) bromine;
(d) methyl;
(e) t-butyl;
(f) isopropyl;
(g) pyridinyl;
(h) furanyl;
(i) thienyl;
(j) methoxyphenyl;
(k) chlorophenyl;
(l) fluorphenyl;
(m) dichlorophenyl;
(n) hydroxymethyl;
(o) carboethoxy;
(p) $CH_3CONH-$;
(q) $CH_3OCH_2-$;
(r) $CH_3CH_2OCH_2-$;
(s) $CH_3OCH_2CH_2-$;
(t)

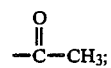

(u)

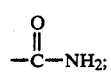

(v)

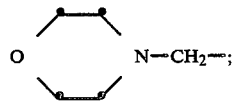

and,
(w) $C_6H_5$;
(x) $CF_3$;
(y) CN;
(z) $CO_2CH_3$;
(aa) pentafluorophenyl; and, $R_5$ and $R_6$ are independently
(a) hydrogen;
(b) cyclopropyl;
(c) isopropyl;
(d) n-propyl;
(e) t-butyl;
(f)

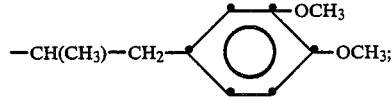

(g) 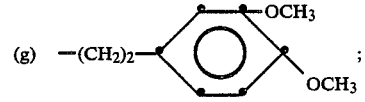

(h) 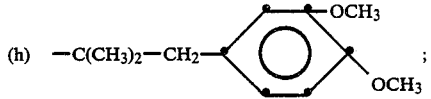

(i) 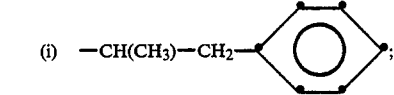

(j) 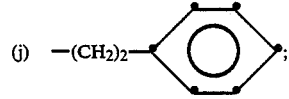

(k) 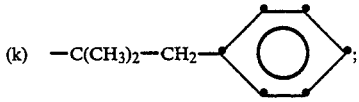

-continued (l) 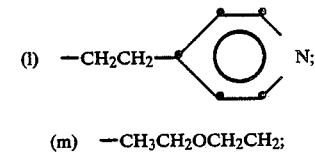

(m) —CH₃CH₂OCH₂CH₂;

(n) 

(o) 

(p) 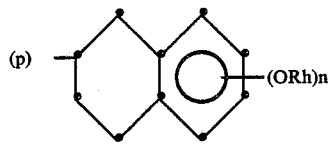

wherein Rh is methyl and n is 2.

An especially desirable group of compounds are those in which the compound is of the formula

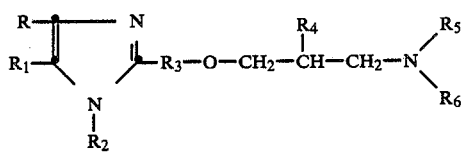

wherein:
R and R₁ are independently selected from:
(a) hydrogen;
(b) C₅–C₁₀ linear or branched alkyl;
(c) substituted C₁–C₁₀ linear or branched alkyl having 1–3 substituents selected from the group consisting of fluoro, bromo, chloro, hydroxy, C₁–C₄ alkoxy, morpholino, di(C₁–C₄ alkyl)amino;
(d) unsubstituted or substituted aryl of C₆ or C₁₀ and the substituents are 1–2 halo or C₁₋C₆ alkoxy group;
(e) pentafluorophenyl;
(f) halo (fluoro, chloro, bromo);
(g) carboxy and carbalkoxy;
(h)

wherein $R_a$ is hydrogen or C₁–C₆ alkyl, and;
(i)

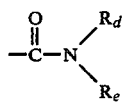

wherein $R_d$ and $R_e$ are hydrogen C₁–C₈ linear or branched alkyl, C₆ or C₁₀ unsubstituted or substituted aryl having 1–2 substituents selected from C₁–C₄ linear or branched alkyl, halo, alkoxy or hydroxy;
(j) C₁–C₆ alkanoylamino provided that at least one of R and R₁ is selected from (b) to (j);
(a) hydrogen;
(b) C₁–C₁₀ linear or branched alkyl;
R₃ is

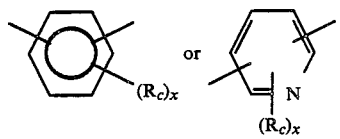

wherein $R_c$ is
(a) hydrogen;
(b) halo;
(c) C₁–C₄ alkyl;
(d) C₁–C₄ alkoxy;
(e) hydroxy; x is 0–4;
R₄ is hydroxy;
R₅ and R₆ are independently:
(a) hydrogen;
(b) C₁–C₆ alkyl;
(c) C₁–C₆ substituted alkyl wherein the substituent is selected from alkoxy, methoxyphenyl or dimethoxyphenyl; provided that at least one of R₅ and R₆ is a substituent selected from (b) and (c), and provided that when R₃ is

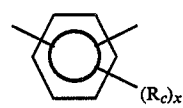

and R₆ is (b), R is selected from (d)–(j) inclusive, and when R₃ is

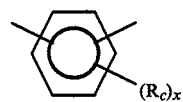

and R₆ is (c), R is selected from (c)–(j) inclusive; or a pharmaceutically acceptable acid addition salt or a quaternary ammonium salt thereof.

The compounds of the present invention also include the non-toxic pharmacologically acceptable acid addition and quaternary ammonium salts of the present imidazoles. The acid addition salts are prepared by treating the imidazole with an appropriate amount of a suitable organic or inorganic acid. Examples of useful organic acids are carboxylic acids such as maleic acid, tartaric acid, acetic acid, pamoic acid, oxalic acid, propionic acid, salicyclic acid, succinic acid, citric acid, malic acid, isethionic acid, and the like; useful inorganic acids are hydrohalo acids such as HCl, HBr and HI, sulfuric acid, H₃PO₄, and the like.

The quaternary salts are characterized by the group

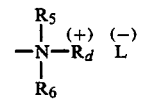

wherein R₅ and R₆ are C₁–C₆ alkyl, $R_d$ is C₁–C₆ alkyl and L is the anion of a non-toxic acid, preferably a halide such as the iodide. These salts are prepared by any suitable method, for example, by reacting any imidazole of the present invention having the tertiary amine group

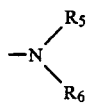

with an alkyl halide, preferably the iodide such as ethyliodide or methyliodide, in a suitable solvent such as methanol, ethanol or dimethylformamide (DMF). The reaction is generally carried out at room temperature. The quaternary salt is obtained directly on removing the solvent.

Compounds of the present invention may be prepared by any convenient method.

An especially useful method of preparing imidazoles of the present invention wherein $R_4$ is -OH is by reaction of ammonia or a suitable amine reactant with an epoxy compound as illustrated by the following general reaction equation:

METHOD A

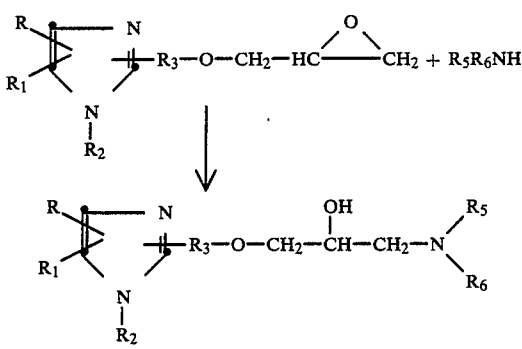

The reaction is generally carried out in solution with excess amine reactant serving as the solvent. However, other solvents may be used such as triethylamine, pyridine, tetrahydrofuran, and the like. The reaction is conveniently conducted at reflux temperature. However, the reaction temperature can be varied from room temperature to temperatures above reflux. The reaction may be carried out at atmospheric pressure but it can be carried out at pressures above atmospheric, if desired.

Another method for preparing compounds of Formula I where $R_2$ is H and

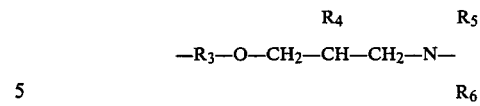

is the 2 position in the imidazole is by the reaction of aryl aldehyde with a glyoxal or acetal thereof and $NH_3$. When the acetal is used, it must first be hydrolyzed; e.g. by treatment with a strong acid solution such as aqueous $H_2SO_4$. This reaction is illustrated by the following equations:

METHOD B

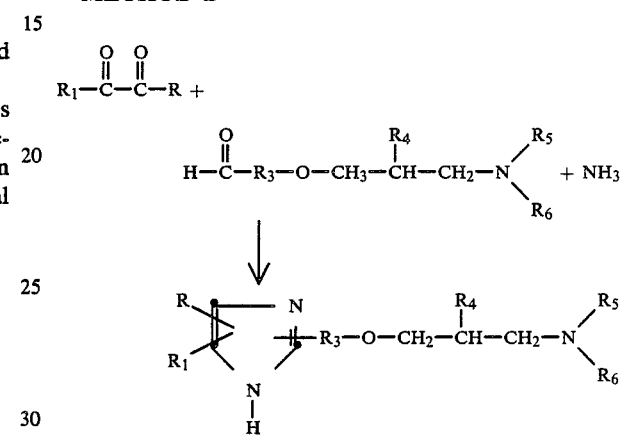

If, in Method B, the aryl aldehyde used has the formula

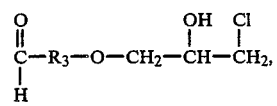

the imidazole product would require dehydrochlorination and treatment with amine, to afford the imidazole of the present invention.

The process of Method B is generally carried out in solution and at temperatures ranging from about room temperature to about 100° C. Pressure is not required. Solvents used will vary depending on the type of reactants used. Generally, this reaction is carried out in an aqueous solution; e.g., $H_2O$ or $H_2O$/miscible alkanol.

Aryl aldehydes can also be prepared by reacting an aryl aldehyde with an oxazolidine as illustrated by the following equations:

METHOD C

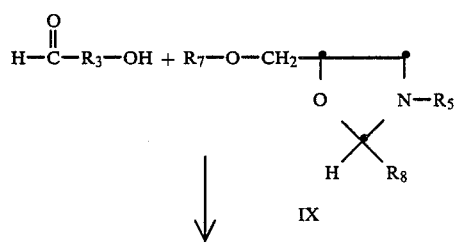

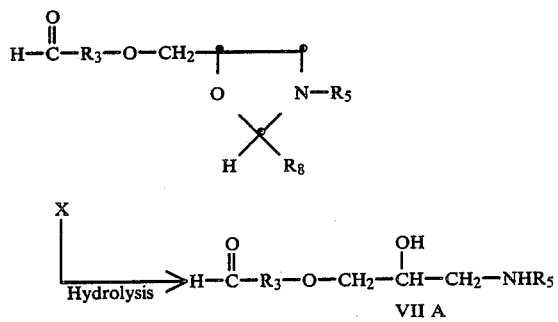

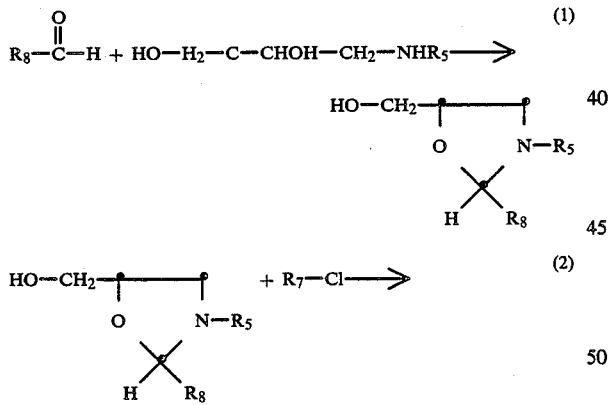

$R_8$ is the residue of an aldehyde as will be described below. $R_7$ is an alkyl or aryl sulfonyl groups; e.g., benzene sulfonyl, toluene sulfonyl, methane sulfonyl, and the like. This coupling reaction of the oxazolidine IX and the aryl aldehyde is generally carried out in suitable solvent such as dimethylformamide (DMF), dimethylsulfoxide (DMSO), hexamethylenephosphoramide (HMPP), alkanals such as methanol, ethanol, and the like. While the reaction can be carried out at temperatures ranging from 0° C. to 200° C., it is conveniently carried out at the reflux temperature of the solution. Conventional techniques and reagents; e.g., HCl, $H_2SO_4$, are used to effect the hydrolysis.

The oxazolidine IX is obtained from the reaction of an aldehyde with a 1-amino-2,3-dihydroxypropane followed by treatment with an appropriate alkyl or aryl sulfonyl halide. This reaction is illustrated by the following equations:

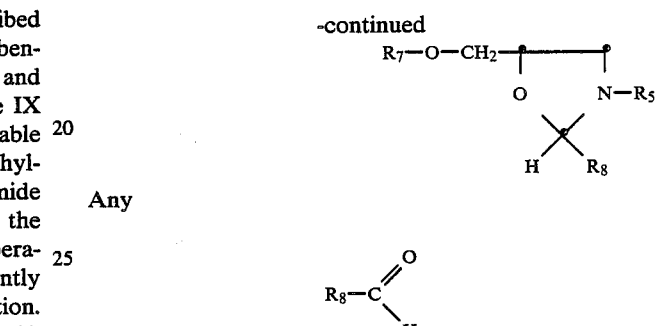

Any

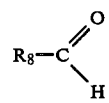

aldehyde may be used provided that it does not adversely affect the oxazolidine preparation. Examples of suitable aldehydes are aryl aldehydes such as benzaldehyde, substituted benzaldehydes, naphthylaldehyde, and the like, and alkanals such as acetaldehyde, formaldehyde, butyraldehyde, and the like. Commercially available aldehydes are most conveniently used. Processes for preparing oxazolidines are disclosed in U.S. Pat. Nos. 3,718,647 and 3,657,237 and to the extent necessary, the pertinent disclosure is incorporated herein by reference.

Compounds of formula I wherein the

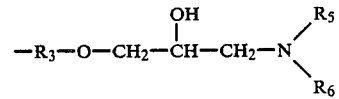

is in the 4-position in the imidazole ring can be prepared according to the method illustrated by the following equations:

METHOD D

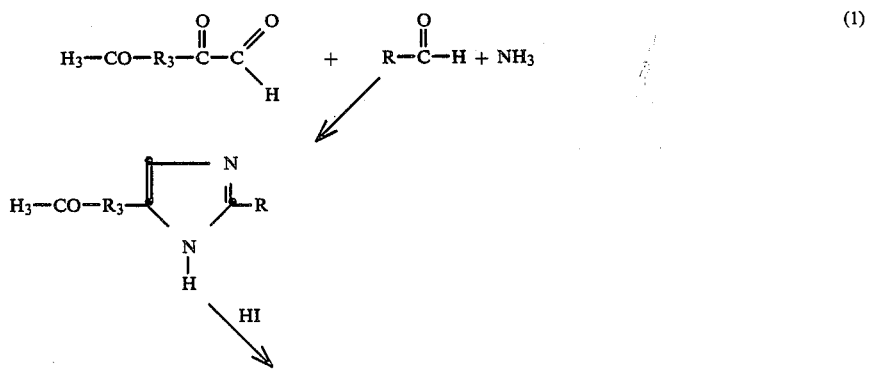

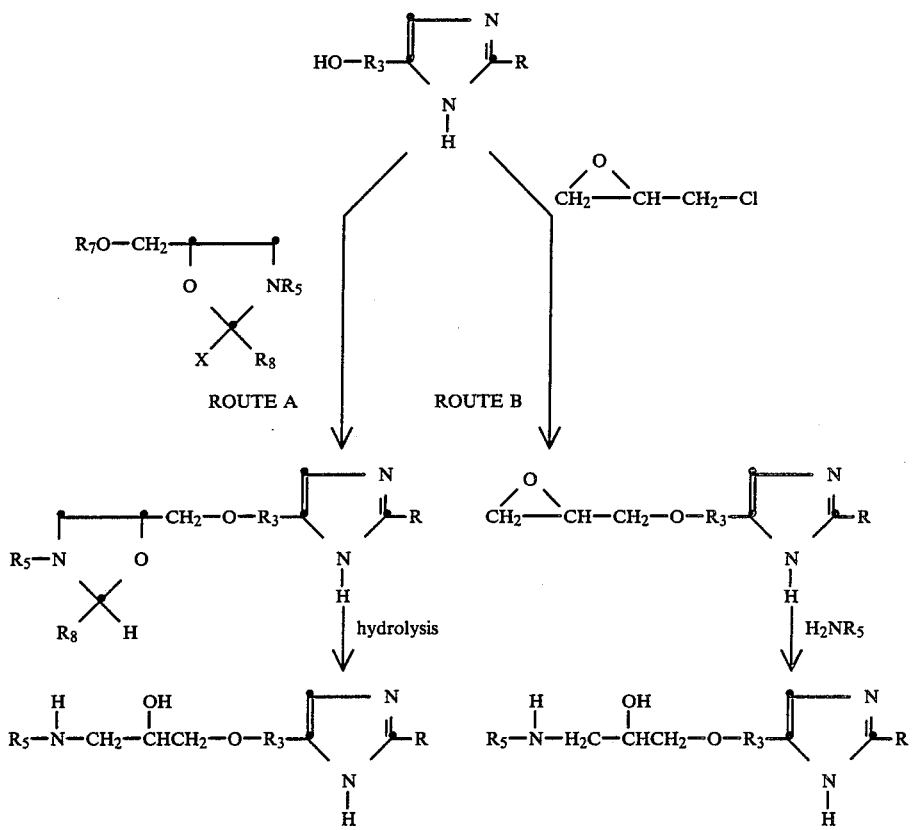

Method D, as the equation illustrates, involves the reaction of alkoxyarylglyoxal with an aldehyde in the presence of ammonia. This ammonia may be liquid ammonia wherein the reaction temperature would range from about −33° C. up to about 70° C., the reaction being carried out under pressure where the temperature requires. The ammonia may also be provided as aqueous solution; i.e., ammonia hydroxide, in which case reaction temperatures of from about the freezing point of the reaction mixture to about 100° C. can be used. With the aqueous ammonia system, room temperature is conveniently used. Other water miscible aqueous solvents such as the lower alkanol; e.g., CH$_3$OH, or DMF may also be used as necessary. The ether cleavage may be accomplished using any suitable reagents and procedure such as aqueous HI or aqueous HBr; or AlCl$_3$ in a hydrocarbon solvent (hexane, benzene, etc.). The Method D, Route A of course permits preparation of a single optical isomer while Route B results in a racemate.

Following are additional methods for preparing the compounds of the invention.

METHOD E

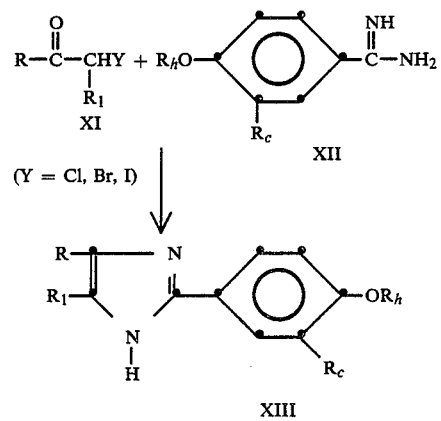

In Method E, α-haloketone XI is reacted with suitably protected amidine XII (e.g., R$_c$=halo, alkyl, alkoxy; R$_h$=methyl, benzyl, or other ether protecting groups, etc.) in a suitable solvent such as chloroform, acetonitrile, tetrahydrofuran (THF), methylene chloride, acetone, and the like, at about 0° C. to the reflux temperature of the solvent for about 1–48 hours to produce phenoxy substituted imidazole intermediate XIII which can then be used to prepare the imidazole compounds of the invention.

METHOD F

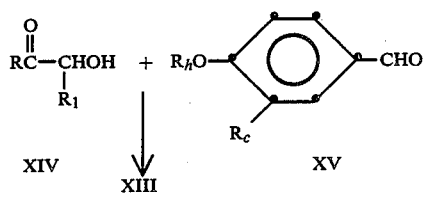

Method F illustrates another route for obtaining intermediate XIII employing the classically known Weidenhagen synthesis. In this method, α-hydroxyketone XIV is reacted with aldehyde XV in the presence of ammonia and cupric acetate reagent and a suitable solvent (e.g., liquid ammonia, aqueous or liquid ammonia-methanol, alkanols, THF, dimethylformamide (DMF), acetonitrile) at a temperature of about 20° C. to the reflux temperature of the solvent for about 1–24 hours to obtain intermediate XIII. When the reagent employed is cupric acetate, a cuprous salt of XIII is first formed which can then be converted to XIII upon treatment with hydrogen sulfide.

METHOD G

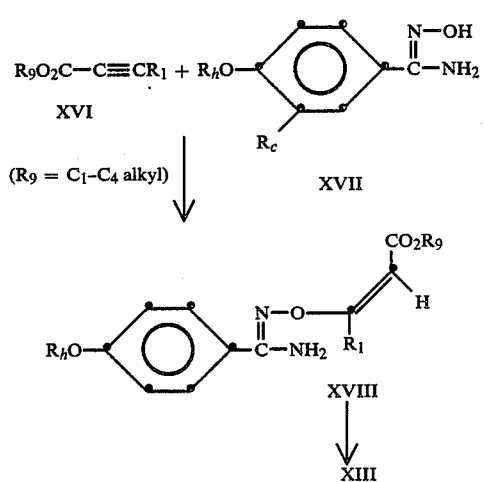

Method G illustrates still another means for obtaining intermediate XIII. In this method, substituted propriolate ester XVI is reacted with amidoxime XVII in a suitable solvent (e.g., alcohol, acetonitrile, THF, dimethylsulfoxide (DMSO), acetone, DMF) at about 0° C. to the reflux temperature of the solvent for about 1–48 hours to obtain olefin XVIII wherein when $R_1=H$, a mixture of cis and trans isomers is obtained, and when $R_1$=alkyl or aryl, a mixture of E and Z isomers is obtained. Further treatment of olefin XVIII in solvents such as DMF, DMSO, diphenylether, xylene, and the like, at 0° C. to the reflux temperature of the solvent for about 1–48 hours affords intermediate XIII, preferably for 1 hour in diphenylether at 180°–200° C.

METHOD H

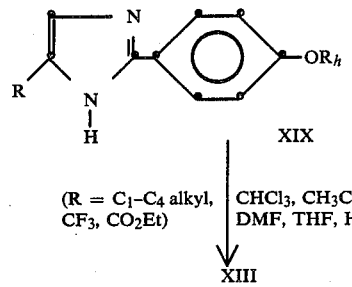

Method H illustrates another route to obtain intermediate XIII by means of halogenation or nitration. In this method, imidazole XIX in a suitable solvent is treated with an electrophile (e.g., $Br_2$, $Cl_2$, N-chlorosuccinimide, N-bromosuccinimide, $KClO_3$, NaOCl, ClCN, BrCN, $C_5H_5$—N—$HBr_3$, NaOCl, $HNO_3$, and the like) at about 0° C. to the reflux temperature of the solvent for about 15 minutes to 24 hours to afford intermediate XIII.

METHOD I

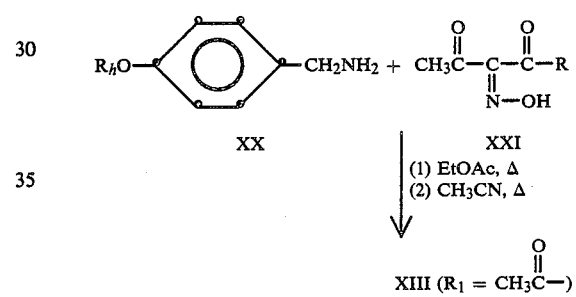

In Method I, intermediate XIII is obtained by first heating benzylamine derivative XX with the oxime of 2,4-dicarbonyl XXI in ethylacetate at reflux for about 2 hours followed by heating the mixture in acetonitrile at reflux for about an additional 19 hours from which intermediate XIII is recovered.

METHOD J

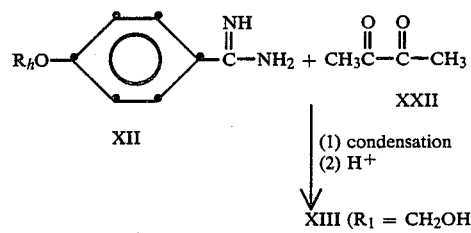

Method J illustrates yet another route for obtaining intermediate XIII wherein amidine XII is first condensed with glyoxal XXII to obtain an imidazoline intermediate which is then treated with an acid to afford intermeidate XIII.

METHOD K

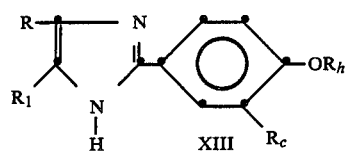

XIII

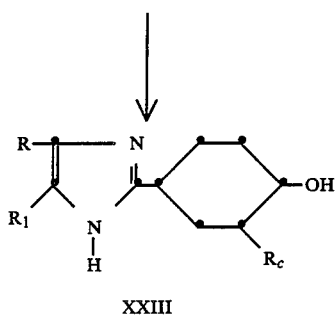

XXIII

In Method K, phenol substituted imidazole XXIII can be obtained from imidazole intermediate XIII when $R_h$=alkyl by treating intermediate XIII with a suitable reagent such as 48% HBr-AcOH, 48% HBr, HF, AlCl₃, BBr₃, and the like, at a temperature of about 0° C. to the reflux temperature of the reagent. When the reagent is the reagent-solvent mixture: 48% HBr-AcOH, treatment at reflux for about 5 hours provides compound XXIII. When the reagent employed is BBr₃, a suitable solvent such as methylene chloride is used at a temperature of about —° C. to room temperature for about 12 hours to afford compound XXIII.

Alternatively, compound XXIII can be obtained from intermediate XIII when $R_h$=CH₂C₆H₅ by treating intermediate XIII in a suitable solvent (e.g., alcohol, acetic acid, acetone, and the like) at about room temperature for about 15 minutes to about 15 hours in the presence of a suitable catalyst (e.g., 10% Pd/C) at atmospheric pressure to about 60 psi of H₂ to afford compound XXIII.

METHOD L

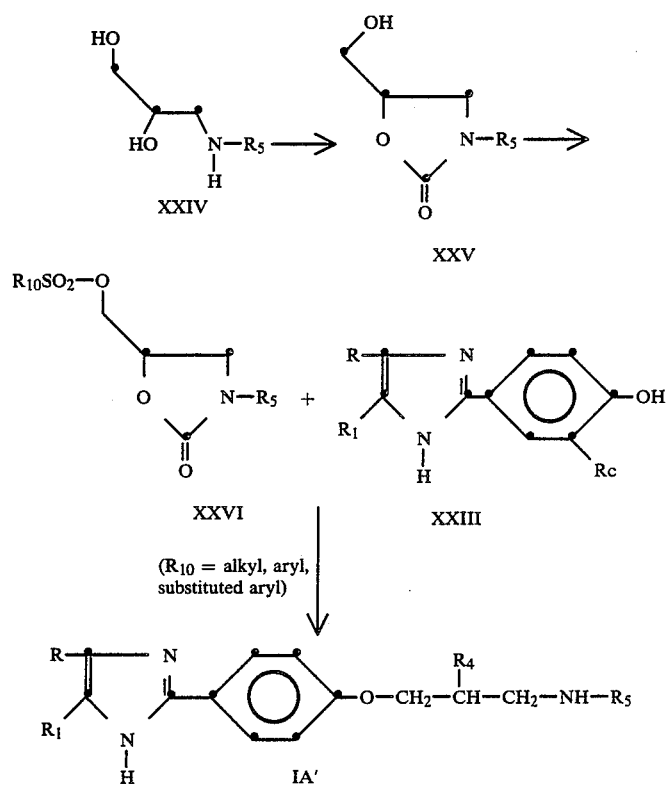

As shown in Method L above, glycolamine XXIV is first converted to oxazolid-2-one XXV which, in turn, is converted to sulfonate oxazolidone XXVI [prepared according to the methods described in Canadian Patent No. 965,787]. Oxazolidone XXVI is then first reacted with phenol substituted imidazole XXIII in the presence of a base (e.g., NaOCH₃, NaOH, K-t-BuO, NaH, and the like) in a suitable solvent (e.g., DMSO, DMF, toluene, methanol, H₂O, and the like) for about 1-48 hours at about 0° C. to the reflux temperature of the solvent. The reaction mixture is then subjected to basic hydrolysis by treating it with, for example, 10% NaOH-:EtOH(1:1) at the reflux temperature of the solvent for about 2 hours to afford an imidazole compound IA' of the invention.

The compounds of the present invention are active (1) as antihypertensives, and/or (2) as β-adrenergic blocking agents. Many of the present imidazoles also are active vasodilators.

The antihypertensive effect was determined by administering (orally or intraperitoneally) the present compounds to spontaneously hypertensive (SH) rats and measuring the effect on the blood pressure. Representative imidazoles, generally administered as salts;

e.g., the hydrochloride, were found to lower the SH rats' blood pressure.

The β-adrenergic blocking activity (β-blockade) of the present compounds was determined by measuring the ability of representative compounds to block isoproterenol induced tachycardia, vasodepression and bronchodilatation in animals. Intravenous administration of the imidazole, (generally as an acid addition salt) was used for this evaluation. Representative imidazoles showed ability to effect β-blockade in addition to having the aforesaid antihypertensive effect of immediate onset.

The in vitro β-adrenergic blocking effectiveness of the compounds of the invention was also evaluated as follows:

The interaction with the $β_1$-receptor was determined via inhibition of the positive chronotropic actions of isoproterenol in isolated guinea pig atrial preparations. $β_2$ potency was determined by using isolated guinea pig tracheal chains contracted with $PGF_{2α}$ and measuring inhibition of isoproterenol-induced relaxation.

Representative compounds of the invention which were tested and found to have β-adrenergic blocking activity are listed below in Table I.

TABLE I

Representative Compounds of Formula IA Which Exhibited Antihypertensive and β-Adrenergic Blocking Activity $$\begin{array}{c} R \\ R_1 \end{array} \!\!\! = \!\!\! \begin{array}{c} N \\ \\ N \\ | \\ R_2 \end{array} \!\!\! R_3-O-CH_2-\overset{R_4}{\underset{|}{CH}}-CH_2-N\!\!\!\begin{array}{c} R_5 \\ \\ R_6 \end{array}$$

$(R_2 \neq H; R_4 = OH)$    IA

| | R | $R_1$ | $R_3$ | $R_5$ | $R_6$ |
|---|---|---|---|---|---|
| (1) | H | F₃C— | —phenyl— | H | —C(CH₃)₃ |
| (2) | " | " | " | —CH₃ | —CH₃ |
| (3) | " | " | " | " | —(CH₂)₂—phenyl |
| (4) | " | " | " | H | —CH(CH₂)(CH₂) (cyclopropyl) |
| (5) | " | " | —(methylphenyl)— | " | —C(CH₃)₃ |
| (6) | H | H₂NCO— | —phenyl— | H | —(CH₂)₂—(3,4-dimethoxyphenyl) |
| (7) | " | morpholino-CH₂— | " | " | " |
| (8) | " | Br | —(chlorophenyl)— | " | " |
| (9) | " | H₃C—C(=O)— | —phenyl— | " | " |

TABLE I-continued
Representative Compounds of Formula IA Which Exhibited Antihypertensive and β-Adrenergic Blocking Activity $$\underset{R_1}{\overset{R}{\diagdown}}\!\!=\!\!\underset{\underset{R_2}{|}}{\overset{N}{\diagup}}\!\!R_3\!-\!O\!-\!CH_2\!-\!\underset{R_4}{\overset{|}{C}H}\!-\!CH_2\!-\!\underset{R_6}{\overset{R_5}{N\diagdown}}$$

($R_2 \neq H$; $R_4 = OH$)     IA

| | R | R$_1$ | R$_3$ | R$_5$ | R$_6$ |
|---|---|---|---|---|---|
| (10) | " | H | " | " | $-CH_2CH_2NH-\overset{O}{\overset{\|}{C}}-NH-C_6H_5$ |
| (11) | " | H$_3$COCH$_2$ | " | " | $-(CH_2)_2-C_6H_3(OCH_3)_2$ |
| (12) | " | CH$_3$CH$_2$OCH$_2-$ | " | " | " |
| (13) | " | (CH$_3$)$_2$CH$-$ | " | " | $-CH(CH_3)_2$ |
| (14) | H$_3$COCH$_2$ | CH$_3-$ | " | " | $-(CH_2)_2-C_6H_3(OCH_3)_2$ |
| (15) | H | H$_3$CO(CH$_2$)$_2$ | " | " | " |
| (16) | H | (2-methylthiophen-3-yl) | " | " | 6,7-dimethoxynaphthyl |
| (17) | H | H$_3$C$-\overset{O}{\overset{\|}{C}}-$ | phenyl | " | $-C(CH_3)_3$ |
| (18) | " | F$_3$C$-$ | 2,6-dimethylphenyl | " | " |
| (19) | " | H | phenyl | " | " |
| (20) | " | NC$-$ | " | " | " |
| (21) | " | F$_3$C | phenyl | " | " |

TABLE I-continued
Representative Compounds of Formula IA Which Exhibited Antihypertensive and β-Adrenergic Blocking Activity $$\text{R–C(R}_1\text{)=N–C(R}_3\text{–O–CH}_2\text{–CH(R}_4\text{)–CH}_2\text{–N(R}_5\text{)(R}_6\text{)}$$
with N–R₂ ring; (R₂ ≠ H; R₄ = OH) — Formula IA

| | R | R₁ | R₃ | R₅ | R₆ |
|---|---|---|---|---|---|
| (22) | " | " | phenyl (2-substituted) | " | " |
| (23) | " | " | 3,4-dichlorophenyl | " | " |
| (24) | " | " | phenyl | " | " |
| (25) | " | " | 4-chlorophenyl (S)-ISOMER | " | " |
| (26) | " | 2-thienyl | phenyl | " | (CH₂)₂OCH₂CH₃ |
| (27) | " | HOCH₂ | " | " | —(CH₂)₂-(3,4-dimethoxyphenyl) (OCH₃, OCH₃) |
| (28) | " | Br | " | " | " |
| (29) | " | Cl | phenyl | " | " |
| (30) | " | EtO₂C | " | " | " |
| (31) | " | 2-thienyl | 2-methylphenyl (CH₃) | " | " |
| (32) | " | " | 2-chlorophenyl (Cl) | " | " |

TABLE I-continued

Representative Compounds of Formula IA Which Exhibited Antihypertensive and β-Adrenergic Blocking Activity $$R_1\text{-C(R)=N-C(R_3-O-CH_2-CH(R_4)-CH_2-N(R_5)(R_6))-N(R_2)}$$ (IA)

($R_2 \neq H$; $R_4 = OH$)

| # | R | $R_1$ | $R_3$ | $R_5$ | $R_6$ |
|---|---|---|---|---|---|
| (33) | " | " | Br-phenyl | " | " |
| (34) | Br | $CH_3-$ | phenyl | " | " |
| (35) | Cl | " | " | " | " |
| (36) | $CH_3-C(=O)-NH-$ | " | " | " | " |
| (37) | $CH_3-C(=O)-$ | " | " | " | " |
| (38) | H | $(CH_3)_2CH-$ | " | " | " |
| (39) | $-CH_3$ | $-CH_3$ | " | " | " |
| (40) | H | $(CH_3)_3C-$ | " | " | " |
| (41) | " | 2-methylthiophene | " | " | $-CH(CH_3)-(CH_2)_2-\text{phenyl}$ |
| (42) | " | " | " | " | $-CH(CH_2-CH_2)$ (cyclopropyl) |
| (43) | " | " | " | " | $-(CH_2)_2CH_3$ |
| (44) | " | " | " | " | $-(CH_2)_2-NH-C(=O)-NH-n\text{-Bu}$ |
| (45) | " | $CH_3$ | $OCH_3$-phenyl | " | $-(CH_2)_2-\text{phenyl}(OCH_3)(OCH_3)$ |

In evaluating the β-blocking effectiveness of the present compounds, it was noted that many of the compounds exhibit some cardioselectivity that is the compound is more effective in reducing the heart rate effects of isoproterenol than it is in blocking the isoproterenol effects on the bronchi. Expressed in different terms, a smaller amount of the compound is required to block isoproterenol-induced elevation in heart rate than is required to block the isoproterenol-induced relaxation of the bronchi. This cardioselectivity factor can be expressed as the ratio of $ED_{50}$ for pulmonary effect $(\beta_2)$:$ED_{50}$ for cardiac effect $(\beta_1)$. Where the $\beta_2$:$\beta_1$ ratio is over 1, then the compound would be considered to have cardioselective activity. The tested 6-16 & 26-45 compounds above are examples of compounds having $\beta_2$:$\beta_1$ ratios greater than 1.

The β-adrenergic blocking effectiveness of the compounds of the present invention indicates that they are also useful to treat humans suffering from undesirable conditions such as hypertension, angina pectoris or certain arrhythmias which are known to be amenable to treatment with β-adrenergic blocking agents. Thus, the compounds of the invention are useful as antihypertensive, cardioprotective, antiarrhythmic, and antianginal agents. Furthermore, the cardioselective nature of some of the present compounds offers the advantage of limiting blockade to only the $\beta_1$ receptors, i.e., those which control heart rate. Thus, these $\beta$-blocking agents are also useful to control tachycardia which may be drug induced (as by isoproterenol) or brought about by physiological conditions, reduce intraocular pressure in the treatment of glaucoma, and inhibit renal renin secretion.

For use as antihypertensives and/or $\beta$-adrenergic blocking agents, the present compounds can be administered orally, transdermally or parenterally; i.e., intravenously, interperitoneally, etc. and in any suitable dosage form. The compounds may be offered in a form (a) for oral administration; e.g., as tablets, in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for parenteral administration; e.g., dissolved or dispersed in a suitable liquid carrier or emulsified, or (c) as an aerosol. The ratio of active compound to compounding ingredients; i.e., carrier, diluent, etc., will vary as the dosage form requires. Whatever dosage form is used, the amount of compound of the present invention administered should be sufficient to effect (a) a reduction in blood pressure of the patient suffering from hypertension and/or (b) desirable level of $\beta$-blockade in the patient. Generally, doses of the present compounds of from about 0.01 to about 50 mg/kg and preferably from about 0.1 to about 20 mg/kg of body weight per day may be used. Dosage may be single or multiple depending on the daily total required and the unit dosage.

Following are examples illustrating representative pharmaceutical formulations containing imidazoles of the present invention. Conventional techniques are used to prepare these formulations

| INGREDIENT | AMOUNT (Mg.) |
| --- | --- |
| TABLET FORMULATION | |
| (S)-4-Bromo-2-{p-[3-(3,4-dimethoxy-phenylethylamino)-2-hydroxypropoxy]phenyl}imidazole dihydrochloride hemihydrate | 40.0 |
| calcium phosphate | 120.0 |
| lactose | 50.0 |
| starch | 23.5 |
| magnesium stearate | 1.5 |
| CAPSULE FORMULATION | |
| (S)-4-Acetyl-2-{4-[3-(3,4-dimethoxy-phenethylamino)-2-hydroxypropoxy]phenyl}imidazole | 250 |
| lactose, U.S.P. | 93 |
| talc | 7 |
| LIQUID SUSPENSION | |
| 2-{4-[3-[[2-(3,4-dimethoxyphenyl)ethyl]]amino]-2-hydroxypropoxy}phenyl-4-(methoxymethyl)imidazole dihydrochloride | 5.0 |
| Veegum H.V. | 3.0 |
| methyl parable | 1.0 |
| kaolin | 10.0 |
| glycerin | 250.0 |
| water, q.s. 1 liter | |

The following examples illustrate preparation of representative imidazoles of the present invention. Unless otherwise indicated, all parts and percentages are by weight, all temperatures are in degrees Celsius, and all analyses were computed to within 0.4%.

EXAMPLE 1

Step A: Preparation of
3-(3-Chloro-2-hydroxypropoxy)Benzaldehyde

A mixture of m-hydroxybenzaldehyde (24.4 g.), epichlorohydrin (55.2 g.), a pyridine (0.4 ml.) is heated 5 hours at 100° C. and then concentrated under reduced pressure (20 mm. Hg.) over steam. The residual oil is taken up in chloroform (200 ml.), concentrated hydrochloric acid (50 ml.) is added, and the mixture is stirred 0.5 hours at room temperature. The chloroform layer is separated, washed with water, and the chloroform removed under reduced pressure (20 mm. Hg.) over steam. Distillation of the residual oil yields 28.9 g. of 3-(3-chloro-2-hydroxypropoxy)-benzaldehyde as a yellow-brown oil, b.p. 166° C./0.25 mm. Hg.

Step B: Preparation of
2-[3-(3-Chloro-2-hydroxypropoxy)phenyl]-4-trifluoromethylimidazole To a solution of sodium acetate trihydrate (11.6 g.) in water (40 ml.) is added trifluorodibromoacetone (11.6 g.) and the resulting solution is heated 0.5 hours at 100° C. After cooling to room temperature, it is added in one portion to a solution of 3-(3-chloro-2-hydroxypropoxy)-benzaldehyde (9.45 g.) in methanol (100 ml.) and aqueous ammonia 50 ml.). The resulting cloudy solution is allowed to stand 5 hours at room temperature and the methanol is removed under reduced pressure (20 mm Hg.) over steam. An oil separates and crystallizes. The supernatant liquid is decanted and the residue is triturated with benzene and isolated by filtration to yield 6.97 g. of solid. After recrystallization from toluene, the solid is suspended in warm water and acetonitrile added to cause solution. Upon cooling, 2-[3-(3-chloro-2-hydroxypropoxy)phenyl]-4-trifluoromethylimidazole is obtained as a white solid, m.p. 181°-183° C.

Step C: Preparation of
2-[3-(2,3-Epoxypropoxy)-phenyl]-4-trifluoromethylimidazole To a solution of 2-[3-(3-chloro-2-hydroxypropoxy)-phenyl]-4-trifluoromethylimidazole (3.8 g.) in methanol (150 ml.) is added powdered potassium hydroxide (3.g.) and the mixture is allowed to stir 4 hours at room temperature. Glacial acetic acid (2.75 ml.) is added and the mixture concentrated under reduced pressure 920 mm. Hg.) over steam. The resulting residue is stirred with water, filtered and recrystallized from xylene to yield 2.5 g. of 2-[3-(2,3-epoxypropoxy)phenyl]-4-trifluoromethylimidazole is obtained, m.p. 145°-146.5° C.

Step D: Preparation of
2-[3-(3-Isopropylamino-2-hydroxypropoxy)phenyl]-4-trifluoromethylimidazole A solution of 2-[3-(2,3-epoxypropoxy) phenyl]-4-trifluoromethylimidazole (0.9 g.) in isopropylamine (10 ml.) is heated 6 hours at reflux. The excess isopropylamine is removed by distillation at atmospheric pressure over steam. The residue is triturated with nitromethane (5 ml.) and the resulting solid removed by filtration. After recrystallization from nitromethane 0.65 g. of 2-[3-(3-isopropylamino-2-hydroxypropoxy)phenyl]-4-trifluoromethylimidazole is obtained, m.p. 162.5°–163.5° C.

EXAMPLE 2

Preparation of 2-[4-(3-isopropylamino-2hydroxypropoxy)phenyl]-4-trifluoromethylimidazole A solution of 2-[4-(2,3-epoxypropoxy)phenyl]-4-trifluoromethylimidazole (1 g) in isopropylamine (10 ml.) is heated 7 hours at reflux and then allowed to stand 16 hours at room temperature. The excess isopropylamine is removed by distillation at atmospheric pressure and the residue is triturated with nitromethane to yield so solid. After filtration and recrystallization from acetonitrile, 0.6 g. of 2-[4-(3-isopropylamino-2-hydroxypropoxy)phenyl]-4-trifluoro-methylimidazole is obtained, m.p. 173°–173.5° C.

EXAMPLE 3

Step A: Preparation of 2-methyl-4-(2,3-epoxypropoxy)-benzaldehyde

To epichlorohydrin (20 g., 0.216 mole) heated at 55° C. is added dropwise a solution of 2-methyl-4-hydroxybenzaldehyde (9.0 g., 0.006 mole) in 2.5 N sodium hydroxide solution (40 ml.). After the addition, the solution is allowed to stir an additional 3 hours at 55° C. and then at room temperature overnight. the oil is distilled to give 8.3 g. of 2-methyl-4-(2,3-epoxypropyl)benzaldehyde, m.p. 160°–170° C. at 1 mm. Hg.

Step B: Preparation of 2-methyl-4-(3-tert.-butylamino-2-hydroxypropoxy)benzaldehyde To a methyl-4-(2,3-epoxypropoxy)benzaldehyde (8.3 g., 0.043 mole) is added tert-butylamine (10 g., 0.137 mole) and the resulting solution refluxed for 2 hours and allowed to stand overnight at room temperature. The excess tert butylamine is removed under reduced pressure (20 mm. Hg.), the residue is heated on a steam bath with 6 N hydrochloric acid (50 ml.) for 5 hours, and then basified while hot with solid sodium hydroxide. The mixture is cooled to room temperature, extracted with chloroform (3×50 ml.), dried over sodium sulfate, filtered and concentrated to dryness. The residual oil is crystallized from hexane to give 8.75 g. of 2-methyl-4-(3-tert.-butylamino-2-hydroxypropoxy) benzaldehyde, m.p. 82°–84° C.

Step C: Preparation of 2-[2-methyl-4-(3tert.butylamino-2-hydroxypropoxy)-phenyl]-4-trifluoromethylimidazole To sodium acetate trihydrate (6.26 g., 0.046 mole) in water (26 ml.) is added dibromotri-fluoroacetone (6.26 g., 0.023 mole). The solution is heated for 45 minutes on a steam bath, cooled, and added to a solution of 2-methyl-4-(3-tert.-butylamino-2-hydroxypropoxy)-benzaldehyde (3.05 g., 0.0115 mole) in methanol (60 ml.) and concentrated aqueous ammonia (20 ml.). The solution is allowed to stand for 5 hours at room temperature. The methanol is removed under reduced pressure (20 mm. Hg.) over steam and the residue treated with chloroform (3×50 ml.) and saturated sodium carbonate (50 ml.). The organic layer is concentrated to dryness and the residue crystallized from acetonitrile to give 1.2 g. of 2-[2-methyl-4-(3-tert.-butylamino-2-hydroxypropoxy) phenyl]-4-trifluoromethylimidazole, m.p. 162°–164° C.

EXAMPLE 4

Preparation of 2-[4-(3-tert. butylamino-2-hydroxypropoxy)phenyl[-4-phenylimidazole A solution of p-(3-tert. butylamino-2-hydroxypropoxy)benzaldehyde (5.0 g., 0.02 mole), phenylglyoxal monohydrate (6.04 g., 0.04 mole), concentrated aqueous ammonia (50 ml.), water (50 ml.) and methanol (200 ml.) is allowed to stand at room temperature for 5 hours. The solution is concentrated to a residual oil under reduced pressure (20 mm. Hg.) and treated with saturated sodium carbonate (50 ml.) and chloroform (3×50 ml.). The organic layer is concentrated to dryness and chromatographed on neutral alumina (500 g.) using a gradient elution technique starting with chloroform. The product is eluted with 10% methanol-90% chloroform. Final purification is accomplished by passing through a column of silica gel (150 g.) and eluted with 20% methanol-80% chloroform. The solvent is removed under reduced pressure (20 mm. Hg.) and the residue crystallized from acetonitrile to give 0.7 g. of 2-[4-(3-tert.butylamino-2-hydroxypropoxy)phenyl]-4-phenylimidazole, m.p. 176°–178° C.

S-4-[3-(3,4-dimethoxyphenylethyl)amino-2-hydroxypropoxy]benzaldehyde is used in place of p-(3-tert.-butylamino-2-hydroxypropyl)benzaldehyde and 2-thienylglyoxal is used in place of phenyl glyoxal monohydrate in Example 4 to obtain S-2-[4-(3,4-dimethoxyphenylethylamino)-2-hydroxypropoxy]phenyl-4-(2-thienyl)-imidazole.

EXAMPLE 5

Step A: Preparation of S-4-(3-tert.butylamino-2-hydroxypropoxy)benzaldehyde

To a solution of S-2-phenyl-3-tert. butyl-5-hydroxymethyloxazoldine (47 g., 0.2 mole) in pyridine (75 ml.) is added portionwise p-toluenesulfonyl chloride keeping the internal temperature between 25° and 30° C. The mixture is stirred 2 hours after addition is complete keeping the temperature between 25° and 30° C. Ice water (150 ml.) and potassium carbonate (27.6 g.) are added and the mixture is extracted with chloroform (3×100 ml.). The organic extract is dried over sodium sulfate and concentrated first at 20 mm. Hg. and then at 1 mm. Hg. keeping the temperature below 50° C. The residual oil is dissolved in N,N-dimethylformamide (150 ml.) and added dropwise to a refluxing solution of the sodium salt of p-hydroxybenzaldehyde (0.2 mole) in N,N-dimethylformamide (200 ml.). After refluxing 10 hours, the reaction mixture is concentrated first at 20 mm. Hg. and then at 1 mm. Hg. The residue is treated with 5% sodium hydroxide solution and extracted with chloroform (3×100 ml.). The organic extract is dried over sodium sulfate and the residue chromatographed on alumina (500 g. activity grade II). The chromatographic fractions are concentrated and the residue distilled at 240° C. at 0.3 mm. Hg. The distillate (21 g.) is treated with 1 N hydrochloric acid (75 ml.), heated ½ hours over steam, cooled and extracted with either. The aqueous layer is made basic to pH 10 by the addition of 2% sodium hydroxide solution and extracted with chloroform (3×100 ml.). The organic extract is dried over sodium sulfate and concentrated to an oil which after crystallization from hexane yields 14.5 g. of S-4-(3-tert. butylamino-2-hydroxypropoxy)benzaldehyde, m.p. 60°–62° C.

(S)-2-phenyl-3-(3,4-dimethoxyphenylethyl)-5-hydroxymethyloxazolidine is used in place of (S)-2-phenyl-3-tert. butyl-5-hydroxymethyloxazolidine in the A. process to yield (S)-4-[3-(3,4-dimethoxyphenylethyl)amino-2-hydroxypropoxy]benzaldehyde.

Step B: Preparation of S-2-[4-(3-tert. butylamino-2-hydroxypropoxy)phenyl]-4-trifluoromethyl imidazole To sodium acetate trihydrate (20.2 g., 0.15 mole) in water (100 ml.) is added dibromotrifluoroacetone (20.2 g., 0.075 mole). The solution is heated 45 minutes on a steam bath, cooled and is added to a solution of s-p-(3-tert. butylamino-2-hydroxypropoxy)-benzaldehyde (12.5 g., 0.05 mole) in methanol (200 ml.) and concentrated aqueous ammonia (75 ml.). The solution is allowed to stand 5 hours at room temperature. The methanol is removed by distillation under reduced pressure (20 mm. Hg.) over steam. The mixture is made basic with saturated aqueous sodium carbonate solution and extracted with ethyl acetate (3×100 ml.). The organic extract is dried over sodium sulfate and concentrated at 20 mm. Hg. over steam. The resulting residue is recrystallized from acetonitrile to yield 7.6 g. of S-2-[4-(3-tert. butylamino-2-hydroxypropoxy)phenyl]-4-trifluoromethylimidazole, m.p. 181°–182° C.

Other Formula I imidazoles prepared using the procedures substantially as described in Examples 1–5 are listed in the following table. It is to be understood that analogous reactants are used to obtain the particular imidazole products.

TABLE II
PREPARED IMIDAZOLES OF FORMULA $$R_3-O-CH_2-CH(OH)-CH_2-NH-R_6$$

(imidazole with R, R₁ substituents; N—H)

| Example No. | Using Procedure of Example | R | $R_1$ | $R_3$ | $R_6$ | M.P. (°C.) |
|---|---|---|---|---|---|---|
| 6 | 1 | H | —CF₃ | phenyl-phenyl (biphenyl) | t-butyl | 207°–210° |
| 7 | 2 | H | —CF₃ | phenyl | t-butyl | 139°–141° |
| 8 | 2 | H | —CF₃ | phenyl | —CH(CH₃)—CH₂—CH₂—phenyl | 159°–170° |
| 10 | 2 | H | —CF₃ | phenyl | n-propyl | 153°–155° |
| 9 | 2 | H | —CF₃ | phenyl | —CH(CH₃)—CH₂—CH₂—phenyl | 120°–133° |
| 11 | 2 | H | —CF₃ | phenyl | cyclopropyl | 163.5°–165° |

TABLE II-continued
PREPARED IMIDAZOLES OF FORMULA $$R_3-O-CH_2-CH(OH)-CH_2-NH-R_6$$

(imidazole ring with R and $R_1$ substituents)

| Example No. | Using Procedure of Example | R | $R_1$ | $R_3$ | $R_6$ | M.P. (°C.) |
|---|---|---|---|---|---|---|
| 12 | 3 | H | —CF$_3$ | 2,5-dimethylphenyl | t-butyl | 187°–190° |
| 13 | 3 | H | —CF$_3$ | 4-methylphenyl | t-butyl | 183°–185° |
| 13a | 3 | H | —CF$_3$ | 2,6-dimethylphenyl | t-butyl | 159°–162° |
| 14 | 3 | H | —CF$_3$ | 2-naphthyl | isopropyl | 210°–213° |
| 15 | 3 | H | —CF$_3$ | 3,4-dichlorophenyl | t-butyl | 181°–182° |

TABLE II-continued
PREPARED IMIDAZOLES OF FORMULA
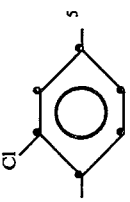
| Example No. | Using Procedure of Example | R | $R_1$ | $R_3$ | $R_6$ | M.P. (°C.) |
|---|---|---|---|---|---|---|
| 16 | 3 | H | —$CF_3$ | 4-Cl-phenyl | t-butyl | 167°–171° |
| 17 | 3 | H | —$CF_3$ | biphenyl | t-butyl | 207°–210° |
| 18 | 3 | H | —$CF_3$ | 3-Cl-phenyl | t-butyl | 174°–177° |
| 19 [1] | 4 | phenyl | phenyl | phenyl | t-butyl | 180°–181° |
| 20 | 4 | H | H | phenyl | t-butyl | 162°–164° |

TABLE II-continued
PREPARED IMIDAZOLES OF FORMULA
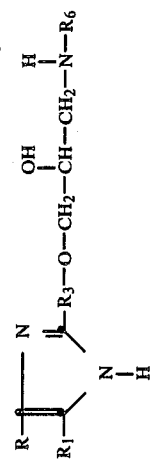
| Example No. | Using Procedure of Example | R | R₁ | R₃ | R₆ | M.P. (°C.) |
|---|---|---|---|---|---|---|
| 21 | 4 | H | H | phenyl | t-butyl | 193.5°–196° [2] |
| 22 | 4 | H | 4-Cl-phenyl | phenyl | t-butyl | 186°–188° |
| 23 | 4 | H | 4-F-phenyl | phenyl | t-butyl | 167°–169° |
| 24 | 4 | H | 4-CH₃O-phenyl | phenyl | t-butyl | 179°–181° |
| 25 | 4 | H | 3,4-diCl-phenyl | phenyl | t-butyl | 189°–190° |
| 26 | 4 | H | pyridyl | phenyl | t-butyl | 101°–105° |

TABLE II-continued
PREPARED IMIDAZOLES OF FORMULA $$R-\overset{N}{\underset{R_1}{\bigg|\bigg|}}\overset{}{\underset{\underset{H}{N}}{\bigg\langle}}\overset{OH\quad H}{\underset{}{\bigg|}}R_3-O-CH_2-CH-CH_2-N-R_6$$

| Example No. | Using Procedure of Example | R | $R_1$ | $R_3$ | $R_6$ | M.P. (°C.) |
|---|---|---|---|---|---|---|
| 27 | 4 | H | H | phenyl | t-butyl | 158°–162° [3] |
| 28 | 4 | H | furyl (O) | phenyl | t-butyl | 172°–173° |
| 29 | 4 | H | thienyl (S) | phenyl | t-butyl | 178°–180° |
| 30 | 4 | H | pentafluorophenyl | phenyl | t-butyl | 168°–170° |
| 31 | 5 | H | —CF$_3$ | phenyl | t-butyl | 178°–179.5° [4] |
| 32 | 5 | H | —CF$_3$ | 3-methylphenyl | t-butyl | 141°–143° [3] |

TABLE II-continued
PREPARED IMIDAZOLES OF FORMULA
| Example No. | Using Procedure of Example | R | $R_1$ | $R_3$ | $R_6$ | M.P. (°C.) |
|---|---|---|---|---|---|---|
| 33 | 5 | H | —$CF_3$ | 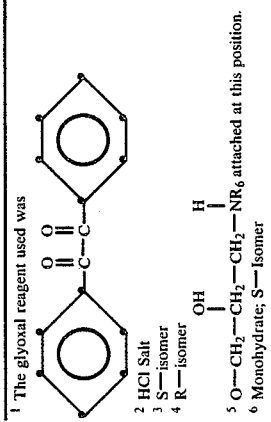 | t-butyl | 110°–120° [6] |
[1] The glyoxal reagent used was
[2] HCl Salt
[3] S—isomer
[4] R—isomer
[5] O—$CH_2$—$CH_2$—$CH_2$—$NR_6$ attached at this position.
$$\overset{OH}{\underset{}{|}} \quad \overset{H}{\underset{}{|}}$$
O—$CH_2$—CH—$CH_2$—N
[6] Monohydrate; S—Isomer

EXAMPLE 34

Step A: Preparation of 2-[4-(3-Chloro-2-hydroxypropoxy)phenyl]-4-trifluoromethylimidazole To sodium acetate trihydrate (5.8 g.) in water (20 ml.) is added trifluorodibromoacetone (5.8 g.); the resulting mixture is heated 0.5 hours on a steam bath. After cooling, the solution is added to p-(3-chloro-2-hydroxypropoxy)benzaldehyde (4.2 g.) in methanol (100 ml.) and concentrated at aqueous ammonia (25 ml.). After standing 4.5 hours at room temperature, the methanol is removed by distillation at 20 mm. Hg. over steam; a solid separates and is filtered. After recrystallization from nitromethane, 1.65 g. of 2-[4-(3-chloro-2-hydroxypropoxy)phenyl]-4-trifluoromethylimidazole is obtained, m.p. 181°-183° C.

Step B: Preparation of 2-[4-(2,3-Epoxyproproxy)phenyl]-4-trifluoromethylimidazole To a solution of 2-[p-(3-chloro-2-hydroxypropoxy)phenyl-4-trifluoromethylimidazole (1.92 g.) in methanol (100 ml.) is added crushed potassium hydroxide (1.5 g). The mixture is stirred 3 hours at room temperature, neutralized with acetic acid and concentrated under reduced pressure (20 mm. Hg. over steam. The residue is triturated with water (25 ml.), filtered and recrystallized by dissolving in benzene and adding hexane until turbid. A yield of 1.2 g. of 2-[4-(2,3-epoxypropoxy)phenyl]-4-trifluoromethylimidazole is obtained, m.p. 152°-153.5° C.

Step C: Preparation of 2-[4-(3-tert. Butylamino-2 hydroxypropoxy)phenyl]-4-trifluoromethyl imidazole A solution of 2-[4-(2,3-epoxypropoxy)phenyl] trifluoromethylimidazole (2.5 g.) in tert. butylamine (20 ml.) is heated 6 hours at reflux. The excess tert.butylamine is removed by distillation at atmospheric pressure over steam. The residue is triturated with nitromethane (5 ml.) and the resulting solid removed by filtration. After recrystallization from acetonitrile, (1.2 g.) of 2-[4-(3-tert. butylamino-2-hydroxypropoxy)-phenyl]-4-trifluoromethylimidazole is obtained, m.p. 185.5°-186.5° C.

EXAMPLE 35

Step A: Preparation of 4-(3-tert. Butylamino-2-hydroxydroxypropoxy)benzaldehyde To 4-(2,3-epoxypropoxy)benzaldehyde (20 g.) is added tert. butylamine (50 ml.) and the resulting solution is refluxed 17 hours. The excess tert. butylamine is removed by heating at atmoxpheric pressure to yield a solid residue. To this residue is added 6N hydrochloric acid (200 ml.) and the resulting mixture is heated 5 hours on a steam bath. The solution is cooled and concentrated to 100 ml. on a steam bath under reduced pressure (20 mm. Hg.). The concentrated solution is made basic to pH 10 with saturated aqueous sodium carbonate and extracted with chloroform. The chloroform extract is concentrated to a solid which after recrystallization from acetonitrile yields 18 g. of 4-(3-tert. butylamino-2-2-hydroxypropoxy)-benzaldehyde, m.p. 123°-215.5° C.

Step B: Preparation of 2-[4-(3-tert.Butylamino-2-hydroxypropoxy)-phenyl]-4-trifluoromethyl imidazole To sodium acetate trihydrate (11.8 g., 0.088 moles) in water (40 ml.) is added dibromotrifluoroacetone (11.8 g., 0.044 moles). The solution is heated 45 minutes on a steam bath, cooled and added to a solution of 4-(3-tert-.butylamino-2-hydroxyproposy)-benzaldehyde (5 g., 0.02 moles) in methanol (200 ml.) and concentrated aqueous ammonia (25 ml.). The solution is allowed to stand 5 hours at room temperature. The methanol is removed under reduced pressure (20 mm. Hg.) over steam and chloroform (50 ml.) and saturated aqueous sodium carbonate (25 ml.) are added to the residue. After stirring a solid separates is filtered and washed with water. After recrystallization from acetonitrile, 3 g. of 2-[4-3-tert. butylamino-2-hydroxypropoxy)-phenyl]-4-trifluoromethylimidazole is obtained, m.p. 189°-191° C.

EXAMPLE 36

Step A: Preparation of Salicylaldehyde Diethyl acetal

A mixture of salicylaldehyde (80 g., 0.0655 mole), triethylorthoformate (110 g., 0.765 mole), absolute ethanol (40 ml.) and concentrated sulfuric acid (3 drops) is heated to reflux overnight. The volatiles are removed under reduced pressure (20 mm. Hg.) over steam to give diethyl acetal of salicylaldehyde which is used without further purification.

Step B: Preparation of 2-(2,3-Epoxypropoxy) benzaldehyde Diethyl acetal

To epichlorohydrin (37 g., 0.4 mole) heated at 50° C. is added dropwise a solution of salicylaldehyde diethyl acetal (25 g., 0.13 mole) in 2N sodium hydroxide solution (200 ml.) and the mixture allowed to stir overnight at 50° C. The reaction mixture is extracted with chloroform (3×100 ml.), dried over potassium carbonate, and concentrated to dryness to give 34.3 g. of 2-(2,3-epoxypropoxy) benzaldehyde diethyl acetal.

Step C: Preparation of 2-(3-tert. butylamino—2-hydroxypropoxy)benzaldehyde

A solution of 2-(2,3-epoxypropoxy)benzaldehyde diethyl acetal (53 g., 2.1 mole) and tert. butylamine (100 ml.) is heated to reflux for 2 hours and allowed to stand at room temperature overnight. The excess tert. butylamine is removed under reduced pressure (20 mm. Hg.) and the residue heated on a steam bath with 6N hydrochloric acid (300 ml.). After cooling, the solution is neutralized with solid sodium bicarbonate, extracted with chloroform (3×100 ml.), dried over sodium sulfate, filtered and concentrated to dryness. The residue is chromatographed on silica gel (500 ml.) using gradient elution techniques starting with chloroform and the product is obtained with 10% methanol 90% chloroform. After removal of the solvent under reduced pressure (20 mm. Hg.), the residue is crystallized from acetonitrile to give 13.8 g. of 2-(3-tert. butylamino-2-hydroxypropoxy) benzaldehyde, m.p. 156°-160° C.

Step D: Preparation of 2-[2-(3-tert. butylamino-2-hydroxypropoxy)phenyl]-4-triflurome-thylimidazole To sodium acetate trihydrate (5.4 g., 0.0396 mole) in water (20 ml.) is added dibromotrifluoroacetone (5.4 g., 0.02 mole). The solution is heated for 45 minutes on a steam bath, cooled and added to a solution of 2-(3-tert. butylamino-2-hydroxypropoxy) benzaldehyde (3.6 g., 0.0143 mole) in methanol (100 ml.) and concentrated aqueous ammonia (25 ml.). The solution is allowed to stand overnight at room temperature. The methanol is removed by distillation under reduced pressure (20 mm. Hg.) and the residue treated with saturated sodium carbonate (50 ml.), extracted with chloroform (3×50 ml.) and separated. The organic layer is dried over sodium sulfate, filtered and concentrated to dryness. The residue is chromatographed on silica gel (400 ml.) and the product eluted with 20% methanol-80% chloroform. Recrystallization of the product from nitro methane gives 700 mg. of 2-[2-(3-tert. butylamino-2-hydroxypropoxy)phenyl]-4-trifluoromethyl-imidazole, m.p. 105°–107° C.

EXAMPLE 37

2-[4-(3-tert. butylamino-2-hydroxypropoxy)phenyl]-4-methylimidazole

To a mixture of cupric acetate (5.0 g., .025 mole), acetoxyacetone (1.5 g., .013 mole), concentrated aqueous ammonium (25 ml.) is added a solution of p-(3-tert. butylamino-2-hydroxypropoxy) benzaldehyde (3.2 g., .0127 mole) in methanol (25 ml.). After the addition, the mixture is heated at reflux overnight. The methanol is removed by distillation under reduced pressure (20 mm. Hg.) over steam and water (200 ml.) is added to the residue. The resulting solution is treated with hydrogen sulfide, filtered throught a filter aid, treated with solid potassium carbonate until basic and extracted with chloroform (3×50 ml.). The chloroform is concentrated to dryness and the residue chromatographed on neutral alumina (170 g.) using a gradient elution technique starting with chloroform. The material is eluted off the column using 5% methanol-95% chloroform. The organic solvent is removed by distillation under reduced pressure (20 mm. Hg.) and the residue crystallized from acetonitrile to give 0.79 g. of 2-[4-(3-tert. butylamino-2-hydroxypropoxy)phenyl]-4-methyl-imidazole, m.p. 202°–203° C.

EXAMPLE 38

Step A: β-Pyridylglyoxal-dimethylacetal

To a solution of butyl lithium (129 ml., 193N, 0.25 m.) in ether (300 ml.) cooled below −50° C. is added 3-bromopyridine (33.02, 0.209 m.) in ether (60 ml.). The yellow suspension which results is allowed to stir an additional ½ hour at −50° C. and dimethoxyacetic acid piperidide (33.6 g., 0.179 m.) in ether (90 ml.) is added over 1 hour at −50° C. After complete addition, the reaction mixture is allowed to warm to room temperature and heated to reflux for ½ hour. After cooling, a solution of ammonium chloride (500 ml.) is added separated and the aqueous layer extracted with 2×100 ml. ether. The ether layer is washed with 3N $H_2SO_4$, acid; the aqueous layer is neutralized with KOH and extracted with 3×100 ml. $CH_2Cl_2$, dried over $Na_2SO_4$, filtered and concentrated to dryness. The remainder is distilled at 95–100/0.4 mm. to give 13.8 g. of β-pyridyl-glyoxaldimethylacetal.

Step B:
4-(3-Pyridyl)-2-[4-(3-tert-butylamino-2-hydroxypropoxy)phenyl]-imidazole To concentrated sulfuric acid (15 g.) cooled to 0°–4° is added β-pyridylglyoxal-dimethylacetal (5.4 g., 0.03 m) and the solution allowed to stand at room temperature. After 3 days, the mixture is cooled and neutralized with $NaHCO_3$ (26 g., 0.30 m).

To this solution is added water (25 ml.), 37% aqueous ammonia (75 ml.), methanol (25 ml.) and a solution of p-(3-tert-butylamino-2-hydroxypropoxy) benzadehyde (5.1 g., 0.02 m) in methanol (200 ml.). After standing at room temperature for 3 days, the methanol is removed under reduced pressure (20 mm) over steam, the residue covered with saturated $Na_2CO_3$ (100 ml.), extracted with $CHCl_3$ (3×150 ml.), dried over $Na_2SO_4$, filtered and concentrated to dryness. The residue is chromatographed on silica gel (600 ml.) and the product eluted with 50% $CHCl_3/MeOH$. The crude product is further purified by chromatography on No. 2 neutral alumina (90 g.) and eluted with 2% $MeOH/CHCl_3$. Recrystallization from acetonitrile/chloroform gave 125 mg. of 4-(3-pyridyl)-[4-(3-tert-butylamino-2-hydroxypropoxy) phenyl]-imidazole.

EXAMPLE 39

(S) Methyl-2-[4-(3-tert-butylamino-2-hydroxypropoxy)-phenyl]imidazole-4-carboxylate To 1N sodium hydroxide solution (20 ml.) is added (S)-2-[4-(3-tert-butylamino-2-hydroxypropoxy) phenyl]-4-trifluoromethylimidazole (1 g.) and the mixture is heated 0.5 hour over steam. The resulting solution is neutralized to pH 7 with concentrated hydrochloric acid and concentrated on a steam bath over a stream of nitrogen. The resulting solid[1] is suspended in methanol (25 ml.) saturated with hydrogen chloride. The mixture is refluxed three hours with hydrogen chloride being added after the first and second hour. After being concentrated under reduced pressure (20 mm.) over steam, saturated aqueous solid carbonate solution is added (25 ml.) and the mixture extracted with ethyl acetate. The organic extract was concentrated to a gum which on trituration with aqueous sodium carbonate solidifies and is filtered. After recrystallization from acetonitrile 200 mg. of (S)-methyl 2-[4-(3-tert. butylamino-2-hydroxypropoxy)phenyl]imidzole-4-carboxylate melting at 159°–161° C. is obtained.

[1] Crude S-2-[4-(3-tert. butylamino-2-hydroxypropoxy) phenyl]-4-carboxy-imidazole.

EXAMPLE 40

Step A: S-2-Phenyl-3-Tert. butyl-5-(3-cyano-6-pyridyloxymethyl)oxazolidine

To a solution of S-2-phenyl-3-tert. butyl-5-hydroxymethyloxazolidine (12.35 g., 0.0526 mole) in dimethylformamide (65 ml.) is added sodium hydride (2.22 g., 0.0526 mole of 57%. After heating 25 minutes on a steam bath, the mixture is stirred and cooled to room temperature in 30 minutes and added to a solution of 6-chloronicotinonitrile (7.28 g., 0.0526 mole) in dimethylformamide (35 ml.). The reaction mixture is stirred at room temperature for 4½ hours and then is concentrated under reduced pressure. The fluid residue is taken up in ether and washed with water. The ether solution is dried and concentrated under reduced pressure to yield 18.5 g. of S-2-phenyl-3-tert. butyl-5-(3-cyano-6-pyridyloxymethyl)oxazolidine as an oil.

Step B: S-6-(3-Tert. butylamino-2-hydroxypropoxy) nicotinonitrile

A suspension of S-2-phenyl-3-tert. butyl-5-(3-cyano-6-pyridyloxymethyl) oxazolidine (18.5 g.) in 1N hydrochloric acid (60 ml.) is heated 5 minutes on a steam bath and then stirred at room temperature for ¼ hour. The mixture is extracted with chloroform and the aqueous layer is made basic with 40% sodium hydroxide solution. The basic solution is extracted with ethyl acetate and the extract is dried and concentrated under reduced pressure. The residual white solid is recrystallized from hexane-n-butyl chloride to yield 5.14 g. of S-6-(3-tert. butylamino-2-hydroxypropoxy) nicotinonitrile, m.p. 103°–105° C.

Step C: S-6-(3-Tert. butylamino-2-hydroxypropoxy) nicotinaldehyde

A suspension of S-6-(3-tert. butylamino-2-hydroxypropoxy) nicotinonitrile (5.14 g. 0.0204 mole) in toluene (128 ml.) in a flamed flask is heated with stirring until a solution is obtained. The toluene is allowed to distill until a total of 21 ml. is collected. Heating is discontinued and the reaction solution is cooled in a dry ice-acetone bath causing the starting material to reprecipitate. To the cold reaction mixture is added diisobutylaluminum hydride in toluene (62.6 ml. 0.075 mole of 0.17 g./ml.) dropwise under nitrogen with stirring. The yellow reaction mixture is stirred cold for 1 hour, and then the acetone bath is removed as methanol (22 drops) is added followed by the addition of water (22 drops). Chloroform is added to the mixture and then water (43 ml.), and after good stirring the mixture is filtered. The filtrate is shaken in a separatory funnel and the organic layer is separated, dried, and concentrated under reduced pressure. To the residual oil is added 1% hydrochloric acid (43 ml.) and the mixture is heated on a steam bath for ½ hour. At this point the pH is basic. Concentrated hydrochloric acid is added until the pH is acid and heating is continued for 15 minutes. The mixture is cooled and made basic with 40% sodium hydroxide solution and then extracted with chloroform. The extract is dried and concentrated under reduced pressure to yield 5.1 g. of S-6-(3-tert. butylamino-2-hydroxypropoxy) nicotinaldehyde as an oil which solidifies.

Step D: S-2-[2-(3-tert. Butylamino-2-hydroxypropoxy)-5-pyridyl]-4-trifluoromethylimidazole To sodium acetate trihydrate (2.16 g., 0.016 moles) in H$_2$O (15 ml.) is added dibromotrifluoroacetone (2.16 g., 0.008 moles) and the mixture is heated ½ hour on a steam bath. After cooling the solution is added to 6-(3-tert.-butylamino-2-hydroxypropoxy) nicotinaldehyde (1 g.) in methanol (50 ml.) and concentrated aqueous ammonium hydroxide (15 ml.). After standing 20 hours at room temperature, the methanol is removed under reduced pressure (20 mm.) over steam. Concentration aqueous sodium carbonate (10 ml.) and ethyl acetate (50 ml.) are added to the concentrated solution. After extracting the organic layer is separated dried over sodium sulfate and concentrated to a gum which is chromatographed on activity grade II alumina with chloroform methanol using a gradient eluton technique. The fractions containing product are combined and concentrated to a gum which is dissolved in ethyl acetate. The ethyl acetate solution is washed with saturated sodium carbonate solution, dried and concentrated to yield 2-[2-(3-tert.butylamino-2-hydroxypropoxy)-5-pyridyl]-4-trifluoromethylimidazole as a non-crystalline solid (650 mg).

This non-crystalline solid was covered with hexane and allowed to stand at about 0° C. for 7 days. The hexane was then decanted and the residue triturated with ether to yield a solid. The ether filtrate also yielded solid on standing at room temperature. These solids were combined and dissolved in benzene. Hexane was added to the point of turbidity, which on cooling yielded a solid. The solid was dried at 66°–73° C. and 0.2 mm for about 48 hours. The dried solid was S-2-[2-(3-tert. butylamino-2-ydroxypropoxy)-5-pyridyl]-4-trifluoromethylimidazole monohydrate (NMR and Mass Spectroscopic analysis), melting at 110°–120° C.

EXAMPLE 41

Step A: 4-(p-methoxyphenyl)-2-(3-pyridyl)imidazole

A solution of sodium acetate trihydrate (5.8 g, 0.04 m), 3-pyridinecarboxaldehyde (2.3 g., 0.02 m), p-methoxyphenylglyoxal monohydrate (3.92 g., 0.02 m), water (20 ml.), concentrated aqueous ammonia (25 ml.), and methanol (75 ml.) is allowed to stand at room temperature overnight. The solution is concentrated to dryness under reduced pressure (20 mm) over steam, treated with saturated Na$_2$CO$_3$ (100 ml.) and extracted with chloroform (3×100 ml.). The organic layer is dried over Na$_2$SO$_4$, filtered and concentrated to dryness. The residue is chromatographed on silica gel (300 ml.) and the product eluted with 3–5% MeOH/CHCl$_3$. The material is crystallized from acetonitrile to give 2.3 g. of 4-(p-methoxyphenyl)-2-(3-pyridyl)imidazole of m.p. 184–186.

Step B: 2-(3-pyridyl)-4-(4-hydroxyphenyl)imidazole

A mixture of 4-(p-methoxyphenyl)-2-(3-pyridyl)-imidazole (2.0 g.) and 48% HBr (100 ml.) is heated to reflux for 20 hrs. After cooling, the precipitate is filtered off and crystallized from isopropanol-methanol to give 2.05 g. of 2-(3-pyridyl)-4-(4-hydroxyphenyl)-imidazole of m.p. 315°-318° C.

Step C: 4-[4-(3-tert-butylamino-2-hydroxypropoxy) phenyl]-2-(3-pyridyl)imidazole A solution of 2-phenyl-3-tert-butyl-5-hydroxymethyloxazolidine (2.4 g., 0.01 m) in pyridine (3 ml.) is cooled to 0°-4° C. and treated portionwise with p-toluene-sulfonylchloride (2.0 g., 0.01 m). The cooled solution is slowly warmed to room temperature while not allowing the reaction mixture to exceed 30° C. After 2.5 hrs., the mixture is treated with a solution of $K_2CO_3$ (1.4 g.) in water (20 ml.) and extracted with chloroform (3×50 ml.). The organic layer is dried over $Na_2SO_4$, filtered, and concentrated to dryness under reduced pressure (20 mm) over steam and finally at 60° C. and 1 mm. The residual oil is dissolved in dry N,N dimethylformamide (DMF) (20 ml.) and added dropwise to a mixture of 2-(3-pyridyl)-4-(4-hydroxyphenyl) imidazole:$2HBr:H_2O$ (4.0 g., .0095 m) in DMF (20 ml.) and sodium hydride (57% oil suspension, 1.3 g., 0.031 m). After refluxing for 11 hours, the mixture is concentrated to dryness under reduced pressure (1-2 mm Hg.) over steam. The residue is treated with 1N HCl (100 ml.), heated for ½ hr. on a steam bath, cooled, and extraced with ether. The aqueous layer is neutralized with 10N NaOH (12 ml.), extracted wtih $CHCl_3$ (3×50 ml.), dried oer $Na_2SO_4$, filtered and concentrated to dryness.

The residue is chromatographed on No. 2 neutral alumina (200 g.) and eluted with 4% $MeOH/CHCL_3$. The crude product is further purified by chromatography on silica gel (200 ml.) and eluted with 40-50% $MeOH/CHCl_3$. The material is crystallized from acetonitrile to give 0.425 g. of 4-[4-(3-tert-butylamio-2-hydroxypropoxy)phenyl]-2-(3-pyridyl)imidazole of m.P. 163°-165° C.

EXAMPLE 42

Methyl 2-[4-(3-tert-butylamino-2-hydroxpropoxy) phenyl]imidazole-4-carboxylate

A solution of crude 2-[4-(3-tert-butyl amino-2-hydroxypropoxy)phenyl]-4-carboxyimidazole[1] (30 g.) in methanol (600 ml.) is heated to reflux, and then heating is discontinued as hydrogen chloride is bubbled rapidly through the solution with stirring for a half hour, followed by two and a half hours at reflux. Bubbling of hydrogen chloride is continued for another two hours followed by another hour at reflux and then the reaction mixture is stirred at room temperature overnight. The mixture is filtered and the filtrate is then concentrated to dryness under reduced pressure. The residue is dissolved in water (150 ml.) and the pH is adjusted to 8 with saturated sodium carbonate solution. The basic mixture is extracted with ethyl acetate and the extracts are dried, filtered, and concentrated under reduced pressure to yield a solid which is recrystallized from acetonitrile to yield the methyl 2-[4-(3-tert. butylamino-2-hydroxypropoxy)phenyl]imidazole-4-carboxylate as a cream-colored solid, m.p. 168°-172° C.

[1] Prepared from the corresponding 4-trifluoromethylimidazole per Example 39 procedure.

EXAMPLE 43

Step A: 2-[4-(3-tert. butylamino-2-hydroxypropoxy) phenyl]-4-carbamoylimidazole

A solution of methyl 2-[4-(3-tert. butyl amino-2-hydroxypropoxy)phenyl]imidazole-4-carboxylate (10 g.) in methanol (100 ml.) is reacted in a bomb with ammonia (44 g.) at 100° C. for about 24 hours. The reaction mixture is concentrated under reduced pressure and the residue is chromatographed on silica gel. The product is eluted with chloroform that is washed with concentrated aqueous ammonia (90%) and methanol (10%) and is recrystallized from acetonitrile to yield the 2-[4-(3-tert. butylamino-2-hydroxypropoxy)-phenyl]-4-carbamoylimidazole as a white solid, m.p. 149°-154° C.

Step B: 2-[4-(3-tert.-butylamino-2-hydroxypropoxy) phenyl]-4-cyanoimidazole

To a solution of 2-[4-(3-tert.-butylamino-2-hydroxypropoxy)phenyl]-4-carbamoylimidazole (0.5 g.) in dry pyridine (10 ml.) is added trifluoroacetic anhydride (1.26 g.) portionwise with stirring. The reaction solution is refluxed with stirring for four hours and then concentrated under reduced pressure. The residual gum is taken up in ethanol and saturated sodium carbonate solution (15 ml.) and stirred at room temperature for 20 hours. The ethanol is removed under reduced pressure and the remaining aqueous mixture is extracted with ethyl acetate. The extract is dried over sodium sulfate, filtered, and concentrated under reduced pressure. The residual glass is converted to its hydrochloride salt with ethanolic HCl and is recrystallized from ethanol ether. The resulting tan solid is converted back to its free base by trituration with saturated sodium carbonate solution. The free base is extracted into ethyl acetate and the extract is dried over sodium sulfate, filtered and concentrated under reduced pressure. The residual gum is recrystallized from acetonitrile to yield 40 mg. of 2-[4-(3-tert.butylamino-2-hydroxypropoxy)phenyl]-4-cyanoimidazole, m.p. 174°-177° C.

EXAMPLE 44

Step A: 4-Hydroxy-5,6,7,8-tetrahydronapthaldehyde

Dry hydrogen chloride gas is bubbled into a suspension of 5.0 gms. of 5, 6, 7, 8-tetrahydronaphthol and 6.0 gm. zinc cyanide in 60 ml. of dry ethyl ether for two hours. To the mixture is added cautiously 50 ml. of water and 10 ml. 95% ethanol, and the resulting mixture is refluxed ½ hour. After cooling, the mixture is extracted with ethyl ether. The ether layer is washed with water and dried over anhydrous sodium sulfate. The ether is filtered and concentrated to an oil. The oil is dissolved in benzene, and 4-hydroxy-5,6,7,8-tertrahydronapththaldehyde crystallizes and is filtered.

Step B: 4-(2,3-Epoxypropoxy)-5,6,7,8-tetrahydronapthaldehyde

To a solution of 4-hydroxy-5,6,7,8-tetrahydronapthaldehyde (20 gms., 0.012 m) in 1.5N sodium hydroxide (20 ml.) at 50° C. is added epichlorohydrin (3.3 gms., 0.036 m) dropwise. After 3 hours at 50° C., the solution is cooled and extracted with chloroform. The chloroform is dried over anhydrous sodium sulfate, filtered and concentrated to an oil. The oil is purified by column chromatography to give 2.4 gm. of 4-(2,3-epoxypropoxy)-5,6,7,8-tetrahydronapthaldehyde.

Step C:
4(3-tert.-butylamino-2-hydroxypropoxy)-5,6,7,8-tetrahydronapthaldehyde To 4-(2,3-epoxypropoxy)-5,6,7,8-tetrahydronapthaldehyde (2.4 gms) is added tert.-butylamine (15 ml.). The resulting solution is heated at 45° C. for 15 hours. The excess tert.-butylamine is removed at reduced pressure (20 mm). To the residue is added 30 ml. 6N hydrochloric acid, and the resulting mixture is refluxed for three hours. The acidic mixture is poured into a saturated solution of sodium carbonate which is heated on a steam bath with nitrogen bubbling through it. The basic mixture is extracted with chloroform, which is dried over anhydrous sodium sulfate, filtered and concentrated to give 2.3 g of 4-(3-tert.butylamino-2-hydroxypropoxy)-5,6,7,8-tetrahydronapthaldehyde as an oil.

Step D:
2-[(3-tert.-butylamino-2-hydroxypropoxy)-5,6,7,8-tetrahydronapthyl]-4-trifluoromethylimidazole To sodium acetate trihydrate (2.07 gm., 0.015 m) in water (20 ml.) is added dibromotrifluoroacetone (2.07 g., 0.0075 m). The solution is heated for 40 minutes on a steam bath, cooled and added to a solution of 4-(3-tert.-butylamino-2-hydroxypropoxy)-5,6,7,8-tetrahydronapthaldehyhde (2.3 mgs., 0.0075 m) in methanol (100 ml.) with concentrated aqueous ammonium hydroxide (15 ml.). The solution is allowed to stand at room temperature for 17 hours. The methanol is removed under reduced pressure (20 mm) over steam and ethyl acetate (100 ml.) and saturated aqueous sodium carbonate are added to the residue. The ethyl acetate is separated, dried of anhydrous sodium sulfate, filtered and concentrated. The oil is crystallized from acetonitrile to give 500 mg. of 2-[(3-tert-butylamino-2-hydroxypropoxy)-5,6,7,8-tetrahydronaphthyl]-4-trifluoromethylimidazole. Melting point 203°-205° C.

EXAMPLE 45

Step A: 4-(3-n-Butylamino-2-hydroxypropoxy) benzaldehyde

To 4-(2,3-epoxypropoxy)benzaldehyde (8.9 gms., 0.05 m) is added n-butylamine (30 ml.) and the resulting solution is refluxed 17 hours. The excess n-butylamine is removed under reduced pressure (20 mm). The oil is dissolved in 6N hydrochloric acid (30 ml.) and the solution is heated on a steam bath for 40 minutes. The hot acidic solution is poured into a hot saturated aqueous sodium carbonate solution with nitrogen bubbling through it. The basis solution is extracted with chloroform. The chloroform is dried over sodium sulfate and concentrated to yield 4-(3-n-butylamino-2-hydroxypropoxy)benzaldehyde, as an oil.

Step B: 2-[4-(3-n-Butylamino-2-hydroxypropoxy)phenyl]-4-trifluoromethylimidazole To a solution of sodium acetate trihydrate (5.0 g.) in water (20 ml.) is added dibromotrifluoroacetone (5.0 g.). The solution is heated on a steam bath for 30 minutes. After cooling to room temperature, this solution is added to the methanolic solution of 4-(3-n-butylamino-2-hydroxypropoxy)benzaldehyde and concentrated aqueous ammonium hydroxide (25 ml.). After standing at room temperature for 48 hours, the methanol is removed under reduced pressure (20 mm). The residue is dissolved in ethyl acetate and saturated aqueous sodium carbonate, dried over anhydrous sodium sulfate and concentrated under reduced pressure. The oil is placed in acetonitrile to yield 800 mg. of 2-[4-(3-n-butylamino-2-hydroxypropoxy)phenyl]-4-trifluoromethylimidazole, melting at 151°-154° C.

EXAMPLE 46

S-4-(4-methoxypheny)-2-[4-(3-tert-butylamino-2-hydroxy propoxy)phenyl]imidazole dihydrochloride dihydrate A heterogeneous solution of p-methoxyphenylglyoxal monohydrate (3.19 g. 0.018 m) sodium acetate (2.90 g., 0.036 m), water (23 ml.), 37% aqueous ammonia (23 ml.) and (S)-p-(3-tert-butylamino-2-hydroxypropoxy)-benzaldehyde (2.90 g., 0.012 m) in methanol (75 ml.) is stirred at 25° C. for 72 hours. The reaction mixture is concentrated to dryness under reduced pressure (15 mm) at 80° C. The residual solid is treated with saturated aqueous $Na_2CO_3$ (75 ml.), extracted with chloroform (4×75 ml.), dried over anhydrous $MgSO_4$, filtered and concentrated to dryness. The residue is dissolved in chloroform (50 ml.) and absorbed on an alumina pad (200 g.). The pad is eluted with chloroform (2.1), 5% methanol/chloroform (1 liter), 10% methanol/chloroform (1 1) and methanol (1 liter). Concentration of the 20% methanol/chloroform, 40% methanol/chloroform and methanol solutions gives 1.5 g. of crude (S)-4-(4-methoxyphenyl)-2-[4-(3-tert-butylamino-2-hydroxypropoxy)phenyl]-imidazole. This treatment of this crude product with 8N ethanolic hydrogen chloride (1 ml) yields the hydrochloride salt which is purified by three precipitations from isopropyl alcohol/ethyl acetate to give 810 mg of (S)-4-(4-methoxyphenyl)-2-[4-(3-tert-butylamino-2-hydroxypropoxy)-phenyl]-imidazole dihydrochloride dihydrate; m.p. 132.0-135.0° C.

EXAMPLE 47

Step A: 2,6-Dichloro-4-hydroxybenzaldehyde

To a stirred suspension of calcium hydroxide (61 gm), sodium carbonate (69.7 gm), and 3,5 dichlorophenol (20.97 gm) in water (436 ml) at 74° is added chloroform (45.3 gm) over 90 minutes. The solution is refluxed for 3½ hours. After the slow addition of concentrated hydrochloric acid (170 ml), the acidic solution is steam distilled the aqueous residue is cooled and the solid which separates is filtered. Recrystallization from toluene gives 1.1 gm of 2,6-dichloro-4-hydroxybenzaldehyde.

Step B: 2,6-Dichloro-4-(2,3 epoxypropoxy)benzaldehyde

To a stirred solution of 2,6-dichloro-4-hydroxybenzaldehyde (3.0 gm 0.0167 m) in 1.5N sodium hydroxide (25 m) at 50° is added epichlorohydrin (4.4 gm, 0.048 m). After stirring at 50° for 3 hours, the solution is cooled and extracted with chloroform. The chloroform is dried over anhydrous sodium sulfate, filtered and concentrated to 2,6-dichloro4-(2,3-epoxypropoxy)-benzaldehyde (3 g) which is used without further purification.

Step C: 2,6-Dichloro-4-(3-tert-butylamino-2-hydroxypropoxy)-benzaldehyde

A mixture of 2,6-dichloro-4-(2,3-epoxypropoxy)benzaldehyde (3 gm) and tert-butylamine (20 ml) is heated at 45° for 17 hours. The excess tert-butylamine is removed under reduced pressure (20 mm). The oil is dissolved in 6N hydrochloric acid (25 ml) and heated for 1 hours. The acid solution is added to boiling saturated aqueous sodium carbonate with nitrogen ebullition. The basic solution is extracted with chloroform. The chloroform is dried over anhydrous sodium sulfate, filtered and concentrated to 2,6-dichloro-4-(3-tert-butylamino-2-hydroxypropoxy)benzaldehyde which is used without further purification.

Step D: 2-[2,6-Dichloro-4-(tert-butylamino-2-hydroxypropoxy)phenyl]-4-trifluoromethyl imidazole A solution of sodium acetate trihydrate (2.7 gm 0.02 m) and dibromotrifluoroacetone (276 gm (0.01 m) in water (20 ml) is refluxed for 45 minutes. It is cooled and added to a solution of 2,6-dichloro-4-(3-tert-butylamino-2-hydroxypropoxy)benzaldehyde (3.0 gm. 0.009 m) in methanol (200 ml) and saturate aqueous ammonia (30 ml). After standing at room temperature for 17 hours, the solution is concentrated to an oil. The oil is dissolved in ethylacetate and washed with saturated aqueous sodium carbonate. The ethylacetate is dried over anhydrous sodium sulfate, filtered and concentrated. The gum is purified by chromatograph on silica gel with chloroform, washed with ammonium hydroxide and methanol as solvents. After purification 90 mg of 2-[2,6-dichloro-4(3-tert-butylamino-2-hydroxypropoxy)-phenyl]-4-trifluoromethyl imidazole is obtained.

EXAMPLE 48

1-Methyl-2-[4-(3-tert-butylamino-2-hydroxypropoxy)phenyl]4 (and 5)-trifluoromethyl imidazole An ether solution of diazomethane (1.5 gm) is added to a solution of 2-[4-(3-tert-butylamino-2-hydroxypropoxy)phenyl]-4-trifluoromethylimidazole* in ether (100 ml) and methanol (50 ml). The solution is allowed to stand at room temperature until the yellow color has disappeared. The solvents are removed under reduced pressure. The resulting gum is chromatographed on silica gel with chloroform treated with aqueous ammonium hydroxide and methanol to yield 1-methyl-2-[4-(tert-butylamino-2-hydroxypropoxy)phenyl]-4-(and 5)-trifluoromethyl imidazole, which is a 50—50 mixture of the two N-methyl isomers.

*(1.7 gm)

ANALYSIS:
NMR (d DMSO) N-CH$_3$ doublet. 3.72 3.74 (CH$_3$)-tert-butyl 1.04
Mass spec 371 m+peak 356 m-15

EXAMPLE 49

2-[4-(3-dimethylamino-2-hydroxypropoxy)phenyl]-4-trifluoromethylimidazole

A solution of 2-[4-(2,3-epoxypropoxy) phenyl]-4-trifluoromethylimidazole in triethylamine (15 ml) is added 1.1 equivalents of a dimethylamine. This solution is refluxed until reaction is complete as indicated by TLC. The solvent is removed under reduced pressure and the residue recrystallized to yield 2-[4-(3-dimethylamino-2-hydroxypropoxy)phenyl]-4-trifluoromethylimidazole.

The methods illustrated in the examples 1–49 above are readily utilized to prepare other analogous imidazoles which are encompassed by the present invention.

EXAMPLE 50

S-2-[2-(3-tert.butylamino-2-hydroxypropoxy)-3-chloro-5-pyridyl]-4-trifluoromethylimidazole hydrogen maleate Step A: A mixture of 57% sodium hydride in mineral oil (0.53 g., equivalent to 0.30 g., 0.0126 m, of active sodium hydride) is added over a period of ten minutes to a stirred solution of S-2-phenyl-3-tert. butyl-5-hydroxymethyloxazolidine (2.97 g, 0.0126 m) in 25 ml of anhydrous toluene under nitrogen. The reaction mixture is allowed to stir at 25° C. for 15 minutes, 100° C. for 15 minutes and finally at 25° C. for 30 minutes. The homogeneous solution obtained is added dropwise over a period of 60 minutes to a rapidly stirred solution of 2,3-dichloro-5-cyanopyridine (2.0 g, 0.0126 m) in 20 ml of anhydrous toluene at 0° C. under nitrogen. The heterogenous reaction mixture is stirred rapidly at 0°–5° C. for 60 minutes and at 25° C. for 16 hours. This reaction mixture is then poured into 50 ml of water and the toluene layer separated. The aqueous phase is extracted with additional toluene 3×25 ml). The toluene extracts are combined, washed with saturated aqueous sodium chloride (50 ml), dried over anhydrous sodium sulfate, filtered and concentrated under reduced pressure (25 mm). The residue is diluted with 60 ml of 1N aqueous hydrochloric acid and stirred on a steam bath for 5 minutes and at 25° C. for 30 minutes. The acidic reaction mixture is extracted with diethylether (5×50 ml) and chilled in an ice bath. 10M aqueous sodium hydroxide is added dropwise until the pH is approximately 12–14. The basic reaction mixture is extracted with chloroform (4×50 ml). The chloroform extracts are combined, dried over anhydrous sodium sulfate, filtered and concentrated at reduced pressure (25 mm). The remaining oil is dissolved in refluxing petroleum ether (400 ml), and on cooling to 25° C., 1.38 g of S-2-(tert.butylamino-2-hydroxypropoxy)-3-chloro-5-cyanopyridine is isolated melting at 62.0°–63.0° C.

Step B: A solution of S-2-(3-tert. butylamino-2-hydroxypropoxy)-3-chloro-5-cyanopyridine (11.19 g, 0.0394 m) in anhydrous toluene (100 ml) is stirred rapidly at −73° C. under nitrogen. A solution of diisobutylaluminum hydride in toluene (66.3 ml, (0.0394 m) of a 9.37M solution) is added dropwise over a ten minute period. The heterogeneous reaction mixture is stirred at −73°C. for 6 hours and then allowed to stand at 0° C. for 16 hours. The reaction mixture is stirred at 0° C. and treated dropwise with methanol (50 ml) followed by water (200 ml). The turbid solution is extracted with chloroform (3×200 ml). Chloroform extracts are combined, dried over anhydrous sodium sulfate, filtered and concentrated under reduced pressure (25 mm). The residual oil (11.4 g) is diluted with 60 ml of 6N aqueous hydrochloric acid and stirred at 100° C. for 30 minutes. The homogeneous acid solution is cooled to 0°–5° C. and treated with 10M aqueous sodium hydroxide until the pH is approximately 12–14. The basic solution is saturated with sodium chloride and extracted with chloroform (3×150 ml). The chloroform extracts are combined, dried over anhydrous sodium sulfate, filtered and concentrated at reduced pressure (25 mm) to yield 11.66 g of S-2-(3-tert. butylamino-2-hydroxypropoxy)-3-chloronicotinaldehyde as a light brown oil.

Step C: Sodium acetate (8.66 g., 0.0636 m) is treated with 60 ml of water and the homogeneous solution stirred rapidly at 25° C. Trifluorodibromoacetone (8.58 g, 0.318 m) is added in one portion and the mixture heated at 100° C. for 40 minutes and cooled to 25° C. This solution is immediately added to a homogeneous mixture of S-2-(3-tert. butylamino-2-hydroxypropoxy)-3-chloronicotinaldehyde (6.09 g, 0.212 m), methanol (150 ml) and concentrated aqueous ammonium hydroxide (60 ml). The reaction mixture is allowed to stir at 25° C. for 16 hours, and concentrated at reduced pressure (25 mm) to remove the methanol. The aqueous solution is extracted with 3% methanol/chloroform (2×100 ml) and 5% methanol/chloroform (2×100 ml). All extracts are combined, dried over anhydrous sodium sulfate, filtered and concentrated at reduced pressure (25 mm) to yield 6.98 g of glassy foam. This foam is dissolved in absolute ethanol and the solution filtered through a 150 g silica pad. The filtrate is concentrated to a small volume, treated with a 10% excess of maleic acid and chilled. Upon dilution with diethyl ether, 1.82 g of S-2-[2-(3-tert. butylamino-2-hydroxypropoxy)-3-chloro-5-pyridyl]-4-trifluoromethylimidazole hydrogen maleate was isolated melting at 80.0°–85° C.

The free base may be obtained by conventional neutralization of the hydrogen maleate salt.

REACTION SCHEME FOR EXAMPLES A–D

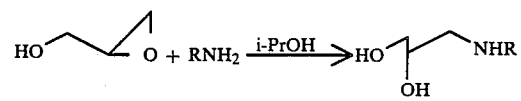

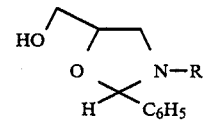

I, R = —CH(CH$_3$)$_2$
II, R = CH$_2$CH$_2$Ph
IIa, R = CH(CH$_3$)—(CH$_2$)$_2$—Ph

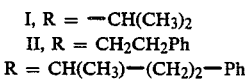

III, R = (CH$_2$)$_2$— 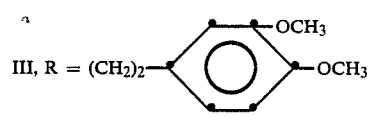

IV, R = —◁

III TsCl or IV Pyridine

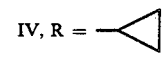

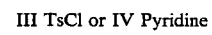

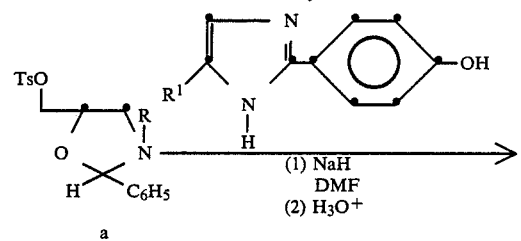

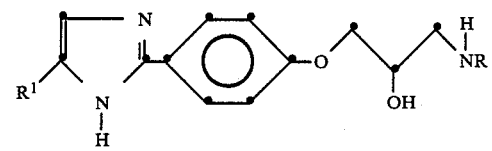

V  R$_1$ = 2-thienyl

R = —(CH$_2$)$_2$— 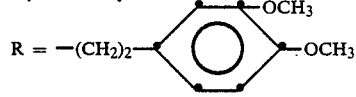

VI  R$_1$ = CH$_3$

R = —(CH$_2$)$_2$— 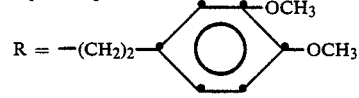

VII  R$_1$ = 2-thienyl

R = 

VIII  R$_1$ = CH$_3$

R = 

EXAMPLE A

Step A: 3-[2-(3,4-Dimethoxyphenyl)ethylamino]-1,1-propanediol, I

To a solution of β-(3,4-dimethoxyphenyl)ethylamine (151.0 g, 0.83 m) in isopropanol (160 ml) heated at 50° is added a solution of glycidol (24.8 g, 0.33 m) in isopropanol (25 ml) over 30 minutes. After heating at 50° for 30 minutes and at 70° for 15 hours, the solvent is concentrated under reduced pressure. The residue is distilled at 224°–227° C. at 0.7 mm to yield I (47.9 g, 57%).

Step B: 3-Cyclopropylamino-1,3-propanediol, II

To a solution of cyclopropylamine (95.2 g, 1.67 m) in isopropanol (240 ml) heated at 45° is added a solution of glycidol (50.0 g, 0.67 m) over 30 minutes. The solution is heated at 50° for 30 minutes, at 70° for 1.5 hours and then stirred at 25° for 15 hours. The solvent is concentrated under reduced pressure and the residue is distilled at 116°–119° C. at 1.6 mm to give II (87.8 g, 79%).

Step C: 2-Phenyl-3-[2-(3,4-dimethoxyphenyl)ethyl]-5-hydroxymethyl)oxazolidine, III A mixture of I (47.9 g, 0.19 m), benzaldehyde (44.6 g, 0.42 m) and benzoic acid (1 g) in toluene (160 ml) is refluxed for 3 hours, collecting the water formed in a Dean-Stark trap. After washing with saturated NaHCO$_3$ solution and saturated NaCl solution, the solvent is concentrated under reduced pressure. Excess benzaldehyde is removed by heating at 100° C. at 0.1 mm. The residue, III (65.2 g, 78%) is used without further purification.

Step D: 2-Phenyl-3-cyclopropyl-5-(hydroxymethyl)oxazolidine, IV

Prepared by the same procedure as III, starting with II (69.0 g, 0.52 m), benzaldehyde (200 ml, 1.98 m) and benzoic acid (3 g) in toluene (110 ml). The product, IV is distilled at 130°–135° C. at 0.2 mm (53.9 g, 47%).

2-Phenyl-3-isopropyl-5-(hydroxymethyl)oxazolidine, 2-phenyl-3-(2-phenylethyl)-5-(hydroxymethyl)oxazolidine and 2-phenyl-3-(4-phenyl-2-butyl)-5-(hydroxymethyl)oxazolidine were prepared in the same manner as compound III using isopropylamine, 2-phenylethylamine and 4-phenyl-2-butylamine in place of 2-(3,4-dimethoxyphenyl)ethylamine.

Step E: 2-{p-[[3-[2-(3,4-Dimethoxyphenyl)ethylamino]-2-hydroxypropoxy]]phenyl}-4-(2-thienyl)imidazole dihydrochloride, V A solution of III (15.0 g, 0.044 m) in pyridine (17 ml) is cooled to 10° C. and p-toluenesulfonyl chloride (8.39 g, 0.044 m) is added over 30 minutes, keeping the temperature below 25° C. After stirring at 25° C. for 3 hours, a cold solution of K$_2$CO$_3$ (6.08 g, 0.044 m) in H$_2$O (40 ml) is added and the mixture is extracted with CHCl$_3$ (3×75 ml). The extracts are washed with H$_2$O, dried and concentrated under reduced pressure below 50° C., initially using water aspiration and finally high vacuum to yield the tosylate a (21.6 g, 99%). Sodium hydride (1.97 g, 0.041 m, 50% dispersion in mineral oil) is added to a solution of 2-(p-hydroxyphenyl)-4-(2-thienyl)imidazole (9.93 g, 0.04 (1 m) in dimethylformamide (73 ml) under nitrogen and the mixture is heated at 60° C. for 30 minutes. A solution of the tosylate (21.6 g, 0.043 mole) in dimethylformamide (65 ml) is added and the mixture is refluxed for 17 hours. The solvent is distilled under reduced pressure, saturated sodium carbonate solution (125 ml) is added and the mixture is extracted with ethyl acetate (2×150 ml) and CHCl$_3$ (2×150 ml). The combined organic layers are dried and concentrated under reduced pressure. The residue is heated on a steam bath for 1.5 hours with 1.5N HCl (400 ml), cooled and extracted with ether (2×200 ml). The acid layer is rendered alkaline with 20% NaOH solution and extracted with CHCl$_3$ (3×250 ml). The solvent is evaporated under reduced pressure and the residue is chromatographed on silica gel and eluted with 5% MeOH-CHCl$_3$ saturated with NH$_3$. The product is isolated as the dihydrochloride salt and recrystallized from EtOH to give V (0.83 g, mp 278°–280° C.).

Anal. Calc'd. for C$_{26}$H$_{29}$N$_3$O$_4$S.2 HCl: C, 56.52; H, 5.66; N, 7.61.

Found: C, 56.57; H, 5.84; N, 7.46.

Step F: Using 2-phenyl-2isopropyl-5-(hydroxymethyl)oxazolidine, 2-phenyl-3-(2-phenylethyl)-5-(hydroxymethyl)oxazolidine and 2-phenyl-3-(4-phenyl-2-butyl)-5-hydroxymethyl)oxazolidine in place of III in Step C gave the following products:

2-{p-[3-isopropylamino-2-hydroxypropoxyl]phenyl}-4-(2-thienyl)imidazole; m.p. 172°–174° C.;

2-{p-[3-(2-phenylethyl)amino-2-hydroxypropoxy]phenyl}-4-(2-thienyl)imidazole-dihydrochloride; m.p. 274°–276° C.;

2-{p-[3-(4-phenyl-2-butyl)amino-2-hydroxypropoxy]phenyl}-4-(2-thienyl)imidazole dihydrochloride; m.p. 156°–166° C.

EXAMPLE B

4-Methyl-2-[p-[[3-[2-(3,4-dimethoxyphenyl)ethylamino]-2-hydroxypropoxy]]-phenyl]imidazole dihydrochloride hemihydrate, VI VI was prepared by essentially the same procedure as in Example A, starting with III (18.0 g, 0.052 m) and 2-(p-hydroxyphenyl)-4-methylimidazole (8.36 g, 0.048 m). The product is isolated as the dihydrochloride salt and recrystallized from EtOH-ether to yield VI (2.07 g, m.p. 224°–227° C.).

Anal. Calc'd. for C$_{23}$H$_{29}$N$_3$O$_4$.2 HCl.0.5 H$_2$O: C, 55.98; H, 6.54; N, 8.52; Cl, 14.37.

Found: C, 55.87; H, 6.62; N, 8.32; Cl, 14.23.

EXAMPLE C

2-[p-(3-Cyclopropylamino-2-hydroxypropoxy)phenyl]-4-(2-thienyl)imidazole, VII A solution of IV (6.80 g., 0.031 m) in pyridine (12 ml) is cooled to 10° C. and p-toluenesulfonyl chloride (5.91 g., 0.031 m) is added over 30 minutes, keeping temperature below 25° C. After stirring at 25° C. for 3 hours, a cold solution of K$_2$CO$_3$ (4.28 g., 0.031 m) in H$_2$O (28 ml) is added and the mixture is extracted with CHCl$_3$ (3×50 ml). The extracts are washed with H$_2$O, dried and concentrated under reduced pressure below 50° C., initially using water aspiration and finally high vacuum to yield the tosylate a (11.27 g, 97%). Sodium hydride (1.39 g, 0.029 m, 50% dispersion in mineral oil) is added to a solution of 2-(p-hydroxyphenyl)-4-(2-thienyl)imidazole (7.00 g, 0.029 m) in dimethylformamide (50 ml) under nitrogen and the mixture is heated at 60° C. for 30 minutes. A solution of the tosylate (11.27 g, 0.030 m) in dimethylformamide (45 ml) is added and the mixture is refluxed for 16 hours. The reaction mixture is poured into H$_2$O (300 ml) and extracted with ether (3×150 ml). The combined organic layers are extracted with cold 1N (3×75 ml) and the acid layer added to sodium acetate (18.5 g, 0.23 m) and stirred at 25° C. for 5 hours. The solution is extracted with ether (2X), basified with saturated Na$_2$CO$_3$ solution, extracted with 10% MeOH-CHCl$_3$ (3×150 ml), dried and concentrated under reduced pressure. The residue is chromatographed on silica gel and eluted with 5% MeOH-CHCl$_3$ saturated with NH$_3$. The product VII is crystallized from CH$_3$CN (0.43 g., mp 169°–171.5° C.).

Anal. Calc'd. for C$_{19}$H$_{21}$N$_3$O$_2$S: C, 64.20; H, 5.96; N, 11.82.

Found: C, 63.90; H, 5.91; N, 11.71.

The dihydrochloride salt melts at 241.5°–243.5° C. after recrystallization from EtOH.

Anal. Calcd. for C$_{19}$H$_{21}$N$_3$O$_2$S.2 HCl: C, 53.27; H, 5.41; N, 9.81.

Found: C, 53.09; H, 5.45; N, 9.73.

EXAMPLE D

2-[p-(3-Cyclopropylamino-2-hydroxypropoxy)phenyl]-4-methylimidazole, VIII

Prepared by essentially the same procedure as VII, starting with III (32.08 g, 0.146 m) and 2-(p-hydroxyphenyl)-4-methylimidazole (24.4 g, 0.14 m). The free base VIII (1.44 g) is recrystallized from CH$_3$CN. An analytical sample melts at 150.5°–153.5° C.

Anal. Calcd. for C$_{16}$H$_{21}$N$_3$O$_2$: C, 66.87; H, 7.37; N, 14.62.

Found: C, 66.63; H, 7.45; N, 14.25.

The dihydrochloride salt melts at 244.5°–245.5° C. (d) after recrystallization from EtOH.

Anal. Calcd. for C$_{16}$H$_{21}$N$_3$O$_2$.2 HCl: C, 53.34; H, 6.43; N, 11.66.

Found: C, 53.37; H, 6.59; N, 11.38.

EXAMPLE E

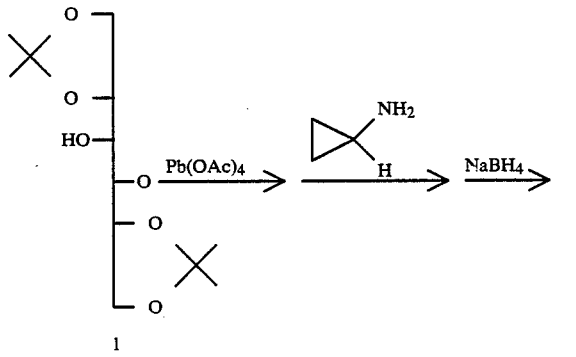

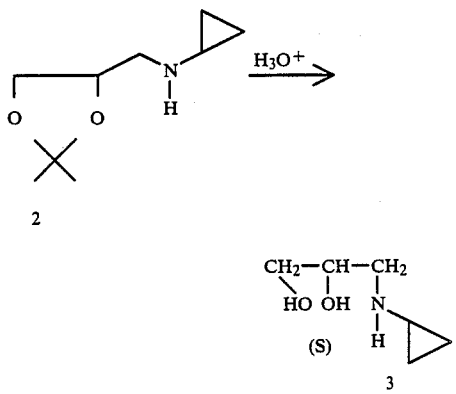

(a) (S) 3-cyclopropylamino-1,2-propanediol(3)

To an ice cooled solution of 1 (96 g., 0.37 mol) in THF (450 ml.) was added portionwise with stirring dry Pb(OAc)$_4$ (164 g, 0.37 mol) while maintaining the temperature below 10° C. The solution was stirred for 30 minutes at 0°–5° C. and additional 30 minutes at room temperature. The mixture was filtered through Super-Cel, the pad washed with THF and the cooled yellow solution treated with cyclopropylamine (96 ml, 79 g, 1.38 mol). After the addition, the reaction mixture was stirred for one hour at room temperature, cooled to 0°, and a solution of NaBH$_4$ (28 g, 0.74 mol) in EtOH (800 ml) was added with vigorous stirring while keeping the temperature below 10° C. After the addition, the mixture was stirred for 1½ hours at room temperature, 4% NaOH (500 ml) added and the pH adjusted to 9.4 with solid NH$_4$Cl. The mixture was filtered and the filtrate was concentrated to remove the organic solvents. The aqueous layer was extracted with CH$_2$Cl$_2$ (7X). The organic extracts were dried, filtered and concentrated to dryness to yield 121 g of 2. Crude 2 was treated with cold 1N HCl (800 ml) and stirred at room temperature for 2 hours. The solution was then neutralized with solid K$_2$CO$_3$ and saturated with NaCl. The resulting solution was continuously extracted with CHCl$_3$ for 5 days to yield 3. After distillation bp$_{0.3}$ 95°–100°C., 46.7 g. of 3 (48%) were obtained; $^1$H NMR (CDCl$_3$) 0.4 (4H, m), 2.15 (1H, m), 2.75 (2H, m), 3.6 (6H, m); $\alpha_D^{25} = -30.7$ (1N HCl). C=1.22.

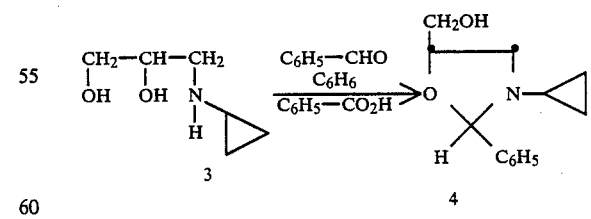

(b) (S) 2-phenyl-3-cyclopropyl-5-hydroxymethyloxazolidine (4)

A solution of 3 (46 g, 0.35 ml), benzoic acid (1.5 g), benzaldehyde (120 ml) and C$_6$H$_6$ (75 ml) was heated to reflux while collecting the H$_2$O in a Dean-Stark trap.

After 1 hour, a theoretical amount of H₂O was collected and the solution was poured into cold H₂O (200 ml) containing NaHCO₃ (9 g) and NaCl (24 g). The layers were separated and the aqueous layer extracted with CHCl₃ (2X). The combined extracts were dried, filtered concentrated to dryness, and the residue distilled at bp$_{0.3}$ 125°–130° C. to yield 57.4 g (75%) of 4; ¹H NMR (CDCl₃) 0.25 (4H, m), 1.8 (1H, m), 3.05 (3H, m), 3.7 (2H, m), 4.25 (1H, m), 5.1 (1H, d), 7.3 (5H, bs).

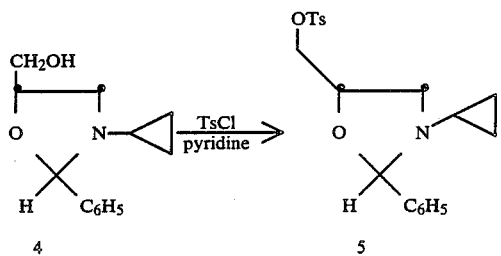

(c) (S) 2-phenyl-3-cyclopropyl-5-hydroxymethyloxazolidine-5-(p-methylphenylsulfonate) (5)

To a solution of 4 (72 g, 0.33 mol) in C₅H₅N (145 ml) was added portionwise p-toluenesulfonylchloride (63 g, 0.33 mol) while maintaining the temperature below 10° C. After completion of this addition, the mixture was maintained at −5° to 0° C. After 4 hours, a cold solution of K₂CO₃ (46 g, 0.33 mol) in H₂O (285 ml) was added and the mixture extracted with CHCl₃ (3X). The organic extracts were dried, filtered and concentrated to dryness to yield a quantitative yield of 5; ¹H NMR (CDCl₃) 0.25 (4H, m), 1.85 (1H, m) α 4 (3H, s), 3.15 (2H, m), 4.1 (3H, m), 5.05 (1H, s), 7.4 (9H, m)

ring. After 15 minutes, a solution of 5 (123 g, 0.33 mol) in DMF (200 ml) was added dropwise. After the addition, the reaction mixture was heated at 120° C. for 18 hours. The mixture was then poured onto ice and extracted with EtOAc (4X). The organic layer was washed with solid Na₂-CO₃, H₂O, dried, filtered and concentrated to dryness. The residue was stirred in H₂O (1 l) and AcOH (80 ml). After stirring at room temperature overnight, the solution was extracted with EtOAc (2X) and the aqueous layer poured into saturated Na₂-CO₃. The basic solution was then extracted with CHCl₃ (4X) and the organic layer dried, filtered and concentrated to dryness to yield 50 g of crude 7 which were added to a solution of 8 (0.21 mol) in H₂O (210 ml) along with CH₃OH (800 ml) and 28% aqueous NH₃ (270 ml). The mixture was stirred at room temperature overnight and then the CH₃OH was removed under reduced pressure. The resulting aqueous layer was basified with saturated Na₂CO₃ and extracted with CHCl₃ (4X). The organic layers were dried, filtered and concentrated to dryness. The residue was chromatographed on silica gel and the product eluted with 5% CH₃OH-CH₂Cl₂ saturated with NH₃. The product was crystallized from H₃CCN to yield 14.2 g of 9. Recrystallization from H₃CCN yielded 13.7 g of 9 (25%); mp 169°–171° C.;

$a_D{}^{25} = -11.83°$ C. = 1.851 (1N HCl); ¹H NMR (CDCl₃) 0.3 (4H, m), 2.05 (1H, m), 2.7 (2H, m), 3.9 (3H, m), 7.0 (2H, d), 7.85 (3H, d and s).

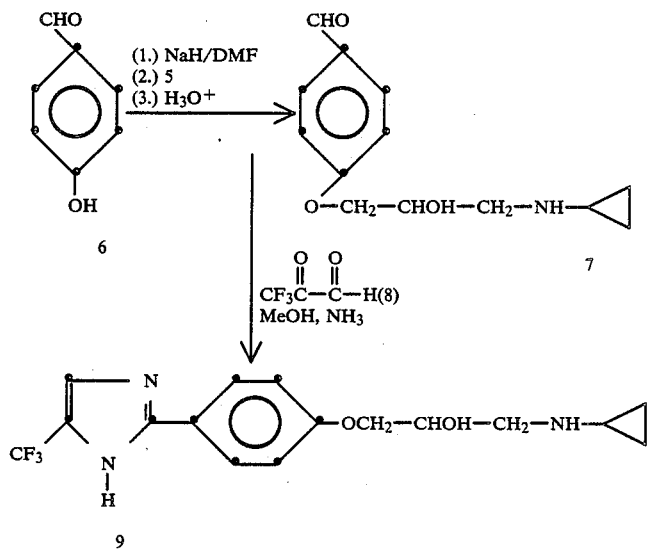

(d) (S) 2-[4-(3-cyclopropylamino-2-hydroxypropoxy)phenyl]-4-trifluoromethylimidazole (9)

To a suspension of NaH (60% oil dispersion, 15.2 g, 0.38 mol) in DMF (350 ml) under N₂ was added 6 (40.3 g, 0.33 mol) and the mixture heated at 70° C. with stir-

EXAMPLE F

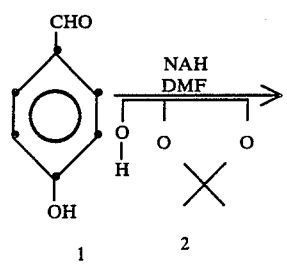

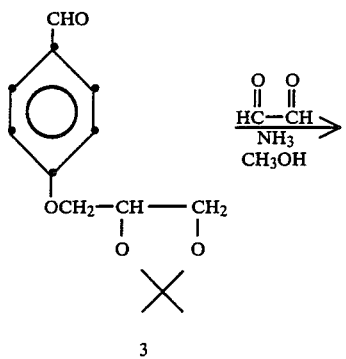

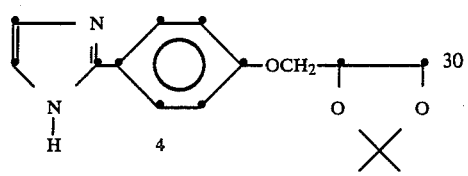

(a) p-(2-imidazolyl)phenoxy-1,2-propanediol acetonide 4

To a suspension of NaH (60% oil dispersion, 10 g, 0.25 mol) in DMF (50 ml) was added dropwise under N₂ at 70° C. a solution of 1 (28 g, 0.23 mol) in DMF (150 ml). After 15 minutes at 70° C., a solution of 2 (45.5 g, 0.22 mol) in DMF (50 ml) was added dropwise. After heating on a steam bath for 18 hours, H₂O was added and the solution extracted with EtOAc (3X). The combined extracts were washed with H₂O (2X), saturated NaCl, dried, filtered and concentrated to dryness to yield crude 3. To 3 was added CH₃OH (500 ml), 40% glyoxal (100 ml) and 28% concentrated aqueous NH₃. After stirring overnight at room temperature, the CH₃OH was removed under reduced pressure, H₂O added to the residue and the aqueous solution extracted with CHCl₃ (4X). The combined extracts were dried, filtered and concentrated to dryness. The residue was chromatographed on silica gel and the product eluted with 10% CH₃OH-CHCl₃ to yield 4. Concentration of the solvent and trituration with hexane yielded 18 g of 4. The product was crystallized from toluene-ligroin to yield 13 g of 4 (22%), mp 148°-150°; ¹H NMR (DMSO-d₆) δ 1.35 (6H, d), 4.0 (5H, m), 6.95 (2H, d), 7.05 (2H, s), 7.8 (2H, d).

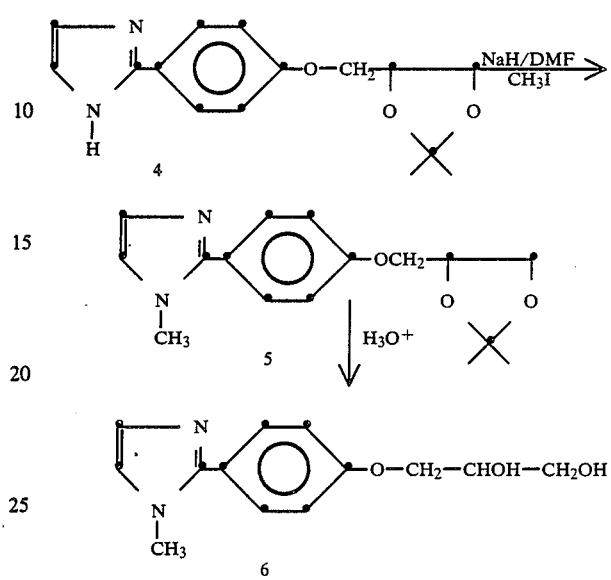

(b) 3-(p-(N-methyl-2-imidazolyl)phenoxyl)-1,2-propanediol 6

Into a flamed out flask under N₂ was added NaH (60% oil dispersion, 6.0 g, 0.15 mol), DMF (750 ml) and 4 (41.6 g, 0.15 mol). The solution was cooled to 0°-5° C. and a solution of CH₃I (23.4 g, 10.2 ml, 0.165 mol) in DMF (75 ml) was added. The reaction mixture was stirred overnight while allowing the ice bath to attain room temperature. After 18 hours, the reaction mixture was poured in H₂O (3 l) and extracted with EtOAc (4X).

The combined extracts were washed with H₂O, saturated NaCl, dried, filtered and concentrated to dryness to yield 5. 5 ¹H NMR (CDCl₃) δ 1.45 (6H, d), 3.6 (3H, s), 4.0 (5H, m), 6.95 (4H, d, 2S), 7.5 (2H, d). The residue was treated with 3N HCl (200 ml), and acetone (200 ml) heated on a steam bath for ½ hour, cooled, extracted with EtOAc (2X), and poured onto solid K₂CO₃. The saturated aqueous solution was extracted with CHCl₃, (4X). The combined extracts were dried, filtered and concentrated to dryness. The residue was triturated with Et₂O to yield 23.4 g of 6 (65%).

6 ¹H NMD D(DMSO-d₆) δ 3.4 (2H, m), 3.65 (3H, s), 3.9 (3H, m), 4.8 (2H, exch), 7.0 (1H, s), 7.1 (2H, d), 7.2 (1H, s), 7.6 (2H, d).

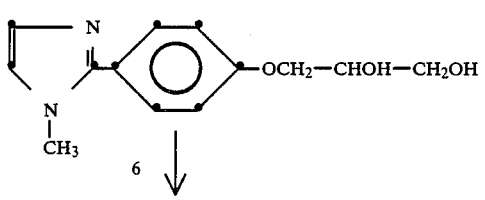

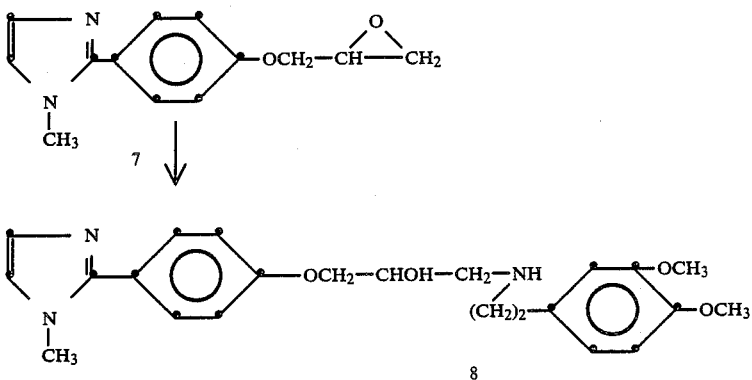

(c)
3-(p-(N-methyl-2-imidazolyl)phenoxy)-1,2-epoxypropane (7)

Into a flask under $N_2$ was placed 6 (7.0 g, 0.03 mol), pyridine (20 ml), pyridine·HCl (3.9 g, 0.034 mol) and the mixture cooled in an ice bath. To the cooled mixture was added methanesulfonyl chloride (3.26 g, 2.2 ml, 0.028 mol). After 10 minutes, $Et_2O$ (130 ml) $NaOCH_3$ (19 g, 0.35 mol), and $CH_3OH$ (65 ml) were added and the suspension stirred for ½ hour. Water was added and the layers were separated. The aqueous layer was further extracted with $CH_2Cl_2$ (3X). The combined extracts were washed with $H_2O$, saturated NaCl, dried, filtered and concentrated to dryness to yield 7; $^1H$ NMR ($CDCl_7$) δ 2.8 (2H, m), 3.3 (1H, m), 3.65 (3H, s), 4.1 (2H, m), 7.4 (6H, m).

(d)
2-[p-[[3-[2-(3,4-dimethoxyphenyl)ethylamino]]-2-hydroxypropoxy]phenyl]-N-methyl imidazole, 2 HCl (8)

Compound 7 was dissolved in isopropanol (45 ml) and a solution of 3,4-dimethoxyphenethylamine (4.5 g, 0.025 ml) was added dropwise. After the addition the solution was heated with stirring at 70° C. After 18 hours, the solution was concentrated to dryness. The residue was chromatographed on silica gel and the product eluted with $CHCl_3$ saturated with $NH_3$. The product was crystallized from HCl/EtOH and recrystallized from isopropanol to yield 2.7 g of 8, mp 192°–194° C; $^1H$ NMR (DMSO-$d_6$) δ 3.05 (6H, m), 3.7 (6H, d), 3.85 (3H, s), 4.3 (3H, m), 6.8 (3H, m), 7.2 (2H, d), 7.8 (4H, m).

EXAMPLE G

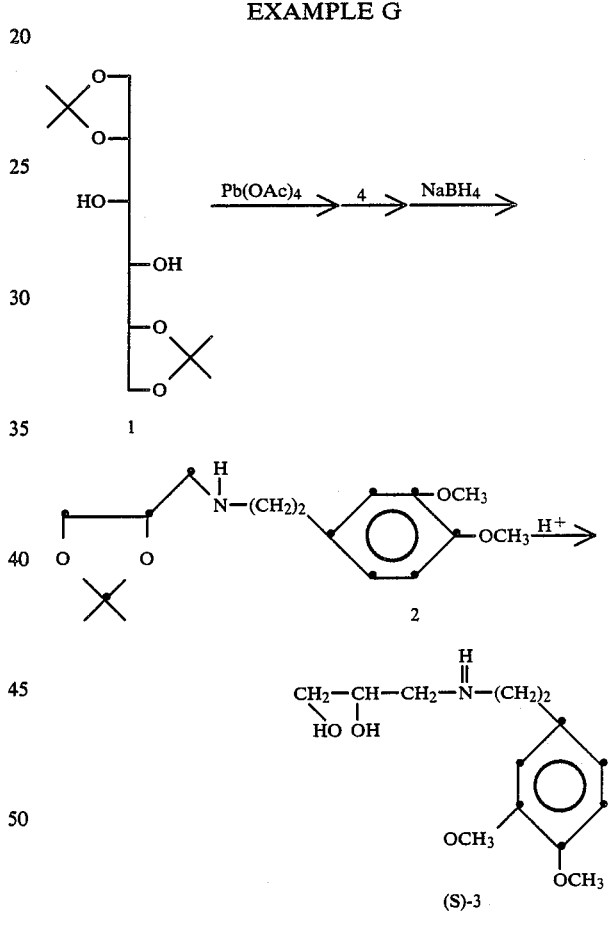

(a) (S)
3-[2-(3,4-dimethoxypheny)ethylamino]-1,2-propanediol (3)

To an ice cooled solution of 1 (128.7 g, 0.49 mol) in THF (650 ml) was added portionwise with stirring dry Pb(OAc)$_4$ (220 g, 0.5 mol) while maintaining the temperature below 10° C. The solution was stirred for 30 minutes at 0°–5° C. and an additional 30 minutes at room temperature. The mixture was filtered through Super-Cel, the pad washed with THF (500 ml.) and the yellow cooled solution treated with 3,4-dimethoxyphenethylamine 4 (331 g, 1.8 mol). After the addition, the thick suspension was stirred for 1 hour at room temperature, cooled to 0°, and a solution of NaBH₄, (13.1 g, 0.34 mol) in 9% NaOH (600 ml) was added with vigorous stirring while keeping the temperature below 10° C. After the addition stir for ½ hour at 0°–4°, 1½ hour at room temperature, and then the pH of the solution adjusted to 9.4 with solid NH₄Cl. The organic solvents were concentrated and the resulting solution extracted with CHCl₃ (3X). The combined extracts were dried, filtered and concentrated to dryness to yield 482 g of 2. Crude 2 was treated with cold 2N HCl (1 l) and stirred at room temperature. After 18 hours, the solution was neutralized with solid K₂CO₃, extracted with EtOAc, and saturated with solid NaCl. The resulting solution was continuously extracted for 5 days with CHCl₃ to yield 360 g of 3 and 4. The residue was chromatographed on silica gel and eluted with 5% MeOH-CHCl₃ saturated with NH₃ to yield 138.3 g of 4 (90% recovery) and then with 10–20% MeOH-CHCl₃ saturated with NH₃ to yield 195 g of 3 (77%). The residue triturated with hexane yielded a solid, mp=52°–56°, $[\alpha]_D^{25} = -16.48$ (1N HCl) C=2.055; ¹H NMR (CHCl₃) δ2.7 (6H, m), 3.0 (3H, bs), 3.6 (2H, bs), 3.8 (7H, d, m), 6.7 (3H, bs).

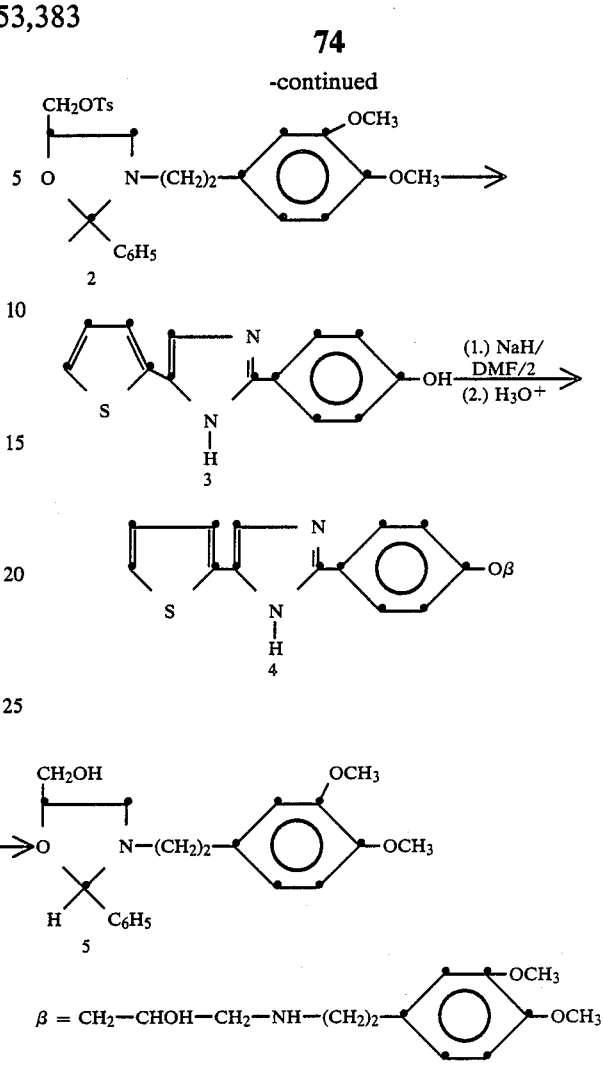

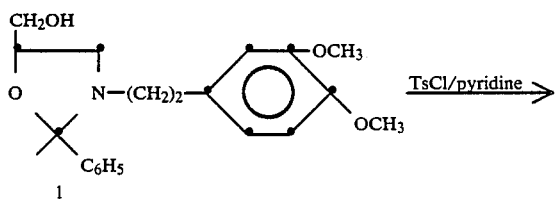

(b) (S) 2-phenyl-3-[2-(3,4-dimethoxyphenyl)ethyl]-5-hydroxymethyloxazolidine (5)

A solution of 3 (195 g, 0.76 mol), benzoic acid (3.0 g), benzaldehyde (270 ml), C₆H₆ (180 ml) was heated to reflux while collecting the H₂O in a Dean-Stark trap. After 2½ hours, 13 ml of H₂O was collected and the solution cooled, washed with saturated Na₂CO₃. The aqueous layer was washed with CHCl₃ (2X) and the combined extracts dried, filtered and concentrated to dryness to yield 232 g of 5 which contains 26 mol % benzaldehyde. This corresponds to 209 g of 5; ¹H NMR (CDCl₃) δ 2.6 (6H, m), 3.4 (2H, m), 3.75 (7H, d, m), 4.3 (1H, m), 4.8 (1H, d), 6.7 (3H, m), 7.4 (5H, bs).

(c) 2-phenyl-3-[2-(3,4-dimethoxyphenyl)ethyl]-5-hydroxymethyloxazolidine-5-(p-methylphenylsulfonate) (2)

To a solution of 1 (34.3 g, 0.1 mol) in pyridine (45 ml) cooled to 0°–5° C. was added portionwise p-toluenesulfonyl chloride (19.3 g, 0.1 mol) while maintaining the temperature below 30° C. After 3 hours at 0°–5° C., CHCl₃ was added and the solution washed with saturated Na₂CO₃. The aqueous layer was further extracted with CHCl₃ (2X) and the combined extracts dried over Na₂SO₄, filtered and concentrated first at 20 mm pressure and then at 1 mm while keeping the temperature below 50° C. to yield 2 as an oil.

(d) (S) 2-{p-[[3-[2-(3,4-dimethoxyphenyl)ethylamino]-2-hydroxypropoxy]]phenyl}-4-(2-thienyl)imidazole ·2HCl (4)

To a suspension of NaH (60% oil dispersion, 4.8 g, 12 mol) in DMF (120 ml) was added at 70° C. under N₂ a solution of 3 (23 g, 0.095 mol) in DMF (120 ml). After stirring for 15 minutes at 70° C. a solution of 2 in DMF (120 ml) was added dropwise. After the addition, the mixture was heated at 120° C. for 18 hours. The solution was then concentrated to dryness at 0.1 mm of pressure and the residue treated with AcOH (100 ml) 3N HCl (30 ml) and H2O (1 1). After stirring overnight, the solution was extracted with EtOAc (2X) and the aqueous layer adjusted to pH 10 with saturated Na2CO3 and extracted with CHCl3 (4X). The organic layers were dried, filtered and concentrated to dryness. The residue was chromatographed on silica gel and the product eluted with 5% MeOH-CHCl3 saturated with NH3 to yield 8.5 g of 4 which was crystallized from H3CCN to yield 5.5 g of 4 (11%); mp 127°-129° C.

The sample was converted to the dihydrochloride salt by crystallization from HCl-EtOH. Recrystallization from EtOH yielded 4 . 2 HCl; mp 269°-274° C.; $[\alpha]_D^{25} = -7.3$ C=1(H2O); 'H NMR (DMSO) δ 3.05 (7H, m, 1 exch), 3.7 (6H, d), 4.3 (5H, m, 1 exch), 6.83 (3H, bs), 7.2 (3H, m), 7.67 (1H, d), 7.97 (2H, bs), 8.37 (2H, d), 9.27 (2H, bs, exch).

In the above sequence, using (S) 2-phenyl-3-cyclopropyl-5-Hydroxymethyl-oxazolidine-5-(p-methylphenysulfonate in place of 2 gave (S) 2-(3-cyclopropylamino-2-hydroxypropoxy)-4-(2-thienyl)imidazole dihydrochloride instead of 4. $[\alpha]_D^{25} = -10.7°$, mp=238°-241°.

EXAMPLE H

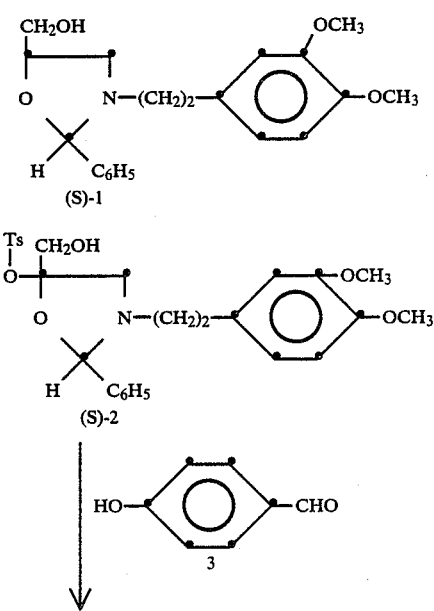

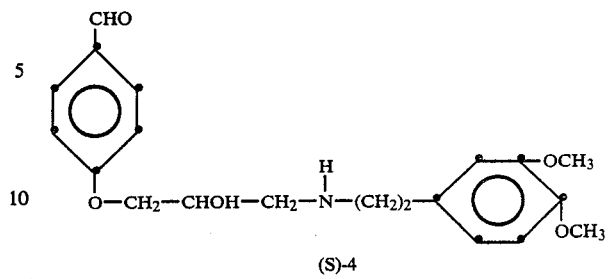

(a) To a solution of (S) 1 (10.3 g, 0.03 mol) in pyridine (15 ml) cooled to 0°–5° C. was added portionwise a solution p-toluenesulfonyl chloride (5.7 g, 0.03 mol) while maintaining the temperature below 30° C. After 4 hours at room temperature, CHCl3 was added and the solution washed with saturated Na2CO3. The aqueous layer was further extracted with CHCl3 (2X) and the combined extracts dried over Na2SO4, filtered and concentrated first at 20 mm pressure and then at 1 mm while keeping the temperature below 50° C. to yield (S) 2.

(b) (S) p-[3-[2-(3,4-dimethoxyphenyl)ethyl]-2-hydroxypropoxy]benzaldehyde (4)

To a suspension of NaH (60% oil dispersion, 1.2 g, 0.03 mol) in DMF (20 ml) was added at 70° C. under N2 a solution 3 (37 g, 0.03 ml) in DMF (30 ml). After stirring for 15 minutes at 70° C. a solution of (S) 2 in DMF (50 ml) was added dropwise. After the addition, the mixture was heated at 120° C. for 18 hours. The solution was then poured into H2O and extracted with EtOAc (3X). The organic extracts were washed with H2O (2X), saturated NaCl (1X), dried, filtered and concentrated to dryness. The residue was treated with H2O (250 ml) and AcOH (25 ml) and stirred overnight at room temperature. The solution was extracted with EtOAc (2X), neutralized with saturated Na2CO3 and extracted with CHCl3 (9X). The organic extracts were dried, filtered and concentrated to yield 8.5 g of 4; 'H NMR (CDCl3) δ 2.7 (6H, m), 3.8 (6H, s), 4.1 (3H, m), 6.7 (3H, bs), 6.95 (2H, d), 7.75 (2H, d).

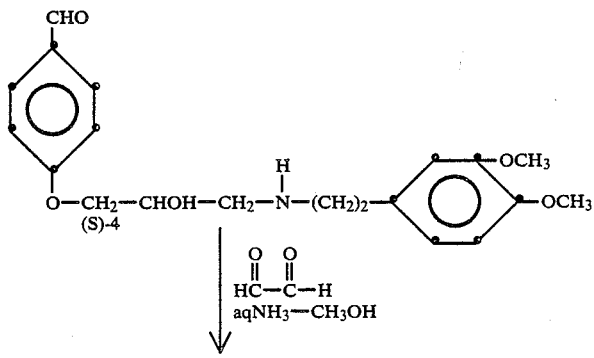

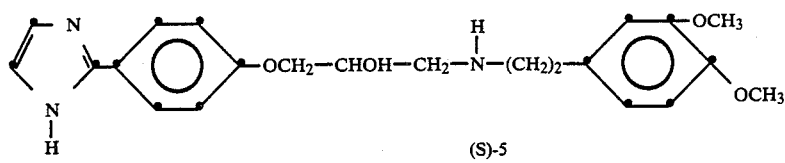

(S)-5

(c) (S) 2-[p-[[3-[2-(3,4-dimethoxyphenyl)ethylamino]-2-hydroxypropoxy]phenyl]imidazole·2 HCl.H2O] (5)

A mixture of (S) 4 (8.5 g, 0.024 mol), CH3OH (50 ml), 40% glyoxal (10 ml, 0.069 mol), 28% concentrated aqueous NH3 (15 ml) was allowed to stir at room temperature. After 18 hours, the CH3OH was removed under reduced pressure and water added (100 ml). The aqueous layer was extracted with CHCl3 (4X) and the organic layer dried, filtered and concentrated to dryness. The residue was chromatographed on silica gel and the product eluted with 2% CH3OH-CHCl3 saturated with NH3 to yield 3.0 g of (S) 5 which was converted to the dihydrochloride salt by crystallization from HCl-EtOH. Recrystallization from isoPrOH-CH3OH yielded 1.3 g of (S) 5 (11%); mp 223°–25° C.; $[\alpha]_D^{25} = -6.94$ (H2O) (C=0.502) H NMR (DMSO-d6) $\delta$ 3.2 (6H, m), 3.8 (6H, d), 4.2 (3H, d), 6.9 (3H, m), 7.25 (2H, d), 7.75 (2H, s), 8.35 (2H, d), 9.35 (2N, bs, exch).

EXAMPLE J

Preparation of 2-[[p-[3-[2-(3,4-Dimethoxyphenyl)ethylamino]-2-hydroxypropoxy]phenyl]]imidazole, III, and 2-[p-(3-Cyclopropylamino-2-hydroxypropoxy)phenyl]imidazole, IV

REACTION SCHEME FOR EXAMPLE J

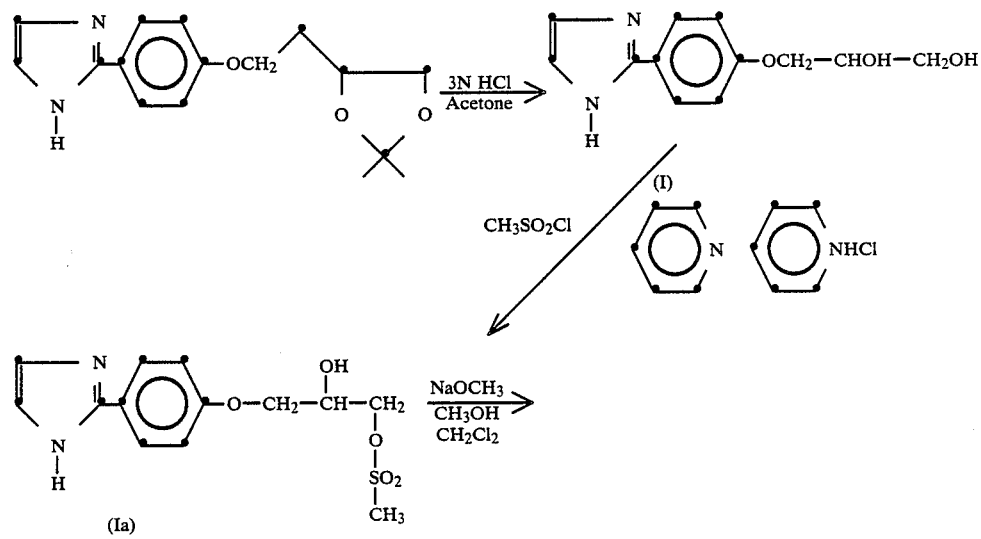

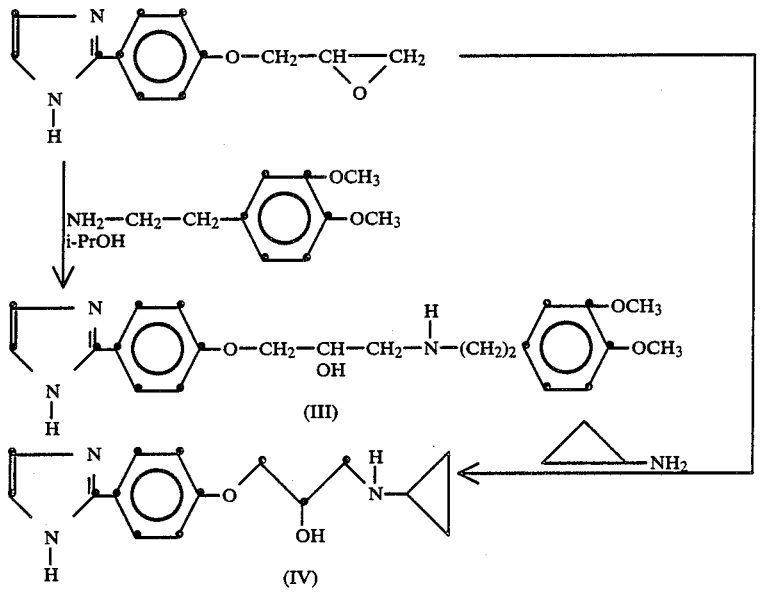

EXAMPLE J (a) 3-[p-(2Imidazolyl)phenoxyl-1,2-propanediol, I

A mixture of 3-[p-(2-imidazolyl)phenoxy]-1,2-propanediol acetonide (5.9 g, 0.022 m) in 3N HCl (45 ml) and acetone (45 ml) is refluxed for 0.5 hours. Acetone is removed under reduced pressure and the aqueous mixture is rendered alkaline with $K_2CO_3$. This solid is collected and dried in a vacuum oven at 55° to yield (I) (5.2 g, 100%, m.p. 165.5°–167°).

(b) 3-[p-(2-Imidazolyl)phenoxy]-1,2-epoxypropane, (II)

A mixture of 3-[p-(2-imidazolyl)phenoxy]-1,2-propanediol (15.19 g, 0.065 m), pyridine hydrochloride (8.2 g, 0.071 m) and pyridine (125 ml) is cooled in an ice-salt bath and stirred while methanesulfonyl chloride (7.45 g, 0.065 m) is added over 15 minutes. The mixture is stirred at room temperature for 1.5 hours, then a cold solution of $K_2CO_3$ (9.0 g, 0.065 m) in $H_2O$ (30 ml) is added and the mixture is concentrated at 50° under high vacuum. The residue is treated with another solution of $K_2CO_3$ (9.0 g) in $H_2O$ (50 ml) and slurried until a gummy solid forms. The crude monomesylate (Ia) is dried in the vacuum oven at 45° to yield a yellow solid weighing 18.34 g (90%).

The crude mesylate is suspended in a mixture of methanol (215 ml) and methylene chloride (215 ml) and cooled to 0° while a solution of sodium methoxide (3.51 g, 0.065 m) in methanol (40 ml) is added over 10 minutes with stirring. After stirring at 0° for 1.5 hours, $H_2O$ (100 ml) is added and the organic layer is separated. The aqueous layer is extracted with $CH_2Cl_2$ (250 ml) and the combined organic layers are dried and the solvent is concentrated under reduced pressure to yield (II) as a yellow solid (10.26 g, 73%) which is used without further purification.

(c) 2-{p-[[3-[2-(3,4-Dimethoxyphenyl)ethylamino]-2-hydroxypropoxy]phenyl}-imidazole, (III)

A mixture of 3-[p-(2-imidazolyl)phenoxy]-1,2-epoxypropane (1.00 g, 0.0046 m) and 2-(3,4-dimethoxyphenyl)ethylamine (1.25 g, 0.0069 m) in isopropanol (20 ml) is stirred at 70° for 19 hours. The solvent is evaporated under reduced pressure and the residue is chromatographed on silica gel, eluting with 5% MeOH-CHCl$_3$ saturated with NH$_3$. The free base III (0.58 g, 32%) is crystallized as the dihydrochloride salt from EtOH-MeOH-ether (m.p. 233.5°–23.5°).

Anal. Calcd. for $C_{22}H_{27}N_3O_4.2$ HCl: C, 56.17; H, 6.21; N, 8.93; Cl, 15.08.

Found: C, 55.89; H, 6.22; N, 8.55; Cl, 14.91.

(d) 2-[p-(3-Cyclopropylamino-2-hydroxypropoxy)phenyl]imidazole, (IV)

A mixture of 3-[p-(2-imidazolyl)phenoxy]-1,2-epoxypropane (4.95 g, 0.023 m) in cyclopropylamine (50 ml) is refluxed at 60° for 30 hours. The mixture is concentrated under reduced pressure and the residue is chromatographed on silica gel, eluting with 5–10% MeOH-CHCl$_3$ saturated with NH$_3$. The free base (IV) (1.21 g, 19%) is crystallized as the dihydrochloride salt from EtOH-MeOH-ether (m.p. 214°–5°).

Anal. Calcd. for $C_{15}H_{19}N_3O_2.2$ HCl: C, 52.03; H, 6.11; N, 12.14.

Found: C, 51.71; H, 6.24; N, 11.94.

EXAMPLE K
Preparation of 2-[p-[[3-[3-(3,4-Dimethoxyphenyl)-2-methyl-2-propylamino]-2-hydroxypropoxy]]phenyl]-4-(2-thienyl)imidazole, (VI), and 2-[p[[3-[3-(3,4-Dimethoxyphenyl)-2-propylamino]-2-hydroxypropoxy]]phenyl]-4-(2-thienyl)imidazole, (VII)
REACTION SEQUENCE
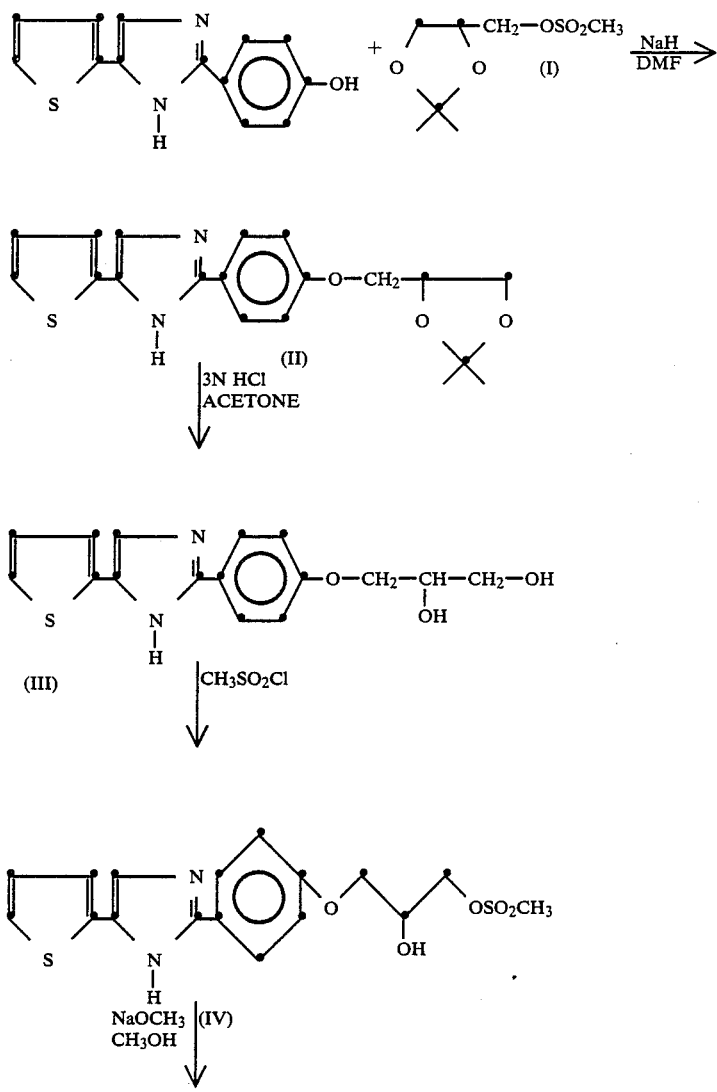

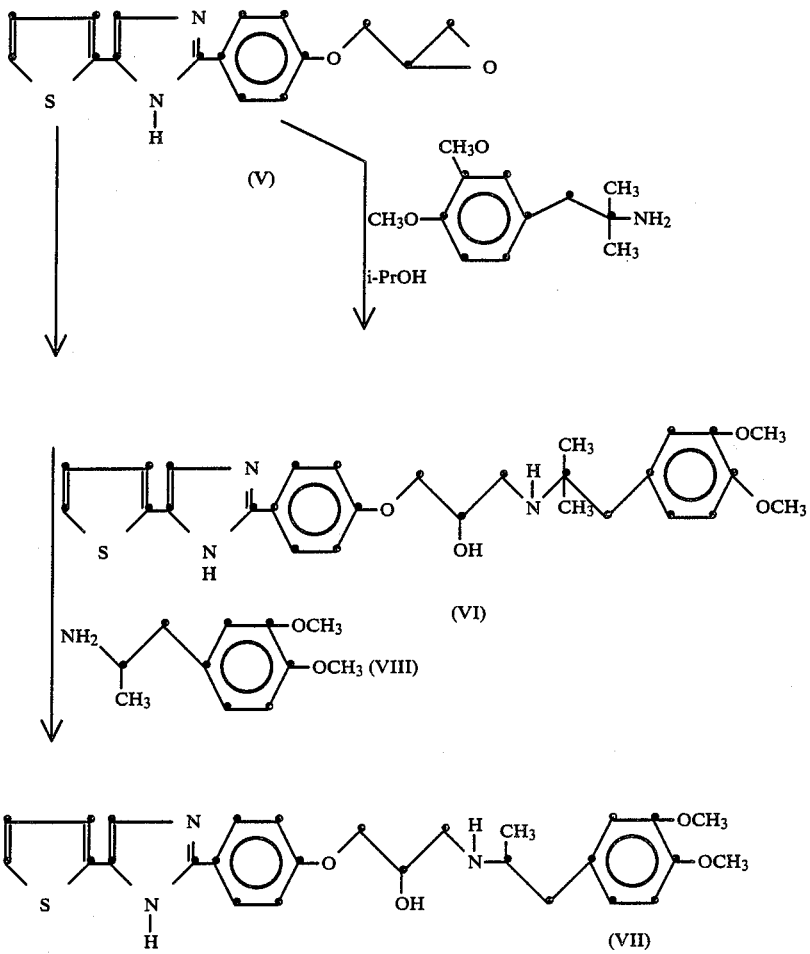

(a) 3-[p-[4-(2-Thienyl)-2-imidazolyl]phenoxy]-1,2-propanediol Acetonide, II

A solution of 2-(p-hydroxyphenyl)-4-(2-thienyl)imidazole (19.5 g, 0.08 m) in dimethylformamide (65 ml) is added to a stirred suspension of sodium hydride (4.8 g, 0.10 m, 50% dispersion in mineral oil) in dimethylformamide (20 ml) at 80° C. After stirring at 80° C. for 0.5 hours, a solution of 2,2-dimethyl-4-(hydroxymethyl)-1,3-dioxolane methanesulfonate, (I) (16.82 g, 0.08 m) in dimethylformamide (20 ml) is added rapidly and the mixture is stirred under nitrogen at 80° C. for 17 hours. The reaction mixture is poured into $H_2O$ (400 ml) and extracted with ether (3×350 ml). The combined extracts are washed with 5% NaOH solution (2×250 ml) and with $H_2O$ (3X), dried, and the solvent is evaporated under reduced pressure to yield crude (II) (14.22 g) which is used without further purification.

Using (R) I in place of I gave (R) II which was used without further purification.

(b) 3-[p-[4-(2-Thienyl)-2-imidazolyl]phenoxy]-1,2-propanediol, (III)

A mixture of 3-[p-[4-(2-thienyl)-2-imidazolyl]phenoxyl]-1,2-propanediol acetonide (14.15 g, 0.04 m) in 3N HCl (80 ml) and acetone (80 ml) is refluxed for 0.5 hours. Acetone is removed under reduced pressure and the aqueous mixture is rendered alkaline with $K_2CO_3$. The solid is collected and dried in a vacuum oven at 60° C. to yield (III) (10.38 g, 82%, m.p. 197°–200° C.).

Similarly using (R)-II in place of II gave (R) III, mp 200°–205° which was used directly.

(c) 3-[p-[4-(2-Thienyl)-2-imidazolyl]-phenoxy]-1,2-propanediol-1-methanesulfonate, (IV)

A mixture of 3-[p-[4-(2-thienyl)-2-imidazolyl]-phenoxy]-1,2-propanediol (10.3 g, 0.033 m), pyridine hydrochloride (4.28 g, 0.037 m) and pyridine (65 ml) is cooled in an ice bath and stirred while methanesulfonyl chloride (3.78 g, 0.033 m) is added over 10 minutes. The mixture is stirred at room temperature for 1.5 hours, then a cold solution of $K_2CO_3$ (4.56 g, 0.033 m) in $H_2O$ (22 ml) is added and the mixture is concentrated below 50° C. under high vacuum. The residue is chromatographed on silica gel, eluting with 10% MeOH-CHCl$_3$ to yield (IV) (4.52 g, 35%).

(d)
3[p-[4-(2-thienyl)-2-imidazolyl]phenoxy]-1,2-epoxypropane, (V)

A solution of 3-[p-[4-(2-thienyl)-2-imidazolyl]-phenoxy]-1,2-propanediol-1-methanesulfonate (4.45 g, 0.011 m) in methanol (40 ml) and methylene chloride (40 ml) is cooled in an ice bath while a solution of sodium methoxide (0.54 g, 0.010 m) in methanol (9 ml) is added over 10 minutes with stirring. After stirring at 0° C. for 1.5 hours, H$_2$O (165 ml) is added and the organic layer is separated. The aqueous layer is extracted with CH$_2$Cl$_2$ (2×175 ml) and the combined organic layers are dried and the solvent is concentrated under reduced pressure to yield (V) as an amorphous solid (3.37 g).

(e)
2-[p-[[3-[2-(3,4-Dimethoxyphenyl)-2-methyl-2-propylamino]-2-hydroxypropoxy]]phenyl]-4-(2-thienyl)imidazole, (VI)

A mixture of 3-[p-[4-(2-thienyl)-2-imidazolyl]-phenoxy]-1,2-epoxy-propane (1.76 g, 0.0084 m) and 3-(3,4-dimethoxyphenyl)-2-methylpropylamine in isopropanol (25 ml) and methanol (5 ml) is stirred at 70° C. for 16.5 hours. The solvent is evaporated under reduced pressure and the residue is chromatographed on silica gel, eluting with 10% MeOH-CHCl$_3$. The product is rechromatographed on silica gel, eluting with 3% MeOH-CHCl$_3$ saturated with NH$_3$ yielding 0.78 g (18%) of (VI) which is crystallized as the dihydrochloride salt from EtOH-MeOH-ether after treatment with decolorizing carbon (m.p. 241°-3° C.).
Anal. Calcd. for C$_{28}$H$_{33}$N$_3$O$_4$S.2HCl.H$_2$O: C, 56.18; H, 6.23; N, 7.02; Cl, 11.85.
Found: C, 56.40; H, 6.15; N, 7.06; Cl, 11.75.

Starting with (R) III combining steps c,d and e and substituting 2-[3,4-dimethoxy-phenylethylamine for 3-(3,4-dimethoxyphenyl-2-methyl-2-propylamine gave (R) 2-{p-[[3-[2-(3,4-dimethoxyphenylethyl)-amino]2-hydroxypropoxy]]phenyl}-4-(2-thienyl)-imidazole dihydrochloride m.p. 270°-272° C.

(f) 3-(3,4-Dimethoxyphenyl)-2-propylamine (VIII)

A mixture of 3,4-dimethoxyphenylacetone (51.1 g, 0.26 m) is dissolved in methanol (780 ml), sodium cyanoborohydride (11.3 g, 0.18 m) is added and the mixture is stirred at room temperature for 67 hours. The reaction mixture is adjusted to pH 2 with concentrated HCl and the solvent is evaporated under reduced pressure. The residue is dissolved in H$_2$O (250 ml), the aqueous layer is extracted with ether (3X) and then rendered alkaline with KOH and extracted with CH$_2$Cl$_2$ (3X). After drying, the solvent is evaporated under reduced pressure and the product is distilled at 112°-5°/0.5 mm to yield (VIII) (33.88 g, 67%).

(g)
2-[p-[[3-[2-(3,4-Dimethoxyphenyl)-2-propylamino]2-hydroxypropoxy]]phenyl]-4-(2-thienyl)-imidazole, (VIII)

A mixture of 3-[p-[4-(2-thienyl)-2-imidazolyl]-phenoxy]-1,2-epoxypropane (3.32 g., 0.011 m) and 3-(3,4-dimethoxyphenyl)-2-propylamine (2.93 g, 0.015 m) in isopropanol (30 ml.) and methanol (20 ml) is stirred at 70 ° C for 24 hours. The solvent is concentrated under reduced pressure and the residue is chromatographed on silica gel, eluting with 3% MeOH-CHCl$_3$ saturated with NH$_3$. The product (VII) is crystallized as a somewhat hygroscopic dihydrochloride salt from EtOH-ether after treatment with decolorizing carbon (m.p. 175°-9° C.).
Anal. Calcd. for C$_{27}$H$_{31}$N$_3$O$_4$S.2HCl: C, 57.24; H, 5.87; N, 7.42.
Found: C, 57.26 & 57.10; H, 6.00 & 6.00; N, 7.57 & 7.51.

EXAMPLE M
Alternate Synthesis of 2-[p-[[3-(3,4-Dimethoxyphenyl)-2-propylamino]-2-hydroxypropoxy]]phenyl]-4-(2-thienyl)-imidazole, (III)

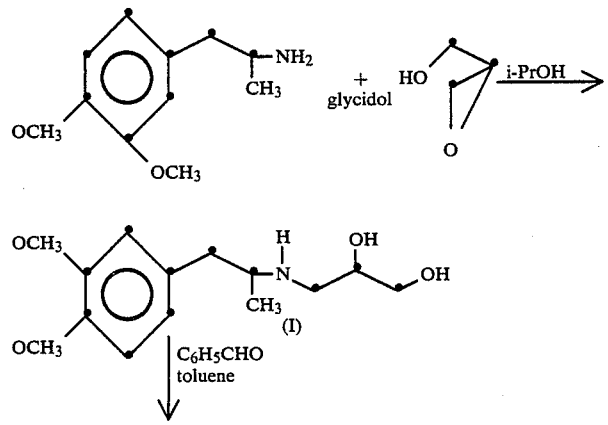

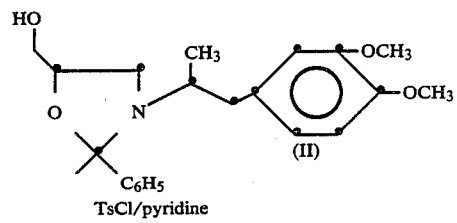

TsCl/pyridine

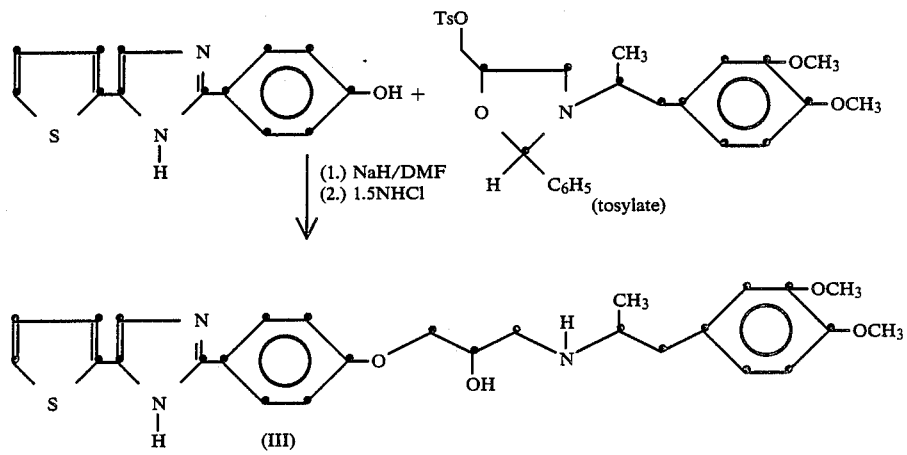

(tosylate)

(1.) NaH/DMF
(2.) 1.5NHCl

(a)
3-[3-(3,4-Dimethoxyphenyl)-2-propylamino]-1,2-propanediol, (I)

A solution of 3-(3,4-dimethoxyphenyl)-2-propylamine (20.0 g, 0.10 m) in isopropanol (20 ml) is heated to 50° C. while a solution of glycidol (5.0 g, 0.067 m) in isopropanol (5 ml) is added over 15 minutes. The mixture is stirred at 50° C. for 0.5 hours and then at 70° C. for 16 hours. The solvent is concentrated under reduced pressure and the residue is chromatographed on silica gel, eluting with 10% MeOH-CHCl$_3$ saturated with NH$_3$ to yield (I) weighing 14.37 g (80%).

(b)
3-[3-(3,4-Dimethoxyphenyl-2-propyl]-5-hydroxymethyl-2-phenyloxazolidine, (II)

A mixture of 3-[3-(3,4-dimethoxyphenyl)-2-propylamino]-1,2-propanediol (14.3 g, 0.053 m), benzaldehyde (12.7 g, 0.12 m) and benzoic acid (0.3 g) in toluene (45 ml) is refluxed for 3 hours, collecting the water formed in a Dean-Stark trap. After washing with saturated NaHCO$_3$ solution and with H$_2$O (2x), the solvent is distilled under reduced pressure. Excess benzaldehyde is distilled at 100° C. at 0.1 mm. The residue, (II) (16.88 g, 89%) is used without further purification in the next step.

(c)
2-[p-[[3-[3-(3,4-Dimethoxyphenyl)-2-propylamino]-2-hydroxypropoxy]]phenyl]-4-(2-thienyl) imidazole, (III)

A solution of 3-[3-(3,4-dimethoxyphenyl)-2-propylamino]-5-hydroxymethyl-2-phenyloxazolidine (11.08 g, 0.031 m) in pyridine (12 ml) is cooled to 10° C. and p-toluenesulfonyl chloride (5.91 g, 0.031 m) is added over 30 minutes with stirring, keeping the temperature below 25° C. After stirring at 25° C. for 3 hours, a cold solution of K$_2$CO$_3$ (4.28 g, 0.031 m) in H$_2$O (28 ml) is added and the mixture is extracted with CHCl$_3$ (3×55 ml). The extracts are washed with H$_2$O, dried and concentrated under reduced pressure below 50° C., initially using water aspiration and finally high vacuum to yield the tosylate (16.21 g, 100%). Sodium hydride (1.39 g, 0.029 m, 50% dispersion in mineral oil) is added to a solution of 2-(p-hydroxyphenyl)-4-(2-thienyl)-imidazole (7.00 g, 0.029 m) in dimethylformamide (52 ml) under nitrogen and the mixture is heated at 60° C. for 30 minutes. A solution of the tosylate (16.21 g, 0.031 m) in dimethylformamide (45 ml) is added and the mixture is heated at 120° C. for 20 hours. The solvent is distilled under reduced pressure, saturated Na$_2$CO$_3$ solution (100 ml) is added and the mixture is extracted with ethyl acetate (2×125 ml) and CHCl$_3$ (2×125 ml). The combined organic layers are washed with H$_2$O, dried and concentrated under reduced pressure. The residue is heated on a steam bath for 1.5 hours in 1.5 N HCl (280 ml), cooled and extracted with ether (2×150 ml). The acid layer is rendered alkaline with 20% NaOH solution and extracted with CHCl$_3$ (3×200 ml). The solvent is concentrated under reduced pressure and the residue is chromatographed on silica gel, eluting with 5% MeOH-CHCl$_3$ saturated with NH$_3$. The product (III) is crystallized as the dihydrochloride salt from EtOH-ether (m.p. 170.5°–173.5° C.).

Additional compounds which were prepared using the processes substantially as described above are tabulated below in Table III:

TABLE III
Additional Compounds of the Formula

R—C(=N-R1)(N(R2))—[phenyl with Rc]—O—CH$_2$—CHOH—CH$_2$—NHR$_6$

| | R | R$_1$— | R$_2$— | R$_c$— | R$_6$— |
|---|---|---|---|---|---|
| (a) | H | 2-thienyl | H | H | (CH$_2$)$_2$C$_6$H$_5$ |
| (b) | " | " | " | " | (CH$_2$)$_2$—(3,4-diOCH$_3$—C$_6$H$_3$) |
| (c) | " | " | " | " | cyclopropyl |
| (d) | " | " | " | " | isopropyl |
| (e) | " | " | " | " | n-propyl |
| (f) | " | " | " | " | C(CH$_3$)$_2$—CH$_2$—(3,4-diOCH$_3$—C$_6$H$_3$) |
| (g) | " | " | " | " | CH(CH$_3$)—CH$_2$—(3,4-diOCH$_3$—C$_6$H$_3$) |
| (h) | " | " | " | " | t-butyl |
| (i) | " | CH$_3$ | " | " | (CH$_2$)$_2$—(3,4-diOCH$_3$—C$_6$H$_3$) |
| (j) | " | " | " | " | cyclopropyl |
| (k) | " | H | " | " | (CH$_2$)$_2$—(3,4-diOCH$_3$—C$_6$H$_3$) |
| (l) | " | " | " | " | cyclopropyl |
| (m) | " | " | CH$_3$ | " | (CH$_2$)$_2$—(3,4-diOCH$_3$—C$_6$H$_3$) |
| (n) | " | " | H | OCH$_3$ | " |
| (o) | " | " | " | Br | " |
| (p) | " | CH$_3$ | " | OCH$_3$ | " |
| (q) | " | t-butyl | " | H | " |
| (r) | " | isopropyl | " | " | " |
| (s) | C$_1$–C$_6$alkyl | CH$_3$ | " | " | " |
| (t) | " | " | " | OCH$_3$ | " |
| (u) | halo | " | " | H | " |
| (v) | " | " | " | OCH$_3$ | " |

EXAMPLE I

2-{p-[3-(2-Ethoxyethyl)amino-2-hydroxypropoxy]-phenyl}-4-(2-thienyl)imidazole (3) and (S-3)

Step A: 3-(2-Ethoxyethyl)amino-1,2-propanediol (1)

A solution of glycidol (15 g, 0.2 mol) in isopropanol (50 ml) was added dropwise under N$_2$ at 70° C. to a solution of 2-ethoxyethylamine (53 g, 0.6 mol) in isopropanol (125 ml). After 15 hours, the isopropanol was removed under reduced pressure (20 mm) and the residue distilled at 120°-5° C. at 0.4 mm to yield 22.6 g (69%) of 1.

Step B: 2-Phenyl-3-(2-ethoxyethyl)-5-(hydroxymethyl)-oxazolidine (2)

A solution of 1 (22.6 g, 0.14 mol), toluene (120 ml), benzaldehyde (48 g, 0.45 mol) and benzoic acid (0.5 g) was heated at reflux with a Dean-Stark trap. After 1.5 hours, the theoretical amount of H$_2$O was collected, the reaction mixture was cooled to room temperature and added to saturated Na$_2$CO$_3$. The aqueous layer was separated and washed with CHCl$_3$ (3X). The combined extracts were dried, filtered, and concentrated to dryness. The residue was distilled at 145°-50° C. at 0.4 mm to yield 26 g (75%) of 2.

Step C: 2-{p-[3-(2-Ethoxyethyl)amino-2-hydroxypropoxy]-phenyl}-4-(2-thienyl)imidazole (3)

A solution of 2 (5.5 g, 0.022 mol) in pyridine (25 ml) was cooled in an ice bath and p-toluenesulfonyl chloride (4.2 g, 0.022 mol) was added while keeping the internal temperature below 30° C. After stirring for 3 hours at room temperature, saturated Na$_2$CO$_3$ was added and the mixture extracted with CHCl$_3$ (3X). The organic extracts were dried, filtered and concentrated under reduced pressure below 50° C. initially at 20 mm pressure and then under high vacuum to yield the tosylate of 2.

Under N$_2$, NaH (60% oil dispersion, 1 g, 0.025 mol) was added to DMF (20 ml) and heated at 70° C. while a solution of 2-(4-hydroxyphenyl)-4-(2-thienyl)imidazole (5.0 g, 0.021 mol) in DMF (40 ml) was added dropwise. After heating at 70° C. for 0.5 hours, a solution of the tosylate of 2 (0.022 mol) in DMF (25 ml) was added dropwise and the mixture heated at 110° C. After 18 hours, the reaction mixture was poured into H$_2$O and the suspension extracted with EtOAc (4X). The organic extracts were washed with H$_2$O, saturated NaCl, dried, filtered and concentrated to dryness. The residue was treated with AcOH (25 ml) and H$_2$O (175 ml) and the mixture stirred at room temperature. After 18 hours, the aqueous layer was extracted with Et$_2$O (2X), adjusted to ph>10 with saturated Na$_2$CO$_3$ and extracted with CHCl$_3$ (3X). The CHCl$_3$ extracts were dried, filtered and concentrated to dryness. The residue was chromatographed on silica gel eluting with 5% CH$_3$OH—CHCl$_3$ saturated with NH$_3$ to yield 0.56 g (6.6%) of 3; m.p. 144°-6° C. (CH$_3$CN).

Analysis Calc'd for C$_{20}$H$_{25}$N$_3$O$_3$S.

Compound S-3 was prepared as described for 3 except (S) 2-phenyl-3-(2-ethoxyethyl)-5-(hydroxymethyl)oxozolidine was used in place of racemic material. The compound was prepared as the HCl salt and crystallized from CH$_3$OH-isoProH to yield 1.7 g (9%) of S-3; m.p. 251°-4° C.; α$_D^{25}$ = −11.4° (C=0.8; CH$_3$OH).

Analysis calc'd for C$_{20}$H$_{25}$N$_3$O$_3$S.2HCl.1/2 H$_2$O
Calc'd: N, 8.95; C, 51.17; H, 6.01
Found: N, 8.90; C, 51.17; H, 6.01

EXAMPLE II (S)4-Hydroxymethyl-2-{4-[3-(3,4-dimethoxyphenethylamino)-2-hydroxypropoxy]phenyl}imidazole (6)

Step A:

4-Hydroxymethyl-2-(4-benzyloxyphenyl)-imidazole (4)

A mixture of dihydroxyacetone (18 g, 0.2 mole), Cu(OAc)$_2$ (80 g, 0.4 mol), 4-benzyloxybenzaldehyde (42.4 g, 0.2 mol), CH$_3$OH (450 ml) and aqueous concentrated NH$_3$ (450 ml) were heated at reflux for 1.25 h. After stirring overnight at room temperature, 65 g of the Cu salt of 4 was filtered off, suspended in H$_2$O (500 ml) and CH$_3$OH (500 ml) and the mixture heated on a steam bath while H$_2$S gas was bubbled in for ½ hr. The black suspension was filtered through super cel and the pad washed with CH$_3$OH (2x), and CHCl$_3$ (2x). After concentrating off the organic solvents under reduced pressure, the aqueous layer was extracted with CHCl$_3$ (3x). The organic extracts were dried, filtered, concentrated to dryness and the residue chromatographed on silica gel. The product was eluted with 5% CH$_3$OH—CHCl$_3$ and after evaporation of the solvents the residue was covered with CH$_3$CN, triturated and filtered to yield 16.2 g (29%) of 4. An analytical sample was prepared by crystallization from CH$_3$CN, m.p. 183°–185° C.
Analysis calculated for C$_{17}$H$_{16}$N$_2$O$_2$.

Step B:

4-Hydroxymethyl-2-(4-hydroxyphenyl)-imidazole (5)

A suspension of 4 (5 g, 0.018 mol), EtOH (250 ml) and 10% Pd/C (1.7 g) was hydrogenated on a Parr shaker at 50 psi. After shaking overnight, the suspension was filtered under N$_2$ through a super cel pad. The solution was concentrated to dryness to yield 3.2 g (94%) of 5. An analytical sample was prepared by crystallization from CH$_3$CN; m.p. 212°–214° C.
Analysis calculated for C$_{10}$H$_{10}$N$_2$O$_2$.

Under N$_2$ a suspension of NaH (60% oil dispersion 0.7 g, 0.017 mol), 5 (3.1 g, 0.016 mol) and DMSO (40 ml) was heated with stirring at 60° C. After 0.5 hr, a solution of (S)3-[2-(3,4-dimethoxyphenyl)ethyl]-5-(hydroxymethyl) oxazolid-2-one mesylate (5.7 g, 0.016 mol) in DMSO (40 ml) was added dropwise. After stirring overnight at 60° C., the solution was poured into H$_2$O and the pH adjusted to 10. The aqueous layer was extracted with CH$_2$Cl$_2$ (3 x) and the organic layer backwashed with H$_2$O (2 x), and saturated NaCl (1 x), dried, filtered and concentrated to dryness. The residue was treated with 10% NaOH (75 ml) and EtOH (75 ml) and the suspension heated to reflux. After 2h, the reaction mixture was poured into H$_2$O and extracted with CHCl$_3$ (3 x). The organic layers were washed with saturated NaCl, dried, filtered and concentrated to dryness. The residue was chromatographed on silica gel and the product eluted with 5% CH$_3$OH—CHCl$_3$ saturated with NH$_3$. After concentration of the solvents, the residue was crystallized from CH$_3$OH—CH$_3$CN to yield 0.4 g (6%) of 6, m.p. 145°–148° C.
Analysis calculated for C$_{23}$H$_{29}$N$_3$O$_5$.

EXAMPLE III (S) 4-Bromo-2-{p-[3-(3,4-dimethoxyphenethylamino)-2-hydroxypropoxy]phenyl}imidazole.dihydrochloride hemihydrate (12)

Step A:

2-(p-methoxyphenyl)-4-(trifluoromethyl)-imidazole (7)

A solution of 1,1-dibromo-3,3,3-trifluoro-acetone (68 g, 0.25 mol), NaOAc·3H$_2$O (68 g, 0.5 mol) in H$_2$O (280 ml) was heated with stirring on a steam bath for 0.5 h. The solution was cooled and added in one portion to a solution of anisaldehyde (34 g, 0.25 mol) in CH$_3$OH (1.3 l) and concentrated aqueous NH$_3$ (350 ml). After stirring overnight at room temperature, the methanol was concentrated off under reduced pressure and the resulting solid was filtered off to yield 29 g of 7. An analytical sample was prepared by crystallization from petroleum ether—EtOAc, m.p. 204°–206° C.
Analysis calculated for C$_{11}$H$_9$F$_3$N$_2$O.

Step B:

4-Bromo-2-(p-methoxyphenyl)-5-trifluoromethylimidazole (8)

To a solution of 7 (5 g, 0.025 mol) in CHCl$_3$ (200 ml) was added dropwise a solution of Br$_2$ (1.3 mol, d=3.1, 4.0 g, 0.25 mol) in 100 ml CHCl$_3$. After the addition, the solution was stirred at room temperature for 5 h, poured onto saturated Na$_2$CO$_3$ solution, and separated. The aqueous layer was extracted with CHCl$_3$ (3 x). The organic layers were dried, filtered and concentrated to dryness. The residue was chromatographed on silica gel and the product eluted with CHCl$_3$ to yield 4.4 g (65%) of 8. An analytical sample was prepared by crystallization from petroleum ether-CHCl$_3$, m.p. 177°–178° C.
Analysis calculated for C$_{11}$H$_8$BrF$_3$N$_2$O.

Step C:

Method A:

4-Bromo-2-(4-methoxyphenyl)imidazole-5-carboxylic acid (9)

A suspension of 8 (15.8 g, 0.49 mol) and 2.5 N NaOH (500 ml) was heated at reflux for 3 hours. The reaction mixture was cooled and the solution extracted with CH$_2$Cl$_2$ (2X). The aqueous layer was acidified with 12N HCl and the resulting solid filtered to yield 14.5 g (95%) of 9.

4-Bromo-2-(4-methoxyphenyl)imidazole hydrochloride (10)

A suspension of 9 (2.6 g, 0.0088 mol) in 8N HCl (100 ml) was heated at reflux for 20 hours. The solution was then cooled and filtered to yield 1.75 g (70%) of 10.

4-Bromo-2-(4-hydroxyphenyl)imidazole (11)

A suspension of 10 (2.6 g, 0.0091 mol) in AcOH (10 ml) and 48% HBr (40 ml) was heated at reflux for 10 hours. After stirring overnight at room temperature the solution was concentrated to dryness and the residue stirred overnight with saturated NaHCO$_3$. The mixture was filtered to yield 1.36 g (65%) of 11.

Method B: A suspension of 9 (2.5 g, 0.008 mol) in AcOH (10 ml) and 48% HBr (40 ml) was heated at reflux for 15 hours. The solution was concentrated to dryness and stirred overnight with saturated NaHCO$_3$. The suspension was filtered, the solids chromatographed on silica gel and eluted with 5% CH$_3$OH-CHCl$_3$ to yield 1.4 g (65%) of 11. An analytical sample was prepared by crystallization from CH$_3$CN, m.p. 210°–212° C.

Analysis calculated for C$_9$H$_7$BrN$_2$O.

Step D: Compound 12 was prepared as described in Example II for 6 except 11 was used in place of 5. The resulting free base was converted to the dihydrochloride salt with HCl-EtOH and crystallized from Et$_2$O-EtOH, m.p. 215°–7° C.

Analysis calc'd for C$_{22}$H$_{26}$BrN$_3$O$_4$·2HCl·1/2 H$_2$O:

EXAMPLE IV (S)
4-Chloro-2-{p-[3-(3,4-dimethoxyphenylethylamino)-2-hydroxypropoxy]phenyl}imidazole.dihydrochloride (14)

Step A: 4-Chloro-2-(p-hydroxyphenyl)imidazole (13)

Into a glass, thick-walled tube was placed 11 (1.5 g, 0.0063 mol) and 12N HCl (100 ml). The contents were frozen and the tube sealed and placed in a bath at 120° C. After 5 days, the contents in the tube were cooled, filtered, the solid stirred overnight with saturated NaHCO$_3$ solution and filtered to yield 0.59 g (49%) of 13.

Step B: Compound 14 was prepared as described in Example II except 13 was used in place of 5. The resulting free base was converted to the dihydrochloride salt with HCl-EtOH and crystallized from EtOH, m.p. 232°–4° C.

Analysis calc'd for C$_{22}$H$_{26}$ClN$_3$O$_4$·2HCl.

EXAMPLE V (S)4-Carboethoxy-2-{p-[3-(3,4-dimethoxyphenylethylamine)-2-hydroxypropoxy]phenyl}imidazole dihydrochloride hemihydrate (19)

Step A:
2-(p-Benzyloxyphenyl)-4-trifluoromethyl-imidazole (15)

A solution of 1,1-dibromo-3,3,3-trifluoroacetone (67.5 g, 0.025 mol), NaOAc·3H$_2$O (.05 mol), and H$_2$O (250 ml) was heated with stirring on a steam bath for 0.5 hour. The solution was cooled and added in one portion to a solution of p-benzyloxy benzaldehyde (53 g, 0.25 mol) in CH$_3$OH (1.4 liters) and concentrated aqueous NH$_3$ (400 ml). After stirring overnight at room temperature, the suspension was filtered and the CH$_3$OH in the filtrate was removed under reduced pressure. The resulting suspension was filtered and the filtrate extracted with CHCl$_3$ (3X). The organic layer was dried, filtered and concentrated to dryness. The residue and filtered solids were chromatographed on silica gel and the product eluted with CH$_2$Cl$_2$ to yield 55 g (69%) of 15.

Step B: 2-(p-Benzyloxyphenyl)imidazole-4-carboxylic acid (16)

A suspension of 15 (55 g, 0.017 mol) and 10% NaOH (2 l) was heated on a steam bath for 3 hours with stirring. After cooling in an ice bath, the reaction was acidified to pH 3.0 with 12 N HCl and stirred at room temperature overnight. The suspension was filtered and the solid dried to yield 38.2 g (75%) of 16.

Step C: 2-(Benzyloxyphenyl)-4-carboethoxyimidazole (17)

Under N$_2$, a suspension of 16 (11.5 g, 0.039 mol), NaH (60% oil dispersion, 1.64 g, 0.041 mol) and DMF (225 ml) was heated with stirring at 60° C. After 0.5 hour, a solution of ethyliodide (6.0 g, 0.039 mol) in DMF (75 ml) was added dropwise. After the addition, the reaction was allowed to stir at room temperature overnight, then poured into H$_2$O and extracted with EtOAc (4X). The combined organic layers were backwashed with H$_2$O, saturated Na$_2$CO$_3$, saturated NaCl, dried, filtered and concentrated to dryness. The residue was chromatographed on silica gel and the product eluted with 2% CH$_3$OH-CHCl$_3$ to yield 3.9 g (31%) of 17. An analytical sample was prepared by trituration with Et$_2$O, mp 203°–5° C.

Analysis calculated: C$_{19}$H$_{18}$N$_2$O$_3$.

Step D: 4-Carboethoxy-2-(p-hydroxymethyl)imidazole 18

A suspension of 17 (3.7 g, 0.011 mol), AcOH (200 ml) and 10% Pd/C (1.6 g) was hydrogenated on a Parr shaker at 54 psi. After shaking for 3 h., the suspension was filtered under N$_2$ through a super cel pad. The solution was concentrated to dryness to yield 2.45 g (90%) of 18. An analytical sample was prepared by chromatography on silica gel and the product eluted with 5% CH$_3$OH-CHCl$_3$. After concentration of the solvents and trituration with Et$_2$O, the product had m.p. 281°–2° C.

Analysis calculated for C$_{12}$H$_{12}$N$_2$O$_3$.

Step E: Compound 19 was prepared as described in Example I for 3 except 18 and (S) 2-phenyl-3-(3,4-dimethoxyphenylethyl)-5-hydroxymethyl)oxazolidine were used in place of 2 and 2-phenyl-3-(2-ethoxyethyl)-5-(hydroxymethyl)oxazolidine. The resulting free base was converted to the dihydrochloride salt with HCl-EtOH and crystallized from Et$_2$O-EtOH, m.p. 213°–5° C.

Analysis calc'd for C$_{25}$H$_{31}$N$_3$O$_6$·2HCl·1/2 H$_2$O.

EXAMPLE VI (S)-2-{3-Methyl-4-[3-(3,4-dimethoxyphenylethylamino)-2-hydroxypropoxy]phenyl}-4-(2-thienyl)imidazole dihydrochloride hydrate (25)

Step A: 4-Methoxy-3-methylbenzaldoxime (20)

A cold solution of hydroxylamine.hydrochloride (15 g, 0.22 mol) in H$_2$O (50 ml) was mixed with a cold solution of NaOH (20 g, 0.5 mol) in H$_2$O (150 ml) and then 4-methoxy-3-methylbenzaldehyde (30 g, 0.2 mol) was added in a steady stream. After stirring at room temperature for 30 minutes, the solution was saturated with CO$_2$. The separated solid was collected, washed with H$_2$O, and dried to yield 30.9 g (94%) of 20; m.p. 70°–2° C.

Analysis Calculated for C$_9$H$_{11}$NO$_2$ (165.19) C, 65.44; H, 6.71; N, 8.48.
Found: C, 65.11; H, 6.95; 8.19.

Step B: 4-Methoxy-3-methylbenzonitrile 21

A solution of 20 (30.9 g, 0.187 mole) in of acetic anhydride (200 ml) heated at reflux for 1.5 hours, cooled to room temperature and poured with vigorous stirring into 2N aqueous $Na_2CO_3$ (2 L). Overnight refrigeration gave a solid which was collected, washed with water, and dried to give 25.6 grams (93%) of 21 m.p. 48°-50°.
Analysis calculated for $C_9H_9NO$ (147.18): C, 73.45; H, 6.16; N, 9.52.
Found: C, 73.09; H, 6.41; N, 9.32.

Step C: 4-Methoxy-3-methylbenzamidine (22)

Under a nitrogen atmosphere was prepared a slurry of 21 (25.6 g, 0.174 mol) in a mixture of MeOH (10 ml) and $Et_2O$ (12 ml). With cooling, a stream of hydrogen chloride was passed through, giving a solution momentarily followed by a precipitate. The total uptake of HCl was 15 grams. The reaction mixture was refrigerated for 3 hours, and the solid collected and washed with $Et_2O$ to yield 31 grams (82%) of 4-methoxy-3-methylbenzimidate hydrochloride; m.p. 137–140°.
Analysis calculated for $C_{10}H_{14}ClNO_2$ (215.68): C, 55.68; H, 6.54; N, 6.50.
Found: C, 56.36; 56.46 (high); H, 6.70, 6.88; N, 6.58, 6.77.

To a solution of ammonia (22 grams) in cold $CH_3OH$ (200 ml) there was added 4-methoxy-3-methylbenzimidate hydrochloride (31 g, 0.144 mol). A slurry resulted and additional ammonia was added. The reaction mixture was allowed to stand overnight at room temperature and concentrated to dryness in vacuo to give a solid which was washed with $Et_2O$ and dried to yield 28.1 grams (97%) of the hydrochloride salt of 22; m.p. 221°-2° d.
Analysis calculated for $C_9H_{13}ClN_2O$ (200.67): C, 53.86; H, 6.53; N, 13.96.
Found: C, 53.98; H, 6.72; N, 14.04.

The free base was prepared by treating the hydrochloride salt of 22 (28.1 g, 0.14 mole) for 10 minutes with 10% aqueous NaOH (170 ml) and extracting with 10% $MeOH/CHCl_3$ (4X). The organic layers were dried and concentrated to give 21.6 grams (94%) of 22; m.p. 151-3°.
Analysis calculated for $C_9H_{12}N_2O$ (164.21): C, 65.83; H, 7.37; N, 17.06.
Found: C, 66.04; H, 7.61; N, 16.75.

Step D: 2-(3-Methyl-4-methoxyphenyl)-4-(2-thienyl)imidazole (23)

A slurry of 22 (21.6 g, 0.132 mol) in $CHCl_3$ (300 ml) was treated dropwise over 15 minutes with 2-(bromoacetyl)-thiophene (10.84, 0.0476 mol, 92% pure) in $CHCl_3$ (55 ml). The reaction mixture was stirred at room temperature for 24 hours, and then filtered to remove 10.2 g of the hydrobromide of 22. The mother liquors were concentrated to a semisolid which was swirled with 75 ml of methylene chloride and refrigerated overnight. The resultant gray solid was washed with $CH_2Cl_2$ and dried to give 10.2 grams (79%) of 23; m.p. 110°-114°. The analytical sample was dried in vacuo at 85°, m.p. 115°-117°.
Analysis calculated for $C_{15}H_{14}N_2OS$ (270.35): C, 66.64; H, 5.22; N, 10.36.
Found: C, 65.93; H, 5.30; N, 10.12.

Step E: 2-(3-Methyl-4-hydroxyphenyl)-4-(2-thienyl)imidazole (24)

To a solution of 23 (10.2 g, 0.0378 mol) glacial HOAc (50 ml) was added 48% aqueous HBr (190 ml) at room temperature and the reaction mixture was then heated at reflux for 4.4 hours. After standing overnight at room temperature, the solid hydrobromide salt of the product was filtered, washed with HOAc (50 ml), then with $Et_2O$ (2X) to give 11.3 of light green solid. The compound was added portionwise to 100 ml of saturated aqueous $NaHCO_3$ with stirring. After stirring overnight, the solid was collected, washed with $H_2O$, and dried to give 8.85 grams (90%) of 24l m.p. 167°-172° d. The analytical sample was dried at 90° in vacuo m.p., 172°-175° ($CH_3OH$).
Analysis calculated for $C_{14}H_{12}N_2OS$ (256.33): C, 65.60; H, 4.72; N, 10.93.
Found: C, 65.86; H, 4.84; N, 10.73.

Step F: To a solution of 24 (2.1 grams, 8.2 mmoles) in sieve-dried DMSO (20 ml) under nitrogen was added portionwise NaH (0.4 g, 8.34 mmoles; 50% in mineral oil). When gas evolution had ceased, the flask was lowered into a bath at 60°. After 10 minutes a solution of (S)3-[2-(3,4-dimethoxyphenyl)ethyl]-5-(hydroxymethyl)oxazolid-2-one mesylate in sieve-dried DMSO (20 ml) was added dropwise. Heating was continued overnight and the reaction mixture was poured into 200 ml of cold $H_2O$. A solid separated and the oxazolidone was collected, washed with water and dried to give 3.8 grams (89%) of crude product. A portion of the dried oxazolidone (2.87 g, 5.5 mmoles) was dissolved in a mixture of EtOH (50 ml) and 10% aqueous NaOH (50 ml) and heated at reflux for 3 hours under nitrogen. The solvents were removed in vacuo and 100 ml of $H_2O$ added. The aqueous layer was extracted with $CH_2Cl_2$ (3X), washed with $H_2O$ (2X), dried, filtered and concentrated to 1.71 grams (43%) of the free base of 25. To the free base 25 (1.5 g) in absolute EtOH was added HCl-EtOH (7.8 N, 0.7 ml) and the product crystallized from $Et_2O$-$CH_3OH$ to yield 0.21 g (35%) of 25.
Analysis calculated for $C_{27}H_{31}N_3O_4S\cdot2HCl\cdot H_2O$
Calc'd: C, 55.47; H, 6.04; N, 7.19.
Found: C, 55.08; H, 5.90; N, 7.03.
$\alpha_D{}^{25} = -9.6°$ (C=0.5, $H_2O$).

EXAMPLE VII (S)-2-{3-Chloro-4-[3-(3,4-dimethoxyphenylethylamino)-2-hydroxypropoxy]phenyl}-4-(2-thienyl)imidazole.dihydrochloride (30)

Step A: 3-Chloro-4-methoxybenzonitrile (26)

Under $N_2$, a solution of 3-chloro-4-hydroxybenzonitrile (15.4 g, 0.1 mole) in dry DMF (75 ml) was added rapidly dropwise to a stirred suspension of sodium hydride (4.0 g, 0.1 mole, 60% oil dispersion) in dry DMF (25 ml). After heating at 70° C. for 2 hours, the mixture was cooled to 20° C. and a solution of methyliodide (30 ml) in dry DMF (50 ml) was added dropwise. Following an 18 hour period at room temperature, the precipitate of sodium iodide was removed by filtration and the solvent was stripped from the filtrate under reduced pressure. The crystalline residue was slurried in water and the product was collected to yield 16.8 g (quant.) of 26, m.p. 105°–108° C. A sample recrystallized from IPA-H$_2$O melted at 107°–109° C.

Analysis calculated for C$_8$H$_6$ClNO: C, 57.33; H, 3.61; N, 8.36.
Found: C, 57.17; H, 3.60; N, 8.43.

Step B: 3-Chloro-4-methoxybenzamidine hydrochloride (27)

Under N$_2$, a stirred suspension of 26 (16.1 g, 0.096 mole) in CH$_3$OH (6 ml)—dioxane (20 ml) was cooled in an ice bath and saturated with gaseous HCl. The resulting mixture was refrigerated. After 3 days, the solid mass was suspended in Et$_2$O and the methyl 3-chloro-4-methoxybenzimidate hydrochloride was collected to afford 17.5 g (77%), m.p. 190°–192° C.

Methyl 3-chloro-4-methoxybenzimidate hydrochloride, (19.9 g, 0.084 mole) was added to a solution of ammonia (12 g) in CH$_3$OH (100 ml) cooled to −78° C. The stirred mixture was allowed to warm to room temperature. After 20 hours, the solution was evaporated to dryness under reduced pressure. The solid residue was triturated with Et$_2$O and collected to yield 17.8 g (96%) of 27, m.p. dec. 243°–245° C. A sample triturated with acetone melted at 241°–243° C. dec.

Analysis calculated for C$_8$H$_{10}$Cl$_2$N$_2$O:
C, 43.46; H, 4.56, N, 12.67.
Found: C, 42.84; H, 4.83; N, 12.74.

Step C: 2-(3-Chloro-4-methoxyphenyl)-4-(2-thienyl) imidazole (28)

Compound 28 was prepared as described for 23 except that 27 was used in place of 22. The crude product was chromatographed on silica gel, eluting with 2% CH$_3$OH—CHCl$_3$; 71% yield; m.p. 82°–5° C. (CH$_3$CN).
Analysis calculated for C$_{14}$H$_{11}$ClN$_2$OS: C, 57.83; H, 3.81; N, 9.64.
Found: C, 57.57; H, 3.90; N, 10.07.

Step D: 2-(3-Chloro-4-hydroxyphenyl)-4-(2-thienyl imidazole (29)

Compound 29 was prepared as described for 24 except that 28 was used in place of 23; 86% yield; m.p. 152°–3° C. (CHCl$_3$).

Step E: (S)-2-{3-Chloro-4-[3-(3,4-dimethoxyphenylethylamine)-2-hydroxypropoxy]phenyl}-4-(2-thienyl)imidazole dihydrochlorie (30)

Under N$_2$, sodium hydride (0.35 g, 7.3 mmole, 50% oil dispersion) was added to a stirred solution of 29 (2.0 g, 7.2 mmole) in dry DMSO (10 ml). The mixture was heated at 60° C. After 15 minutes when the hydrogen evolution was complete, a solution of (S)-3-(3,4-dimethoxyphenylethyl)-5-hydroxymethyl-oxazolid-2-one mesylate (2.62 g, 7.3 mmole) in dry DMSO (10 ml) was added dropwise. The resulting mixture was stirred at 60° C. overnight. After cooling to 5°–10° C., the mixture was quenched in ice water (150 ml). The solid product was collected, washed with cold water, and dissolved in absolute EtOH (35 ml). Aqueous NaOH (25 ml, 10%) was added and the mixture was heated to refluxing under N$_2$ for 2 hours. After concentration under reduced pressure, the residue was diluted with water and extracted with CH$_2$Cl$_2$. The washed and dried extract was evaporated to dryness to yield 2.6 g of the oily crude product that was purified by chromatography on silica gel, eluting with 85CHCl$_3$—15CH$_3$OH—1.5H$_2$O. The purified product was crystallized from CH$_3$CN to afford 1.5 g (40%), m.p. 170°–178° C., that was converted to the dihydrochloride salt with HCl-EtOH to yield 30; m.p. 252°–254° C. dec. (EtOH).
Analysis calculated for C$_{26}$H$_{28}$ClN$_3$O$_4$S (+2HCl): C, 53.20; H, 5.15; N, 7.16.
Found: C, 53.32; H, 5.32; N, 7.07.

EXAMPLE VIII (S)-2-{3-Bromo-4-[3-(3,4-dimethoxyphenylethylamino)-2-hydroxypropoxy]phenyl}-4-(2-thienyl)imidazole dihydrochloride (34)

Step A: 3-Bromo-4-methoxybenzamidine hydrochloride (31)

Compound 31 was prepared as described for 27 except that 3-bromo-4-methoxybenzonitrile was used in place of 26; m.p. 241°–2° C.; 85% yield; (trituration with acetone).
Analysis calculated for C$_8$H$_9$BrN$_2$O (+HCl): C, 36.18; H, 3.80; N, 10.55.
Found: C, 35.76; H, 3.83; N, 10.49.

Step B: 2-(3-Bromo-4-methoxyphenyl)-4-(2-thienyl) imidazole (32)

Compound 32 was prepared as described for 28 except that 31 was used in place of 27. The crude product was chromatographed on silica gel eluting with CHCl$_3$—CH$_3$OH (98:2) and rechromatographed eluting with C$_6$H$_5$CH$_3$-EtOAc (85:15); yield, 67%; m.p. 84°–87° C. (CH$_3$CN).
Analysis calculated for C$_{14}$H$_{11}$BrN$_2$OS: C, 50.16; H, 3.31; N, 8.36.
Found: C, 50.22; H, 3.43; N, 8.81.

Step C: 2-(3-Bromo-4-hydroxyphenyl)-4-(2-thienyl) imidazole (33)

A mixture of 32 (5.7 g, 0.017 mole), glacial HOAc (30 ml), and 48% HBr (85 ml) was stirred and heated at reflux for 12 hours. The hydrobromide salt that precipitated on cooling was collected and shown to consist of a mixture of 32 and 33. The mixture was resuspended in glacial HOAc (30 ml)–48% HBr (85 ml) and again heated at reflux for 12 hours. The precipitated hydrobromide was collected, washed with HOAc and Et$_2$O and then stirred with saturated NaHCO$_3$ (100 ml) for 2 days. The solid was collected, chromatographed on silica gel and the product eluted with 70 toluene—30 EtOAc to yield 1.2 g (22%) of 33, m.p. 125°–130° C.

Step D: (S)-2-{3-Bromo-4-[3-(3,4-dimethoxyphenylethylamino)-2-hydroxy-propoxy]phenyl}-4-(2-thienyl)imidazole dihydrochloride (34)

Compound 34 was prepared as described in Example VII for 30 except that 33 was used in place of 29; 16% yield; m.p. 260°–262° C. (EtOH).
Analysis calculated for C$_{26}$H$_{28}$BrN$_3$O$_4$S·2HCl: C, 49.45; H, 4.79; N, 6.65.
Found: C, 49.50; H, 4.87; N, 6.54.

EXAMPLE IX (S)-5-Bromo-2-{p-[3-(3,4-dimethoxyphenyle-thylamino)-2-hydroxypropoxy]phenyl}-4-methylimidazole dihydrochloride hemihydrate (37)

Step A:
5-Bromo-2-(p-methoxyphenyl)-4-methyl-imidazole (35)

2-(p-Methoxyphenyl)-4-methylimidazole, (5.0 g, 0.0265 mole), was dissolved in $CH_3CN$ (250 ml) at the boiling point. The solution was cooled to room temperature and stirred while a solution of pyridinium bromide perbromide (7.0 g) in $CH_3CN$ (70 ml) was added dropwise. A precipitate separated as the addition was completed (30 min) and stirring was continued for 30 minutes. The mixture was poured into water (1.5 L) and the precipitated hydrobromide salt was collected. The filtrate was made basic with saturated $Na_2CO_3$ solution and the product was collected, washed with water, and dried to afford 2.45 g, m.p. 183°–187° C. The hydrobromide salt was dissolved in hot $CH_3CN$ (75 ml)-$H_2O$ (25 ml) and the solution was made basic with saturated $Na_2CO_3$ solution. A second crop of product was collected, washed with water, and dried to yield 2.2 g of 35; m.p. 179°–184° C.; 65% combined yield. A sample of the first crop recrystallized from 50% $CH_3CN$ melted at 184°–187° C.

Analysis calculated for $C_{11}H_{11}BrN_2O$: C, 49.45; H, 4.15; N, 10.49
Found: C, 50.03; H, 4.36; N, 10.61.

Step B:
5-Bromo-2-(p-hydroxyphenyl)-4-methylimidazole (36)

Compound 36 was prepared as described for 33 except that 35 was used in place of 33; m.p. 205°–212° C.; 41% yield.

Step C:
5-Bromo-2-{p-[3-(3,4-dimethoxyphenylethylamino)-2-hydroxypropoxy]phenyl}-4-methylimidazole dihydrochloride hemihydrate (37)

Compound 37 was prepared as described in Example VII for 30, except that 36 was used in place of 29; m.p. 184°–186° C.; 16% yield (trituration with acetone). Analysis calculated for $C_{23}H_{28}BrN_3O_4$ (+2HCl+0.5$H_2O$): C, 48.26; H, 5.46; N, 7.34
Found: C, 48.54; H, 5.42; N, 7.21.

EXAMPLE X (S)-5-Chloro-2-{p-[3-(3,4-dimethoxyphenyle-thylamino)-2-hydroxypropoxy]phenyl}-4-methylimidazole dihydrochloride (40)

Step A:
5-Chloro-2-(p-methoxyphenyl)-4-methyl-imidazole (38)

A suspension of 2-(p-methoxyphenyl)-4-methylimidazole, (4.5 g, 0.024 mole) in concentrated HCl (96 ml)-$H_2O$ (34 ml) was stirred vigorously while a solution of $KClO_3$ (1 g) in $H_2O$ (50 ml) was added dropwise over 1-¼ hour. The precipitated hydrochloride salt was collected and suspended in $H_2O$ (200 ml), saturated $Na_2CO_3$ solution (50 ml). After an overnight period of stirring, the solid was collected, chromatographed on silica gel, the product eluted with 5% $CH_3OH$-$CHCl_3$ and crystallized from 50% $CH_3CN$ to yield 0.9 g (17%) of 38, m.p. 182°–186° C. A sample recrystallized from 50% $CH_3CN$ melted at 185°–187° C.

Analysis calculated for $C_{11}H_{11}ClN_2O$: C, 59.33; H, 4.98; N, 12.58
Found: C, 59.26; H, 5.06; N, 12.46.

Step B:
5-Chloro-2-(p-hydroxyphenyl)-4-methyl-imidazole (39)

Compound 39 was prepared as described for 33 except that 38 was used in place of 32; m.p. 226°–228° C.; 92% yield.

Step C:
5-Chloro-2-{p-[3-(3,4-dimethoxyphenylethylamino)-2-hydroxypropoxy]phenyl}-4-methylimidazole dihydrochloride (40)

Compound 40 was prepared as described in Example VII for 30 except that 39 was used in place of 29; 27% yield; m.p. 252°–4° C. ($Et_2O$-$CH_3OH$). Analysis calculated for $C_{23}H_{28}ClN_3O_4$.2HCl.

EXAMPLE XI (S)-5-Acetamido-2-{p-[3-(3,4-dimethoxyphenyle-thylamino)-2-hydroxypropoxy]phenyl}-4-methylimidazole dihydrochloride (44)

Step A:
2-(p-Methoxyphenyl)-4-methyl-5-nitroimidazole (41)

A mixture of 2-(p-methoxyphenyl)-4-methylimidazole (5.2 g, 0.0277 mole) and 3N $HNO_3$ (125 ml) was stirred at room temperature. After 15 minutes, the mixture was placed in a preheated 90° C. bath. Heating was continued for 20 minutes and the hot solution was continued for 20 minutes and the hot solution was quenched in ice-water (250 ml). The yellow solid was collected, washed with water, and suspended in cold saturated $NaHCO_3$ solution (25 ml). After a 15 minute period of stirring, the product was collected and recrystallized from 50% EtOH to yield 1.6 g (25%) of 41; m.p. 198°–204° C. A sample recrystallized from 50% EtOH melted at 199°–204° C.

Analysis calculated for $C_{11}H_{11}N_3O_3$: C, 56.65; H, 4.76; N, 18.02
Found: C, 56.41; H, 4.74; N, 17.66.

Step B:
5-Acetamido-2-(p-methoxyphenyl)-4-methylimidazole (42)

A solution of 41 (3.5 g, 0.015 mole) dissolved in glacial HOAc (35 ml)-acetic anhydride (105 ml) was hydrogenated at 50 psi over 5% platinum on charcoal catalyst (0.75 g) until uptake of hydrogen was complete. Catalyst was filtered off and the filtrate was evaporated to dryness under reduced pressure. The residue was dissolved in $H_2O$ (50 ml) and heated on a steam bath for 1 hour. The cooled solution was washed with ether (4×10 ml) and then evaporated to dryness in vacuo. Recrystallization of the residue from $CHCl_3$ gave 3.07 g (84%) of 42 in two crops; m.p. 202°–204° C.

Analysis calculated for $C_{13}H_{15}N_3O_2$: C, 63.66; H, 6.16; N, 17.13
Found: C, 63.54; H, 6.22; N, 17.50.

Step C:
5-Acetamido-2-(p-hydroxyphenyl)-4-methylimidazole (43)

Methylene chloride, 125 ml was stirred and cooled to −78° C. in an acetone-dry ice bath. Boron tribromide (7.5 ml, 0.079 mole) was added, followed by 42 (6.15 g, 0.025 mole). After a 10 minutes period at −78° C., the bath was removed and the mixture was stirred at ambient temperature under a $CaCl_2$ drying tube for 18 hours. The mixture was quenched in ice and water (500 ml) and the resulting mixture was neutralized with saturated $NaHCO_3$ solution to pH 7. The aqueous layer was separated and evaporated to dryness in vacuo. The residue was triturated with boiling IPA and filtered hot. Evaporation of the filtrate to dryness under reduced pressure left an oil that was chromatographed on silica gel. The product was eluted with 80 $CHCl_3$-20 $CH_3OH$ saturated with concentrated $NH_4OH$ and then triturated with $CH_3CN$ to yield 2.4 g (41%) of 43; m.p. 277°–279° C.
Analysis calculated for $C_{12}H_{13}N_3O_2$ (+½ $CH_3OH$): C, 61.50; H, 5.86; N, 17.57
Found: C, 61.45; H, 5.84; N, 17.69.

Step D:
5-Acetamido-2-{p-[(3,4-dimethoxyphenylethylamino)-2-hydroxypropoxy]phenyl}-4-methylimidazole dihydrochloride (44)

Compound 44 was prepared as described in Example VII for 30, except that 43 was used in place of 29; 26% yield; m.p. 270°–271° C. (EtOH).
Analysis calculated for $C_{25}H_{32}N_4O_5$ (+2 HCl): C, 55.45; H, 6.33; N, 10.35
Found: C, 55.57; H, 6.52; N, 10.29.

EXAMPLE XII (S)-5-Acetyl-2-{p-[3-(3,4-dimethoxyphenylethylamino)-2-hydroxypropoxy]phenyl}-4-methylimidazole·dihydrochloride (47)

Step A:
5-Acetyl-2-(4-methoxyphenyl)-4-methylimidazole (45)

To a solution of pentane-2,4-dione-3-oxime (23 g, 0.178 mol) in EtOAc (300 ml) was added p-methoxybenzylamine (24.4 g, 0.178 mol). The solution was heated at reflux with stirring for 2 hours and then concentrated at reduced pressure. The residue was dissolved in $CH_3CN$ (250 ml) and heated at reflux for 19 hours. After concentration at reduced pressure, the crude product was chromatographed on silica gel with 50:50 $C_6H_5CH_3$-EtOAc as eluant. The chromatographed product was recrystallized from EtOAc-$C_6H_{14}$ to give 17.0 g (41%) of 45, m.p. 162°–165° C.
Analysis calculated for $C_{13}H_{14}N_2O_2$: C, 67.81; H, 6.13; N, 12.17
Found: C, 67.94; H, 6.29; N, 12.04.

Step B:
5-Acetyl-2-(4-hydroxyphenyl)-4-methylimidazole (46)

A solution of 45 (1.0 g, 0.004 mol), glacial acetic acid (5.33 ml) and 48% HBr (22 ml) was heated at reflux for 3 hours with stirring. The reaction was cooled in an ice bath and the yellow precipitate was collected and combined with the residue resulting from concentration of the mother liquor. The solid was suspended in $H_2O$ (15 ml) and saturated $NaHCO_3$ solution (41 ml) and stirred at ambient temperature overnight. The solids were collected, washed with $H_2O$, and dried to yield 850 mg (98.4%) of 46; m.p. 300° C.

Step C:
(S)-5-Acetyl-2-{p-[3-(3,4-dimethoxyphenethylamino)-2-hydroxypropoxy]phenyl}-4-methylimidazole hydrochloride (47)

In a $N_2$ atmosphere, 46 (2.0 g, 0.009 mol) in sieve-dried DMSO (22 ml) was stirred at 60° while NaH (60% dispersion in mineral oil, 0.44 g, 0.009 mol) was added. After 10 minutes at 60° C., (S)-3-(3,4-dimethoxyphenyl)ethyl-5-(hydroxymethyl)-oxazolid-2-one mesylate (3.32 g, 0.009 mol) in sieve-dried DMSO (22 ml) was added dropwise over a 5-minute period. The reaction mixture was stirred at 60° C. for 3 hours and poured into cold $H_2O$ (120 ml). The mixture was extracted with $CH_2Cl_2$. The combined organic extracts were washed with $H_2O$, dried ($Na_2SO_4$) and evaporated under reduced pressure to give 3.45 g of crude oxazolidone.

The oily residue was dissolved with slight warming in absolute EtOH (48 ml). Aqueous 10% NaOH (48 ml) was added and the reaction mixture heated at reflux under $N_2$ atmosphere for 2 hours and then concentrated under reduced pressure. The residue was partitioned between $H_2O$ and $CH_2Cl_2$ (3X), $CHCl_3$ (1X) and EtOAc (1X). The combined organic layers were washed with $H_2O$, dried ($Na_2SO_4$), and concentrated under reduced pressure to yield 2.35 g of material that was chromatographed on silica gel. The product was eluted with 85:15 $CHCl_3$-$CH_3OH$ to yield 1.22 g. A sample was converted to the dihydrochloride salt yielding 870 mg of 47; m.p. 235°–237° C.
Analysis calculated for $C_{25}H_{31}N_3O_5$ (+2HCl): C, 57.04; H, 6.32; N, 7.98
Found: C, 56.71; H, 6.60; N, 7.74.

EXAMPLE XIII

2-{p-[[3-[6,7-Dimethoxy-2-(1,2,3,4-tetrahydronaphthyl)amino]-2-hydroxypropoxy]]phenyl}-4-(2-thienyl)imidazole (48)

A mixture of 3-{p-[4-(2-thienyl)-2-imidazolyl]phenoxy}-1,2-epoxypropane (5.37 g, 0.018 m) and 2-amino-6,7-dimethoxy-1,2,3,4-tetrahydronaphthalene (5.80 g, 0.028 m) in isopropanol (100 ml) was stirred at 70° for 23 hours. The solvent was evaporated under reduced pressure and the residue chromatographed on silica gel eluting with 5% MeOH-$CHCl_3$ saturated with $NH_3$. Compound 48 was crystallized as the dihydrochloride salt from MeOH; m.p. 280°–281° C.
Analysis Calculated for $C_{28}H_{31}N_3O_4S\cdot 2HCl$: C, 58.13; H, 5.75; N, 7.26.
Found: C, 58.11; H, 5.86; N, 7.53. (O.C. 1549–1184)

EXAMPLE XIV

4-Carbamoyl-2-{p-[3-(3,4-dimethoxyphenyle-thylamino)-2-hydroxypropoxy]phenyl}imidazole.dihydrochloride hemihydrate (50 )

Step A: (R,S) 4-Carboethoxy-2-{p-[3-(3,4-dimethoxy phenylethylamino)-2-hydroxypropoxy]phenyl-}imidazole (49)

Compound 49 was prepared as described for 19 in Example V except that 2-phenyl-3-(3,4-dimethoxyphenethyl)-5-(hydroxymethyl)oxazolidine was used in place of the (S) isomer; 7% yield.

Step B: (R,S) 4-Carbamoyl-2-{p-[3-(3,4-dimethoxyphenyle-thylamino)-2-hydroxypropoxy]phenyl}imidazole·dihydrochloride hemihydrate (50 )

A mixture of ester 49 (0.67 g, .0014 m), $CH_3OH$ (20 ml) and liquid $NH_3$ (10 ml) was heated in a sealed tube at 120° C. for 24 hours. After opening the tube, the contents were removed by washing with $CH_3OH$ and concentrating the contents to dryness. The residue was treated with HCl-EtOH, concentrated to dryness, and crystallized two times from $CH_3OH$ isopropanol to yield 0.24 g (33%) of 50, shrink at 169° C. dec.
Analysis Calculate for $C_{23}H_{28}N_4O_5 \cdot 2HCl \cdot 1/2\, H_2O$.

EXAMPLE XV (S)2-{4-[3-(3,4-Dimethoxyphenylethyl)amino-2-hydroxypropoxy]phenyl}-4-(morpholinomethyl)-imidazole·trihydrochloride·hydrate (54)

Step A: 4-Hydroxymethyl-2-(4-methoxyphenyl)-imidazole (51)

A mixture of dihydroxyacetone (28 g, 0.31 mol), $Cu(OAc)_2 \cdot H_2O$ (126 g, 0.63 mol), anisaldehyde (42 g, 0.31 mol), $CH_3OH$ (700 ml) and aqueous concentrated $NH_3$ (700 ml) was heated at reflux for 2 hours. After stirring overnight at room temperature, 55 g of the Cu salt of 51 was filtered off, suspended in $H_2O$ (1 L) and $CH_3OH$ (1 L) and the mixture heated on a steam bath while the solution was purged with $H_2S$ gas. The black suspension was filtered while hot through super cel and the pad washed while hot $CH_3OH$. After concentrating off most of the $CH_3OH$, the suspended product was filtered off to yield 18 g of 51. The aqueous layer was extracted with $CHCl_3$ (4 X), the organic extracts dried, filtered and concentrated to dryness and the residue triturated with $EtOH \cdot Et_2O$ to yield 3.8 g of additional 51 (total yield=34%) m.p. 171°-3° C.
Analysis calculated for $C_{11}H_{12}N_2O_2$.

Step B: Morpholinomethyl-2-(4-methoxyphenyl) imidazole (52)

To ice cold $SOCl_2$ (28 mol) was added 51 (3.0 g, 0.011 mol). After the addition, the mixture was stirred at room temperature overnight. The brown-black solution was concentrated to dryness, the residue flushed with toluene and the solid collected to yield 3.35 (91%) of the chloromethyl compound. Into a separate flask was placed under $N_2$, morpholine (2.7 g, 0.033 mol) and isopropanol (40 ml) to which the chloromethyl compound was added. The solution was heated at reflux for 5 hours and then poured into $Na_2CO_3$ solution. The resulting solution was extracted $CHCl_3$ (3 X), and the organic extracts dried, filtered and concentrated to dryness. The residue was chromatographed on silica gel and the product eluted with 5% $CH_3OH\text{-}CHCl_3$ to yield 2.85 g (95%) of 52. High resolution mass spectrum (273.1478) calcuates for $C_{15}H_{19}N_3O_2$.

Step C: 4-Morpholinomethyl-2-(4-hydroxyphenyl)imidazole (53)

Under $N_2$, a solution of 52 (2.25 g, .0082 mol) in $CH_2Cl_2$ (25 ml) was added dropwise to a dry-ice cooled solution of $BBr_3$ (2.5 ml, d=2.65, 0.0265 mol) in $CH_2Cl_2$ (75 ml). After the addition, the solution was stirred at room temperature overnight and then treated dropwise with $CH_3OH$ (50 ml). After stirring overnight at room temperature, the solution was concentrated to dryness, the residue treated with 10% NaOH, the aqueous layer extracted with $Et_2O$, the pH of the solution adjusted to 8.7 and concentrated to dryness. The residue was triturated with hot $CH_3OH$, filtered, the filtrate concentrated to dryness and the residue chromatographed on silica gel. The product was eluted with 10% $CH_3OH\text{-}CHCl_3$ to yield 1.75 g (82%) of 53.

Step D

Under $N_2$, a suspension of NaH (60% oil dispersion, 0.25 g, 0.0062 mol), 53 (1.6 g, 0.0062 mol) and DMSO (50 ml) was heated with stirring at 60° C. After 0.5 h, a solution of (S)3-[2-(3,4-dimethoxyphenyl)ethyl]-5-(hydroxymethyl)oxazolid-2-one mesylate (2.2 g, 0.0062 mol) in DMSO (50 ml) was added dropwise. After stirring overnight at 60° C., the solution was poured into $H_2O$ and the pH adjusted to 10. The aqueous layer was extracted with $CH_2Cl_2$ (4 X) and the organic layer backwashed with $H_2O$, saturated NaCl, dried, filtered and concentrated to dryness. The residue was treated with 10% NaOH (75 ml) and EtOH (75 ml) and the suspension heated at reflux with stirring. After 2 hours, the reaction mixture was poured into $H_2O$ and extracted with $CHCl_3$ (3 X). The organic layer was backwashed with $H_2O$, saturated NaCl, dried, filtered and concentrated to dryness. The residue was chromatographed on silica gel and the product eluted with 2% $CH_3OH\text{—}CHCl_3$ saturated with $NH_3$. After concentration of the solvent, the residue was crystallized as the hydrochloride salt from $CH_3OH$-isopropanol to yield 0.32 g (8%) of 54; m.p. 165°-70° C.
Analysis calculated for $C_{27}H_{36}N_4O_5 \cdot 3HCl\, H_2O$.

EXAMPLE XVI (S)2-{3-Chloro-4-[3-(3,4-dimethoxyphenylethylamino)-2-hydroxypropoxy]phenyl}-4-bromoimidazole (58)

Step A: 2-(3-Chloro-4-methoxyphenyl)-4-(trifluoromethyl)imidazole (55)

To a mixture of 7 (7.9 g, 0.033 mol), $H_2O$ (60 ml) and concentrated HCl (150 ml) stirred at room temperature was added dropwise a solution of $KClO_3$ (1.5 g, 0.012 mol) in $H_2O$ (65 ml). After 4 ½ hours, the suspension was filtered and the solid washed with $H_2O$ and dried in vacuo to yield 8.1 g (89%) of 55, m.p. 208–210.

Analysis Calculated for $C_{11}H_8ClF_3N_2O$.

Step B:
5-Bromo-2-(3-chloro-4-methoxyphenyl)-4-trifluoromethylimidazole (56)

To a suspension of 55 (2.56 g, 0.0092 mol) in CHCl₃ (75ml) was added dropwise with stirring a solution of bromine (1.55 g, 0.0096 mol) in CHCl₃ (75 ml). After stirring for 3 days, saturated NaHCO₃ was added, the layers separated and the aqueous layer extracted with CHCl₃ (2 x). The organic extracts were dried, filtered and concentrated to dryness. The residue was chromatographed on silica gel and the product eluted with 1.5% CH₃OH-CHCl₃ to yield 2.25 g (69%) of 56, m.p. 228.30° C. (CHCl₃). Analysis calculated for $C_{11}H_7BrClF_3N_2O$.

Step C:
4-Bromo-2-(3-chloro-4-hydroxyphenyl)-imidazole (57)

(a) A mixture of 56 (7.4 g, 0.021 mol) and 10% NaOH (200 ml) was heated at reflux with stirring. After 4 hours, the solution was cooled, extracted with CH₂Cl₂ (2 X), acidified with concentrated HCl, cooled and filtered to yield 100% of crude acid. The crude acid (6.9 g, 0.021 mol), AcOH (40 ml) and 48% HBr (160 ml) were heated at reflux with stirring. After 15 hours, the solution was concentrated to dryness and the residue treated with NaHCO₃. The mixture was concentrated to dryness and the residue combined with silica gel and chromatographed on silica gel and the product eluted with 5% CH₃OH-CHCl₃ to yield 3.0 g (53%) of 57, m.p. 225°-27° C. (CH₃CN). Analysis calculated for $C_9H_6N_2BrClO$.

Step D

Compound 58 was prepared as described in Example XV for 54 except that 57 was used in place of 53. The crude compound was chromatographed on silica gel eluting with 1% CH₃OH-CHCl₃ saturated with NH₃ to yield 0.6 g (22%) of 58; m.p. 172°-4° C. (CH₃CN). Analysis calculated for $C_{22}H_{25}ClBrN_3O_4$.

EXAMPLES XVII and XVIII (S)2-{4-[3-(3,4-Dimethoxyphenylethylamino-2-hydroxypropoxy]phenyl}-4-(methoxymethyl)imidazole·dihydrochloride·hydrate (61) and (S)2-{4-[3-(3,4-Dimethoxyphenylethylamino-2-hydroxypropoxy]phenyl}-4-(ethoxymethyl)imidazole·dihydrochloride·hemihydrate (62)

Step A:
2-(4-Benzyloxyphenyl)-4-(methoxymethyl)-imidazole (59)

To ice cold SOCl₂ (100 ml) was added 4 (10 g, 0.036 mol). After the addition, the mixture was stirred at room temperature overnight. The brown-black solution was concentrated to dryness, the residue flushed with toluene, treated with CH₃OH (250 ml) and heated at reflux with stirring overnight. The mixture was concentrated to dryness, the residue treated with saturated Na₂CO₃, and the aqueous solution extracted with CHCl₃ (3 X). The organic extracts were dried, filtered and concentrated to dryness to yield 10 g (95%) of 59; m.p. 146°-48° C. (CH₃CN). Analysis calculated for $C_{18}H_{18}N_2O_2$.

Step B:
2-(4-Hydroxyphenyl)-4-(methoxymethyl)-imidazole (60)

A suspension of 59 (4.6 g, 0.016 mol), EtOH (150 ml) and 10% Pd/C (1.5 g) was hydrogenated on a Parr shaker at 60.5 psi. After shaking overnight, the suspension was filtered under N₂ through super cel. The solution was concentrated to dryness to yield 3.2 g (100%) of 60; m.p. 191°-2° C. (CH₃CN). Analysis calculated for $C_{11}H_{12}N_2O_2$.

Step C

Compounds 61 and 62 were prepared as described in Example XV for 54 except that 60 was used in place of 53. After hydrolysis of the intermediate oxazolidone, the residue was chromatographed on silica gel eluting with CHCl₃ saturated with NH₃ to yield first free base 62 and then free base 61.

Crystallization of the second product off the column as the HCl salt from CH₃CN-Et₂O yielded 1.3 g (11%) of 61; m.p. 157°-9° C. Analysis calculated for $C_{24}H_{31}N_3O_5 \cdot 2HCl \cdot H_2O$ Crystallization of the first product off the column as the HCl salt from EtOH-Et₂O yielded 0.5 g (4%) of 62; m.p. 172-4° C.

Analysis calculated for $C_{25}H_{33}N_3O_5 \; 2HCl \; 1/2H_2O$

EXAMPLE XIX (S)4-Acetyl-2-{4-[3-(3,4-dimethoxyphenylethylamino)-2-hydroxypropoxy]phenyl}imidazole (68)

4-Carbomethoxy-2-(p-methoxyphenyl)imidazole (63)

A solution of methyl propiolate (25.4 g, 0.3 mol), p-methoxybenzamidoxime (50 g, 0.3 mol) and CH₃OH (700 ml) was heated at reflux with stirring. After 8 hours, the reaction mixture was concentrated to dryness, and the residue treated with diphenyl ether (300 ml) and heated at reflux. After 2.5 hours, the reaction mixture was poured in C₆H₁₄ (2 L) and allowed to stand. The C₆H₁₄ was decanted off and the residue chromatographed on silica gel. The product was eluted with 2% CH₃OH—CHCl₃ to yield 21 g (30%) of 63; m.p. 188°-90° C. (trituration with Et₂O). Analysis calculated for $C_{12}H_{12}N_2O_3$.

4-Carbamoyl-2-(4-methoxyphenyl)imidazole (64)

A mixture of 63 (21 g, 0.09 mol), CH₃OH (700 ml) and NH₃ (250 g) was heated in a sealed tube at 1220° C. for 24 hours. After washing out the contents, the suspension was concentrated to dryness and the residue crystallized from CH₃OH to yield 12.6 g (64%) of 64.

4-Cyano-2-(p-methoxyphenyl)imidazole (65)

A mixture of 64 (7.6 g, 0.035 mol) and POCl₃ (100 ml) was heated at reflux for 5.5 hours. After stirring at room temperature overnight, the suspension was poured into saturated Na₂CO₃ and the mixture extracted with 20% CH₃OH—CHCl₃ (3 X). The organic extracts were washed with saturated NaCl, dried, filtered and concentrated to dryness. The residue was chromatographed on silica gel and the product eluted with 5% CH₃O-

H—CHCl₃ to yield 5.0 g (71%) of 65; m.p. 219°–20° C. (CH₃CN). Analysis calculated for $C_{11}H_9N_3O$.

4-Acetyl-2-(4-methoxyphenyl)imidazole (66)

To a solution of 65 (0.199 g, 1.0 mmol) in dry THF (5 ml) was added 3M methylmagnesium bromide (1.0 ml, 3 mmol) in Et₂O dropwise with stirring under nitrogen. A white solid separated. The suspension was stirred at room temperature overnight. Then 3N HCl (10 ml) was added and the resulting solution was warmed for 15 minutes on the steam bath. The THF was removed in vacuo and the resulting aqueous suspension was neutralized with NaHCO₃ and was extracted with CH₂Cl₂. The CH₂Cl₂ extract was dried, filtered and concentrated in vacuo to yield 180 mg (83%) of 66; m.p. 248–250° C (CH₃CN).
Analysis calculated for $C_{12}H_{12}N_2O_2$.

4-Acetyl-2-(4-hydroxyphenyl)imidazole (67)

Compound 66 (2.16 g, 10 mmol) was dissolved in glacial AcOH (5 ml) and 48% hydrobromic acid (20 ml). The solution was stirred at reflux for 3 hours, cooled in ice and filtered to give 2.3 g of solid. The filtrate was concentrated to dryness in vacuo and another 0.35 g of solid was obtained. The combined solids were dissolved in H₂O (25 ml), the solution basified with excess NaHCO₃, the precipitated solid collected by filtration and dried to yield 1.9 g, (94%) of 67; m.p. 254°–259° C.
High resolution mass spectra analyzed for: $C_{11}H_{10}N_2O_2$ (MW 202.0742); Calcd (MW 202.0742)

(S)-4-Acetyl-2-{4-[3-(3,4-dimethoxyphenethylamino)-2-hydroxypropoxy]phenyl}imidazole (68)

To a solution of 67 (1.6 g, 8 mmol) in dry DMSO (10 ml) was added NaH (0.32 g of a 60% suspension in mineral oil, 8 mmol) under nitrogen with stirring. The mixture was warmed to 60° C. for 10 minutes and a solution of (S)-3-(3,4-dimethoxyphenethyl)-5-(hydroxymethyl)oxazolidin-2-one, methanesulfonate (2.9 g, 8 mmol) in dry DMSO (10 ml) added dropwise over 5 minutes. The reaction mixture was stirred at 60° C. for 3 hours, cooled, poured into 100 ml of ice water and extracted with 20% CH₃OH-CHCl₃. The extract was dried, filtered and concentrated in vacuo to obtain 3.8 g of crude amber oil.

The oil (3.8 g) in EtOH (40 ml) and 10% sodium hydroxide (40 ml) was heated at reflux for 2 hours and left at room temperature overnight. Removal of the solvents in vacuo gave an oily residue which was dissolved in dilute HCl and washed with Et₂O to remove mineral oil. The aqueous layer was neutralized with NaHCO₃ and extracted into 20% CH₃OH-CHCl₃. The extracts were dried, filtered and evaporated in vacuo. Trituration of the residual oil with CH₃OH gave 1.0 g of 68 (28%); m.p. 138°–142° C.
Analysis was calculated for $C_{24}H_{29}N_3O_5$.

EXAMPLE XX

(S)2-{4-[3-[[2-(3,4-Dimethoxyphenyl)ethyl]]amino]-2-hydroxypropoxy}phenyl-4-(2-methoxyethyl)imidazole dihydrochloride hemihydrate (73)

Step A:
2-(Benzyloxyphenyl)-4-(2-hydroxyethyl)imidazole (69)

A mixture of 2-butyne-1,4-diol (17.2 g, 0.2 mol), H₂SO₄ (2 g) was stirred at room temperature. After stirring for 3 days, the solution was neutralized with BaCO₃, filtered and the filtrate utilized directly in the next step without isolation.

To the filtrate from above was added CU(OAc)₂.H₂O (80 g, 0.4 mol), CH₃OH (900 ml), aqueous NH₃ (1 L) and 4-benzyloxybenzaldehyde (42.4 g, 0.2 mol). The mixture was heated at reflux with stirring for 2 hours, and stirred overnight at room temperature. The tan solid was filtered off to yield 70 g of the Cu salt of 69. The resulting solid was added to H₂O (1 L), and the pH adjusted to 3 and the resulting solution purged with H₂S for ½ hour. The solution was then heated on a steam bath while purging with N₂, the suspension filtered through super cel, the residue and super cel washed with hot CH₃OH (2 X), the filtrate adjusted to pH 10 and extracted with CH₂Cl₂ (4 X). The organic extracts were dried, filtered and concentrated to dryness. The residue was chromatographed on silica gel and the product eluted with 10% CH₃OH CHCl₃ to yield 11.1 g (19%) of 69; m.p. 131°–3° C. (CH₃CN). Analysis calculated for $C_{18}H_{18}N_2O_2$.

Step B:
2-(4-Benzyloxyphenyl)-4-(2-chloroethyl)-imidazole (70)

To a solution of thionyl chloride (25 ml) cooled in a dry ice bath was added 69 (2.5 g, 0.0085 mol), stirred for 5 minutes and then at room temperature. After stirring overnight at room temperature, the brown-black solution was concentrated to dryness, flushed with toluene, the residue treated with saturated Na₂CO₃, and the resulting aqueous layer extracted with CHCl₃ (3X). The organic extracts were dried, filtered and concentrated to dryness to yield 2.1 g (79%) of 70, m.p. 163°–5° C. (CH₃CN).
Analysis calculated for $C_{18}H_{17}ClN_2O$.

Step C:
2-(4-Benzyloxyphenyl)-4-(2-methoxyethyl)-imidazole (71)

Under N₂, Na (0.7 g, 0.029 mol) was added to CH₃OH (100 ml) and heated at reflux. After the Na had reacted, a solution of 70 (2.0 g, 0.0064 mol) in CH₃OH (75 ml) was added dropwise with stirring. After 15 hours, the suspension was concentrated to dryness to yield 1.85 g (94%) of 71, m.p. 154°–6° C.
Analysis calculated for $C_{19}H_{20}N_2O_2$.

Step D:
2-(4-Hydroxyphenyl)-2-(2-methoxyethyl)-imidazole (72)

A suspension of 71 (6.4 g, 0.021 mol), EtOH (250 ml) and 10% Pd/C (2 g) was hydrogenated on a Parr shaker at 53 psi. After shaking overnight, the suspension was filtered under N₂ through super cel. The solution was concentrated to dryness, the residue chromatographed on silica gel and the product eluted with 5% CH$_3$OH-CHCl$_3$ to yield 3.8 g (84%) of 72; m.p. 173°–6° C. (CH$_3$CN). Analysis calculated for C$_{12}$H$_{14}$N$_2$O$_2$.

Step E: Compound 73 was prepared as described in Example XIX for 68 except that 72 was used in place of 67. The crude product was chromatographed on silica gel eluting with 5% CH$_3$OH-CHCl$_3$ saturated with NH$_3$ to yield 4.5 g of material. This material was crystallized as the HCl salt from isoPrOH-Et$_2$O to yield 2.2 g (41%) of 73; m.p. 173°–5° C. Analysis calculated for C$_{25}$H$_{33}$N$_3$O$_5$·2HCl·1/2H$_2$O

EXAMPLE XXI (S)-2-{p-[3-(3,4-Dimethoxyphenethylamino)-2-hydroxypropoxy]phenyl}-4(5)-methoxymethyl-5(4)-methylimidazole, (76)

Step A: 2-(p-Hydroxyphenyl)-5-hydroxymethyl-4-methylimidazole, (74)

A suspension of 4-benzyloxyphenylamidine (5.0 g, 0.019 m) in H$_2$O (100 ml) was cooled to 0° C. and freshly distilled butane-2,3-dione (2.07 g, 0.024 m) was added, followed by 2.5N sodium hydroxide solution (7.6 ml) and the mixture stirred at 0° C. for 2 hours. The solid was collected, washed with acetone and dried at 40° C. The product was stirred in 3N HCl (140 ml) while heating on a steam bath for 4 hours. The mixture was concentrated under reduced pressure to yield 2.96 g (63%) of 74 which was used in the subsequent reaction without further purification.

Step B: 2-(p-Hydroxyphenyl)-5-methoxymethyl-4-methylimidazole, (75)

Thionyl chloride (55 ml) was cooled to 0° C. and 74 (2.92 g, 0.012 m) was added and the suspension stirred at ambient temperature for 21 hours. The mixture was concentrated under reduced pressure and the residue heated at reflux in absolute CH$_3$OH (90 ml) for 18 hours. The solution was evaporated under reduced pressure and the residue chromatographed on silica gel eluting with 10% CH$_3$OH—CHCl$_3$ saturated with NH$_3$ to yield 1.60 g (61%) of 75; m.p. 181° C. (CH$_3$CN).
Analysis calculated for C$_{12}$H$_{14}$N$_2$O$_2$: C, 66.03; H, 6.47; N, 12.84.
Found: C, 66.17; H, 6.41; N, 12.66.

Step C: (S)-2-{p-[3-(3,4-Dimethoxyphenethylamino)-2-hydroxypropoxy]phenyl}-4(5)-methoxymethyl-5(4)-methylimidazole, (76)

Sodium hydride (0.34 g, 0.0071 m, 50% dispersion in mineral oil) was added to a solution of 75 (1.50 g, 0.0069 m) in DMSO (17 ml) and the mixture heated at 60° C. under nitrogen for 10 minutes. A solution of (S)-3-(3,4-dimethoxyphenyl)ethyl-5-(hydroxymethyl)oxazolid-2-one mesylate (2.55 g, 0.0071 m) jin DMSO (17 ml) was added and the mixture heated at 60° C. for 3 hours. After cooling, the reaction mixture was poured into cold H$_2$O (170 ml), rendered strongly alkaline with 40% sodium hydroxide solution and extracted with CH$_2$Cl$_2$ (3×50 ml). After washing with H$_2$O and drying over Na$_2$SO$_4$, the extract was concentrated under reduced pressure. The residue was refluxed under N$_2$ for 2 hours in a mixture of EtOH (50 ml) and 10% NaOH solution (50 ml). Ethanol was evaporated under reduced pressure, H$_2$O (100 ml) added and the product extracted with CH$_2$Cl$_2$. The extract was evaporated under reduced pressure and the residue subjected to preparative TLC eluting with 5% CH$_3$OH—CHCl$_3$ saturated with NH$_3$. The product was crystallized as the dihydrochloride salt from CH$_3$OH—EtOH; m.p. 228°–231° C.
Analysis calculated for C$_{25}$H$_{33}$N$_3$O$_5$·2HCl: C, 56.82; H, 6.68; N, 7.95.
Found: C, 56.39; H, 6.44; N, 8.38.

EXAMPLE XXII

1-Phenyl-3-{2-[[2-hydroxy-3-[4-(2-imidazoyl)phenoxy]propylamino]]ethyl}urea, (77)

A mixture of 1-(2-aminoethyl)-3-phenylurea (1.13 g, 0.0063 m) and 3-[p-(2-imidazolyl)phenoxy]-1,2-epoxypropane (1.36 g, 0.0063 m) in isopropanol (20 ml) was stirred at 70° C. for 3 hours. The solvent was evaporated under reduced pressure and the residue was chromatographed on silica gel eluting with 20% CH$_3$OH—CHCl$_3$ saturated with NH$_3$ to yield 1.24 g (50%) of 77; m.p. 159°–161° C. (CH$_3$CN-CH$_3$OH).
Analysis calculated for C$_{21}$H$_{25}$N$_5$O$_3$: C, 63.78; H, 6.37; N, 17.71.
Found: C, 63.46; H, 6.49; N, 17.52.

EXAMPLE XXIII

2-{p-[3-(4-Pyridylethylamino)-2-hydroxypropoxy]phenyl}-4-(2-thienyl)imidazole Hemihydrate, (78)

A mixture of 3-{p-[4-(2-thienyl)-2-imidazolyl]phenoxy}-1,2-epoxypropane (5.0 g, 0.017 m) and 4-(2-aminoethyl)pyridine (3.18 g, 0.026 m) in isopropanol (90 ml) was stirred at 70° C. for 23 hours. The solvent was evaporated under reduced pressure and the residue chromatographed on silica gel and eluted with 5% MeOH-CHCl$_3$ saturated with NH$_3$, and then rechromatographed eluting with 10% MeOH-CHCl$_3$ saturated with NH$_3$. Compound 78 was isolated as an amorphous solid.
Analysis Calculated for C$_{23}$H$_{24}$N$_4$O$_2$S.O.5H$_2$O: C, 64.31; H, 5.87; N, 13.0
Found: C, 64.61; H, 5.87; N, 12.84.

EXAMPLE XXIV 2-(n-Butyl)-3-{2-[[2-hydroxy-3-[4-(4-methyl-2-imidazoyl)phenoxypropyl]amino]]ethyl}urea, (84)

Step A: 3-[p-(4-Methyl-2-imidazolyl)phenoxy]-1,2-propanediol Acetonide, (79)

Prepared as previously described for 3-{p-[4-(2-thienyl)-2-imidazolyl]phenoxy}-1,2-propanediol acetonide starting with 2-(p-hydroxyphenyl)-4-methylimidazole (10.38 g, 0.060 m), sodium hydride (3.6 g, 0.075 m, 50% dispersion in mineral oil), and 2,2-dimethyl-4-(hydroxymethyl)-1,3-dioxolane methane sulfonate (12.6 g, 0.060 m) in DMF (32 ml). The yield of 79 was 8.88 g which was used without further purification.

Step B:
3-[p-(4-Methyl-2-imidazolyl)phenoxy]-1,2-propanediol, (80)

A mixture of 79 (8.8 g, 0.031 m) in 3N HCl (70 ml) and acetone (70 ml) was refluxed for 45 minutes. Acetone was removed under reduced pressure and the aqueous mixture rendered alkaline with $K_2CO_3$. The solid was collected and dried in a vacuum oven at 60° C. to yield 80 (5.14 g, 67%, m.p. 196°–199° C.).

Step C:
3-[p-(4-Methyl-2-imidazolyl)phenoxy]-1,2-propanediol-1-methanesulfonate, (81)

A mixture of 80 (5.10 g, 0.021 m), pyridine hydrochloride (2.66 g, 0.023 m) and pyridine (45 ml) was cooled in an ice bath and stirred while methanesulfonyl chloride (2.41 g, 0.021 m) was added over 10 minutes. The mixture was stirred at 25° C. for 2 hours, then a cold solution of $K_2CO_3$ (2.90 g, 0.021 m) in $H_2O$ (15 ml) added and the mixture concentrated below 50° C. under high vacuum. The residue was chromatographed on silica gel and eluted with 15% MeOH-CHCl$_3$ to yield 81 (2.78 g, 41%).

Step D:
3-[p-(4-Methyl-2-imidazolyl)phenoxy]-1,2-epoxypropane, (82)

A solution of 81 (2.75 g, 0.0084 m) in CH$_3$OH (32) and methylene chloride (32 ml) was cooled in an ice bath while a solution of NaOCH$_3$ (0.43 g, 0.008 m) in CH$_3$OH (8 ml) was added over 10 minutes with stirring. After stirring at 0° C. for 1.5 hours, H$_2$O (130 ml) was added and the organic layer separated. The aqueous layer was extracted with CH$_2$Cl$_2$ (2×150 ml) and the combined organic layers were dried and the solvent concentrated under reduced pressure to yield 82 (1.84 g, 95%).

Step E: 1-(n-Butyl)-3-(2-aminoethyl)urea, (83)

A solution of n-butylisocyanate (19.83 g, 0.2 m) in Et$_2$O (50 ml) was added over 40 minutes to a vigorously stirred solution of ethylenediamine (48.08 g, 0.8 m) in isopropanol (1000 ml). After stirring at 25° C. for 3 hours, and standing for about 16 hours, the mixture was filtered and the filtrate evaporated to dryness under reduced pressure initially using water aspiration and finally high vacuum at 70° C. The residue was stirred for 1 hour in 12N HCl (20 ml) and H$_2$O (200 ml), filtered and the filtrate rendered alkaline with 40% NaOH and evaporated to dryness under reduced pressure. The residue was chromatographed on silica gel and eluted with 20% MeOH-CHCl$_3$ saturated with NH$_3$ to give 83 (19.7 g, 59%).

Step F:
1-(n-Butyl)-3-{2-[[2-hydroxy-3-[4-(4-methyl-2-imidazoyl)phenoxypropyl]amino]]ethyl}urea, (84)

A mixture of 82 (1.8 g, 0.0078 m) and 83 (1.91 g, 0.012 m) in isopropanol (45 ml) was stirred at 70° C. for 20 hours. The solvent was evaporated under reduced pressure and the residue chromatographed on silica gel, eluting with 20% MeOH—CHCl$_3$ saturated with NH$_3$ to yield 84 (0.96 g, 32%); m.p. 171°–172.5° C. (CH$_3$OH—CH$_3$CN).

Analysis Calculated for $C_{20}H_{31}N_5O_3$: C, 61.67; H, 8.02; N, 17.98.
Found: C, 61.66; H, 8.32; N, 17.70.

EXAMPLE XXV

2-{4-[2-(3,4-Dimethoxyphenyl)ethyl]amino-2-hydroxypropoxy}phenyl-4-(methoxymethyl)imidazole.dihydrochloride (93)

Step A: 2-(p-Benzyloxyphenyl)imidazole-4-carboxylic acid (85)

A solution of 1,1-dibromo-3,3,3-tribromoacetone (68 g, 0.25 mol), H$_2$O (280 ml) and NaOAc.3H$_2$O (68 g, 0.5 mol) was heated on a steam bath for 30 minutes. The cooled solution of trifluoromethylglyoxal was then added to a mixture of 4-benzyloxybenzaldehyde (53 g, 0.25 mol), CH$_3$OH (1.3 l) and concentrated aqueous NH$_3$ (340 ml) with stirring at room temperature. After 18 hours, the CH$_3$OH was removed under reduced pressure and 2.5N NaOH (1.5l) was added to the residue. After heating for 3 hours on a steam bath, the mixture was filtered through super cel and the clear solution acidified with excess concentrated HCl. After cooling the solid was removed by filtration and dried to yield 27.5 g (37%) of 85.

Step B:
1-Benzyl-2-(p-benzyloxyphenyl)imidazole-4-carbobenzyloxy (86)

To a mixture of 85 (53.8 g, 0.18 mol), DMF (1 l) and NaH (16.3 g, 0.4 mol, 60% oil dispersion) was added dropwise under N$_2$ with stirring at 120° C. a solution of benzyl bromide (63.8 g, 0.37 mol) in DMF (150 ml). After 18 hours, the cooled solution was poured into H$_2$O and the product extracted with EtOAc (4 x). The organic layers were backwashed with H$_2$O (2 x), saturated NaHCO$_3$, saturated NaCl, dried, filtered and concentrated to dryness to yield 74 g of 86.

Step C:
1-Benzyl-4-hydroxymethyl-2-(p-benzyloxylphenyl)imidazole (87)

To a mixture of LAH (13 g, 0.34 mol) in THF (1 l) was added dropwise under N$_2$ at −5° C. a solution of crude ester 86 (74 g) in THF (400 ml). After the addition, a saturated Na$_2$SO$_4$ solution was added dropwise until a white suspension was observed. The mixture was filtered and the pad washed with CHCl$_3$. The filtrate was concentrated and H$_2$O added to the residue. The aqueous solution was extracted with CHCl$_3$ (3 x) and the organic layers dried, filtered and concentrated to dryness. The residue was triturated with Et$_2$O to yield 34 g (51%) of 87; m.p. 129°–31° C.

Analysis calculated for $C_{24}H_{22}N_2O_2$.

Step D:
1-Benzyl-4-methoxymethyl-2-(p-benzyloxy)phenyl imidazole (88)

Under N$_2$ a mixture of NaH (4.5 g, 0.11 mol, 60% oil dispersion), DMF (500 ml) and 87 (36 g, 0.097 mol) was heated on a steam bath with stirring for 30 minutes. The mixture was then cooled to room temperature and a solution of CH₃I (15.6 g, 0.11 mol) in DMF (120 ml) was added dropwise over 1 hour. After 18 hours, the mixture was poured in H₂O and the product extracted with EtOAc (4 x). The organic layers were backwashed with H₂O (2 x) saturated NaCl, dried, filtered and concentrated to dryness. The residue was chromatographed on silica gel and the product eluted with 2% CH₃OH-CHCl₃ to yield 21.3 g (57%) of 88.

Step E:
2-(4-Hydroxyphenyl)-4-(methoxymethyl)imidazole (89)

A mixture of 88 (8.9 g, 0.023 mol), EtOH (300 ml) and 10% Pd/C (2 g) was hydrogenated on a Parr shaker until the theoretical amount of H₂ was consumed. The mixture was then filtered under a blanket of N₂ and the filtrate concentrated to dryness. The residue was chromatographed on silica gel and the product eluted with 10% CH₃OH—CHCl₃ to yield 3.35 g of 89 (71%), m.p. 191°-2° C. (CH₃CN).
Analysis calculated for $C_{11}H_{12}N_2O_2$.

Step F:
3-{p-(4-Methoxymethyl-2-imidazolyl)phenoxy}-1,2-propanediol (90)

Under N₂, a mixture of NaH (1.5 g, 0.037 mol), 60% oil dispersion), DMF (45 mol) and 89 (6.9 g, 0.033 mol) was heated at 80° C. for 30 minutes and then a solution of 2,2-dimethyl-4-(hydroxymethyl)-1,3-dioxolane methanesulfonate (8.4 g, 0.04 mol) in DMF (25 ml) was added dropwise. After the addition, the mixture was heated to 120° C. with stirring for 18 hours. The mixture was then poured into H₂O and the solution extracted with EtOAc (4 x). The combined organic extracts were backwashed with H₂O, 5% NaOH, dried, filtered and concentrated to dryness. The residue was combined with acetone (75 ml) and 3N HCl (75 ml) and the solution heated on a steam bath for 30 minutes. After cooling, the solution was adjusted to pH 10 and extracted with 10% CH₃OH—CHCl₃. The combined extracts were dried, filtered and concentrate to dryness. The residue was chromatographed on silica gel and the product eluted with 10% CH₃OH-CHCl₃ to yield 1.7 g of 90 (18%); m.p. 154°-56° C. (isoProOH).

Step G:
3-{p-(4-Methoxymethyl-2-imidazolyl)phenoxy}-1,2-propanediol-1-methanesulfonate (91)

A mixture of 90 (6.3 g, 0.023 mol), pyridine HCl (2.9 g, 0.25 ml) and pyridine (40 ml) was cooled in an ice bath and stirred while methanesulfonylchloride (2.6 g, 0.023 mol) was added dropwise. After stirring for 10 minutes, the ice bath was removed and the mixture stirred at room temperature. After 1.5 hours, a solution of K₂CO₃ (3.1 g, 0.023 mol) in H₂O was added and the mixture concentrated to dryness below 50° C. The residue was chromatographed on silica gel and the product eluted with 10% CH₃OH-CHCl₃ to yield 6.6 g of 91 (81%).

Step H:
3-{p-(4-Methoxymethyl-2-imidazolyl)phenoxy}-1,2-epoxypropane (92)

A solution of 91 (6.6 g, 0.019 mol) in CH₃OH (100 ml) and CH₂Cl₂ (100 ml) was cooled to −4° C. and then a solution of NaOCH₃ (0.41 g Na in CH₃OH, 0.018 mol) in CH₃OH (20 ml) was added dropwise under N₂. After 3 hours, the suspension was poured into H₂O and the resulting mixture extracted with CHCl₃ (3x). The organic layer was backwashed with H₂O, saturated NaCl, dried, filtered and concentrated to dryness to yield 4.8 g (92%) of 92.

Step I:
2-{4-[3-[[2-(3,4-Dimethoxyphenyl)ethyl]]amino]-2-hydroxypropoxy}phenyl-4-(methoxymethyl)imidazole.dihydrochloride (93)

A mixture of 92 (2.2 g, 0.0085 mol), 2-(3,4-dimethoxyphenyl)ethylamine (1.5 g, 0.0083 mol), isopropanol (60 ml) and CH₃OH (20 ml) was heated at reflux. After 18 hours, the solution was concentrated to dryness, the residue chromatographed on silica gel and the product eluted with 5% CH₃OH-CHCl₃ saturated with NH₃. The product was crystallized as the dihydrochloride salt from isopropanol to yield 1.0 g (23%) of 93, m.p. 178°-80° C.
Analysis calculated for $C_{24}H_{31}N_3O_5.2HCl$.

EXAMPLE XXVI

2-{p-[3-(1-Phenyl-3-butyl)amino-2-hydroxypropoxy]phenyl}-4-(2-thienyl)imidazole·dihydrochloridesalt salt (96)

Step A: 3-(1-Phenyl-3-butyl)amino-1,2-propanediol (94)

A solution of glycidol (11.5 g, 0.155 mol) in isopropanol (25 ml) was added dropwise under N₂ at 40° C. to a solution of 1-phenyl-3-butylamine in isopropanol (50 ml). After 1 hour, the solution was heated to 70° C. for 1.5 hours and then at room temperature overnight. The isopropanol was removed under reduced pressure and the residue distilled to yield 24 g (70%) of 94; b.p.₀.₂ 140°-5° C.

Step B: 2-Phenyl-3-(1-phenyl-3-butyl)-5-(hydroxymethyl)oxazolidine (95)

A solution of 94 (24 g, 0.108 mol), toluene, benzaldehyde (40 ml) and benzoic acid (0.5 g) was heated at reflux with a Dean-Stark trap. After 1 hour, the theoretical amount of H₂O was collected, the reaction cooled to room temperature and saturated Na₂CO₃ added. The aqueous layer was separated and washed with CHCl₃ (3X). The combined extracts were dried, filtered and concentrated to dryness to yield 34 g (100%) of 95.

Step C: 2-{p-[3-(1-Phenyl-3-butyl)amino-2-hydroxypropoxy]phenyl}-4-(2-thienyl)imidazole dihydrochloride (96)

A solution of 95 (7.6 g, 0.025 mol) in pyridine (15 ml) was cooled in an ice bath and p-toluenesulfonyl chloride (4.7 g, 0.025 mol) was added while keeping the internal temperature below 30° C. After stirring for 3 hours at room temperature, a saturated solution of Na₂CO₃ was added and the mixture extracted with CH₂Cl₂ (3X). The organic extracts were dried, filtered and concentrated under reduced pressure below 50° C. initially using water aspirator pressure and finally high vacuum to yield the p-toluene sulfonate of 95 (0.025 mol).

Under N₂, sodium hydride (0.9 g, 0.022 mole, 60% oil dropwise) was added to DMF (20 ml) and heated to 70° C. while a solution of 2-(p-hydroxyphenyl)-4-(2-thienyl-)imidazole (4.5 g, 0.018 mol) in DMF (40 ml) was added dropwise. After heating at 70° C. for 15 minutes a solution of p-toluene sulfonate of 95 (0.025 mol) in DMF (40 ml) was added dropwise and the mixture heated at 120° C. After 18 hours, the DMF was removed under reduced pressure, the residue suspended in 1N HCl and heated on a steam bath for 30 minutes. The acid solution was extracted with EtOAc (2X), basified to pH >10 and extracted with CH₂Clhd 2 (4X). The CH₂Cl₂ extracts were dried, filtered and concentrated to dryness. The residue was chromatographed on silica gel and the product eluted with 5% CH₃OH—CHCl₃ saturated with NH₃. The product was crystallized as the dihydrochloride salt from CH₃OH-IPA to yield 0.95 g (10%) of 96; m.p. 156°-166° C. Analysis calculated for $C_{26}H_{29}N_3O_2S\cdot 2HCl$.

What is claimed is:

1. A compound of the formula:

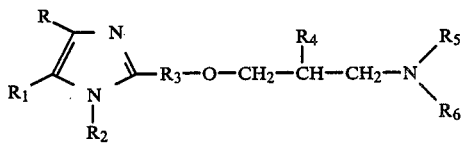

wherein:
R and $R_1$ are independently selected from:
(a) hydrogen;
(b) $C_5$-$C_{10}$ linear or branched alkyl;
(c) substituted $C_1$-$C_{10}$ linear or branched alkyl having 1-3 substituents selected from the group consisting of fluoro, bromo, chloro, hydroxy, $C_1$-$C_4$ alkoxy, morpholino, di($C_1$-$C_4$ alkyl)amino;
(d) unsubstituted or substituted aryl of $C_6$ or $C_{10}$ and the substituents are 1-2 halo or $C_1$-$C_6$ alkoxy group;
(e) pentafluorophenyl;
(f) halo (fluoro, chloro, bromo);
(g) carboxy and carbalkoxy;
(h)

wherein $R_a$ is hydrogen or $C_1$-$C_6$ alkyl, and;
(i)

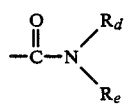

wherein $R_d$ and $R_e$ are hydrogen $C_1$-$C_8$ linear or branched alkyl, $C_6$ or $C_{10}$ unsubstituted or substituted aryl having 1-2 substituents selected from $C_1$-$C_4$ linear or branched alkyl, halo, alkoxy or hydroxy;
(j) $C_1$-$C_6$ alkanoylamino provided that at least one of R and $R_1$ is selected from (b) to (j);
$R_2$ is (a) hydrogen;
(b) $C_1$-$C_{10}$ linear or branced alkyl;
$R_3$ is

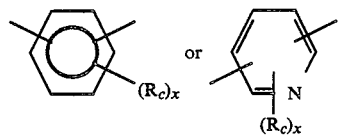

wherein $R_c$ is
(a) hydrogen
(b) halo;
(c) $C_1$-$C_4$ alkyl;
(d) $C_1$-$C_4$ alkoxy;
(e) hydroxy;
x is 0-4;
$R_4$ is hydroxy;
$R_5$ and $R_6$ are independently:
(a) hydrogen;
(b) $C_1$-$C_6$ alkyl;
(c) $C_1$-$C_6$ substituted alkyl wherein the substituent is selected from alkoxy, methoxyphenyl or dimethoxyphenyl; provided that at least one of $R_5$ and $R_6$ is a substituent selected from (b) and (c), and provided that when $R_3$ is

and $R_6$ is (b), R is selected from (d)—(j) inclusive, and when $R_3$ is

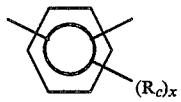

and $R_6$ is (c), R is selected from (c)—(j) inclusive; or a pharmaceutically acceptable acid addition salt or a quaternary ammonium salt thereof.

2. A compound according to claim 1 which is a racemate, an enantiomer or a mixture of enantiomers.

3. A compound according to claim 1 wherein $R_2$, $R_3$ and $R_4$ are as above defined, $R_1$ and $R_2$ are independently:
(a) hydrogen;
(b) phenyl;
(c) chlorophenyl;
(d) fluorophenyl;
(e) methoxyphenyl;
(f) difluorophenyl;
(g) pentafluorophenyl;
(h) trifluoromethyl;
(i) carbomethoxy;
(j) carbamoyl;
(k) hydroxymethyl;
(l) bromo;
(m) chloro;
(n) carboethoxy;
(o) acetyl;
(p) ethoxymethyl;
(q) methyl;

(r) acetylamino;
(s) morpholinomethyl;
(t) methoxymethyl;
(u) methoxyethyl;

$R_5$ and $R_6$ are independently:
(a) hydrogen;
(b) t-butyl;
(c) dimethoxyphenylethyl.

4. A compound according to claim 3 in which $R_3$ is

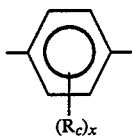

5. A compound which is a member of the group consisting of:

(S)4-hydroxymethyl-2-{4-[3-(3,4-dimethoxyphenethylamino)-2-hydroxypropoxy]phenyl}imidazole;

(S)4-bromo-2-{p-[3-(3,4-dimethoxyphenethylamino)-2-hydroxypropoxy]phenyl}imidazole·dihydroxychloride hemihydrate;

(S)4-chloro-2-{p-[3-(3,4-dimethoxyphenylethylamino)-2-hydroxypropoxy]phenyl}imidazole dihydrochloride;

(S)4-carboethoxy-2-{p-[3-(3,4-dimethoxyphenylethylamine)-2-hydroxypropoxy]phenyl}imidazole·dihydrochloride hemihydrate;

(S)-5-bromo-2-{p-[3-(3,4-dimethylphenylethylamino)-2-hydroxypropoxy]phenyl}-4-methylimidazole dihydrochloride hemihydrate;

(S)-5-chloro-2-{p-[3-(3,4-dimethoxyphenylethylamino)-2-hydroxypropoxy]phenyl}-4-methylimidazole dihydrochloride;

4-carbamoyl-2-{p-[3-(3,4-dimethoxyphenylethylamino)-2-hydroxypropoxy]phenyl}imidazole·dihydrochloride·hemihydrate;

(S)2-{4-[3(3,4-dimethoxyphenylethyl)amino-2-hydroxypropoxy]phenyl}-4-(morpholinomethyl)-imidazole·trihydrochloride·hydrate;

(S)2-{3-chloro-4-[3-(3,4-dimethoxyphenylethylamino)-2-hydroxypropoxy]phenyl}-4-bromoimidazole;

(S)2-{4-[3-(3,4-dimethoxyphenylethylamino-2-hydroxypropoxy]phenyl}-4-(methoxymethyl)imidazole·dihydrochloride·hydrate;

(S)2- {4-[3-(3,4-dimethoxyphenylethylamino)-2-hydroxypropoxy]phenyl}-4-(ethoxymethyl)imidazole·dihydrochloride·hemihydrate;

(S)4-acetyl-2-{4-[3-(3,4-dimethoxyphenylethylamino)-2-hydroxypropoxy]phenyl}imidazole;

(S)2-{4-[3-[[2-(2,3-dimethoxyphenyl)ethyl]]amino]-2-hydroxypropoxy}phenyl-4-(2-methoxyethyl)-imidazole}dihydrochloride hemihydrate;

(S)-2-{p-[3-(3,4-dimethoxyphenethylamino)-2-hydroxypropoxy]-phenyl}-4(5)-methoxymethyl-5(4)-methylimidazole; and 2-{4-[2-(3,4-dimethoxyphenyl)ethyl]amino-2-hydroxypropoxy}phenyl-4-(methoxymethyl)imidazole·dihydrochloride;

5-acetamido-2-{4-(3,4-dimethoxyphenylethylamino)-2-hydroxypropoxy]phenyl}-4-methylimidazole·dihydrochloride.

6. A pharmaceutical composition useful for treating hypertension or effecting β-adrenergic blockade comprising a pharmaceutically acceptable carrier; and, a pharmaceutically effective amount of a compound of claim 1.

7. A pharmaceutical composition useful for treating hypertension or effecting β-adrenergic blockade comprising a pharmaceutically acceptable carrier; and, a pharmaceutically effective amount of a compound of claim 5.

8. A method for treating hypertension, arrhythmia, or angina, or effecting β-adrenergic blockade, or providing cardioprotection comprising administering to a patient in need of such treatment a pharmaceutically effective amount of a compound of claim 1 in a dose range from 0.01 to 50 mg/kg.

9. A method for treating hypertension, arrhythmia, or angina, or effecting β-adrenergic blockade, or providing cardioprotection comprising administering to a patient in need of such treatment a pharmaceutically effective amount of a compound of claim 5 in a dose range from 0.01 to 50 mg/kg.

* * * * *